US012753442B2

(12) United States Patent
Mahnke et al.

(10) Patent No.: US 12,753,442 B2
(45) Date of Patent: Oct. 6, 2026

(54) SIGNATURE miRNA TO PREDICT NEONATAL OPIOID WITHDRAWAL SYNDROME (NOWS)

(71) Applicants: UNM RAINFOREST INNOVATIONS, Albuquerque, NM (US); TEXAS A & M UNIVERSITY SYSTEM, College Station, TX (US)

(72) Inventors: Amanda Mahnke, Bryan, TX (US); Rajesh Miranda, Bryan, TX (US); Ludmila Bakhireva, Los Ranchos, NM (US)

(73) Assignees: UNM RAINFOREST INNOVATIONS, Albuquerque, NM (US); TEXAS A & M UNIVERSITY SYSTEMS, College Station, TX (US)

( * ) Notice: Subject to any disclaimer, the term of this patent is extended or adjusted under 35 U.S.C. 154(b) by 443 days.

(21) Appl. No.: 18/012,839

(22) PCT Filed: Jun. 25, 2021

(86) PCT No.: PCT/US2021/039154
§ 371 (c)(1),
(2) Date: Dec. 23, 2022

(87) PCT Pub. No.: WO2021/263142
PCT Pub. Date: Dec. 30, 2021

(65) Prior Publication Data

US 2024/0263235 A1 Aug. 8, 2024

Related U.S. Application Data

(60) Provisional application No. 63/044,528, filed on Jun. 26, 2020.

(51) Int. Cl.
*C12Q 1/6883* (2018.01)

(52) U.S. Cl.
CPC ..... *C12Q 1/6883* (2013.01); *C12Q 2600/158* (2013.01); *C12Q 2600/178* (2013.01); *G01N 2800/52* (2013.01)

(58) Field of Classification Search
None
See application file for complete search history.

(56) References Cited

U.S. PATENT DOCUMENTS

2006/0009478 A1* 1/2006 Friedmann ........... A61K 31/485
514/282

OTHER PUBLICATIONS

Yen et al Journal of Pediatrics. 214:60-65 (Year: 2019).*
Alles et al. An estimate of the total number of true human miRNAs. Nucleic Acids Research. 47(7): 3353-3364 (Year: 2019).*
Mahnke et al. Neonatal cord blood miRNAs as biomarkers of neonatal opioid withdrawal syndrome. Birth Defects. May 2019. 111(9) , Abstract No. 16, p. 493, and meeting schedule, 15 pages total (Year: 2019).*
Mangat et al. Pharmacological and Non-pharmacological treatments for the Neonatal Abstinence Syndrome (NAS). Semin Fetal Neonatal Med. 24(2): 133-141 (Year: 2019).*
Bakhireva et al. MicroRNAs in maternal peripheral blood and umbilical cord blood as biomarkers of prenatal exposure to substances of abuse and brain health. GLIA, 65, Supplement 1, p. E242-E243, abstract T08-024A. (Year: 2017).*
Acloque, H., Adams, M.S., Fishwick, K., Bronner-Fraser, M., and Nieto, M.A. (2009). Epithelial-mesenchymal transitions: the importance of changing cell state in development and disease. J Clin Invest 119, 1438-1449. 10.1172/JCI38019.
Al-Hashimi, M., Scott, S.W.M., Thompson, J.P., and Lambert, D.G. (2013). Opioids and immune modulation: more questions than answers. British journal of anaesthesia 111, 80-88. 10.1093/bja/aet153.
Ambros, V. (2004). The functions of animal microRNAs. Nature 431, 350-355. 10.1038/nature02871.
American College of Obstetricians and Gynecologists (2017). Opioid Use and Opioid Use Disorder in Pregnancy. Committee Opinion No. 711. . Obstetrics & Gynecology 130, e81-e94. 10.1097/aog.0000000000002235.
Bagley, S., Wachman, E.M., Holland, E., and Brogly, S.B. (2014). Review of the assessment and management of neonatal abstinence syndrome. Addiction Science & Clinical Practice 9, 19-19. 10.1186/1940-0640-9-19.
Bakhireva, L.N., Cano, S., Rayburn, W.F., Savich, R.D., Leeman, L., Anton, R.F., and Savage, D.D. (2012). Advanced gestational age increases serum carbohydrate-deficient transferrin levels in abstinent pregnant women. Alcohol and alcoholism (Oxford, Oxfordshire) 47, 683-687. 10.1093/alcalc/ags087.

(Continued)

*Primary Examiner* — Carla J Myers
(74) *Attorney, Agent, or Firm* — Cosud Intellectual Property Solutions, P.C.; Henry D. Coleman

(57) ABSTRACT

The present invention relates to the discovery of miRNAs which can be isolated from the blood of neonates, especially the umbilical cord and/or placental blood of neonates which have been determined to be biomarkers for neonatal opioid withdrawal syndrome (NOWS). One or more of these biomarkers, often at least three in conjunction may be measured in the blood, preferably the cord or placental blood of neonates suspected of having opioid withdrawal syndrome and compared with a standard wherein the measurement of the one or more biomarkers evidences the presence of opioid syndrome in the neonate whose blood has been measured so that effective measures can be taken to treat, the withdrawal syndrome and inhibit, limit and/or reverse withdrawal syndrome in the neonate shortly after birth. In an embodiment, the cord and/or placental blood of an unborn neonate may be obtained and analyzed for opioid withdrawal syndrome, in an embodiment, one or more biomarkers as identified herein may be utilized to determine the effectiveness of therapy by measuring the biomarker at more than one time during a period of therapy for opioid withdrawal syndrome to determine if the concentration of biomarker has normalized to levels closer to that of a standard.

16 Claims, 43 Drawing Sheets

Specification includes a Sequence Listing.

(56) References Cited

OTHER PUBLICATIONS

Bakhireva, L.N., Holbrook, B.D., Shrestha, S., Leyva, Y., Ashley, M., Cano, S., Lowe, J., Stephen, J.M., and Leeman, L. (2019). Association between prenatal opioid exposure, neonatal opioid withdrawal syndrome, and neurodevelopmental and behavioral outcomes at 5-8 months of age. Early Hum Dev 128, 69-76. 10.1016/j.earlhumdev.2018.10.010.
Bakhireva, L.N., Leeman, L., Savich, R.D., Cano, S., Gutierrez, H., Savage, D.D., and Rayburn, W.F. (2014). The validity of phosphatidylethanol in dried blood spots of newborns for the identification of prenatal alcohol exposure. Alcoholism, clinical and experimental research 38, 1078-1085. 10.1111/acer.12349.
Bakhireva, L.N., Lowe, J.R., Gutierrez, H.L., and Stephen, J.M. (2015). Ethanol, Neurodevelopment, Infant and Child Health (Enrich) prospective cohort: Study design considerations. Adv Pediatr Res 2. 10.12715/apr.2015.2.10.
Bakhireva, L.N., and Savage, D.D. (2011). Focus on: biomarkers of fetal alcohol exposure and fetal alcohol effects. Alcohol research & health : the journal of the National Institute on Alcohol Abuse and Alcoholism 34, 56-63.
Balaraman, S., Schafer, J.J., Tseng, A.M., Wertelecki, W., Yevtushok, L., Zymak-Zakutnya, N., Chambers, C.D., and Miranda, R.C. (2016). Plasma miRNA profiles in pregnant women predict infant outcomes following prenatal alcohol exposure. PLoS One 11, e0165081. 10.1371/journal.pone.0165081.
Baldacchino, A., Arbuckle, K., Petrie, D.J., and McCowan, C. (2015). Erratum: neurobehavioral consequences of chronic intrauterine opioid exposure in infants and preschool children: a systematic review and meta-analysis. BMC Psychiatry 15, 134. 10.1186/s12888-015-0438-5.
Bär, C., Thum, T., and de Gonzalo-Calvo, D. (2019). Circulating miRNAs as mediators in cell-to-cell communication. Epigenomics 11, 111-113. 10.2217/epi-2018-0183.
Barbierato, M., Zusso, M., Skaper, S.D., and Giusti, P. (2015). MicroRNAs: emerging role in the endogenous mu opioid system. CNS Neurol Disord Drug Targets 14, 239-250. 10.2174/1871527314666150116123932.
Bartel, D.P. (2004). MicroRNAs: genomics, biogenesis, mechanism, and function. Cell 116, 281-297. 10.1016/s0092-8674(04)00045-5.
Beauchamp, K.G., Lowe, J., Schrader, R.M., Shrestha, S., Aragon, C., Moss, N., Stephen, J.M., and Bakhireva, L.N. (2020). Self-regulation and emotional reactivity in infants with prenatal exposure to opioids and alcohol. Early Hum Dev 148, 105119. 10.1016/j.earlhumdev.2020.105119.
Blondal, T., Jensby Nielsen, S., Baker, A., Andreasen, D., Mouritzen, P., Wrang Teilum, M., and Dahlsveen, I.K. (2013). Assessing sample and miRNA profile quality in serum and plasma or other biofluids. Methods 59, S1-6. 10.1016/j.ymeth.2012.09.015.
Cao, J.M., Li, G.Z., Han, M., Xu, H.L., and Huang, K.M. (2017). MiR-30c-5p suppresses migration, invasion and epithelial to mesenchymal transition of gastric cancer via targeting MTA1. Biomed Pharmacother 93, 554-560. 10.1016/j.biopha.2017.06.084.
Ceolotto, G., Giannella, A., Albiero, M., Kuppusamy, M., Radu, C., Simioni, P., Garlaschelli, K., Baragetti, A., Catapano, A.L., lori, E., et al. (2017). miR-30c-5p regulates macrophage-mediated inflammation and pro-atherosclerosis pathways. Cardiovasc Res 113, 1627-1638. 10.1093/cvr/cvx157.
Chau, Y.Y., Brownstein, D., Mjoseng, H., Lee, W.C., Buza-Vidas, N., Nerlov, C., Jacobsen, S.E., Perry, P., Berry, R., Thornburn, A., et al. (2011). Acute multiple organ failure in adult mice deleted for the developmental regulator Wt1. PLoS Genet 7, e1002404. 10.1371/journal.pgen.1002404.
Chavan, N.R., Ashford, K.B., Wiggins, A.T., Lofwall, M.R., and Critchfield, A.S. (2017). Buprenorphine for Medication-Assisted Treatment of Opioid Use Disorder in Pregnancy: Relationship to Neonatal Opioid Withdrawal Syndrome. AJP Rep 7, e215-e222. 10.1055/s-0037-1608783.
Cohen, J. (1988). Statistical Power Analysis For the Behavioral Sciences, 2nd ed Edition (L. Erlbaum Associates).
Dai, X., Song, H.J., Cui, S.G., Wang, T., Liu, Q., and Wang, R. (2010). The stimulative effects of endogenous opioids on endothelial cell proliferation, migration and angiogenesis in vitro. Eur J Pharmacol 628, 42-50. 10.1016/j.ejphar.2009.11.035.
Dai, Y., Zhang, Z., Cao, Y., Mehta, J.L., and Li, J. (2016). MIR-590-5p Inhibits Oxidized-LDL Induced Angiogenesis by Targeting LOX-1. Sci Rep 6, 22607. 10.1038/srep22607.
Doberczak, T.M., Kandall, S.R., and Wilets, I. (1991). Neonatal opiate abstinence syndrome in term and preterm Infants. J Pediatr 118, 933-937. 10.1016/s0022-3476(05)82214-0.
Finnegan, L.P., Connaughton, J.F., Kron, R.E., and Emich, J.P. (1975). Neonatal abstinence syndrome: assessment and management. Addictive diseases 2, 141-158.
Firth, D. (1993). Bias Reduction of Maximum Likelihood Estimates. Biometrika 80, 27-38. 10.2307/2336755.
Ganguli, A., Mostafa, A., Berger, J., Aydin, M.Y., Sun, F., Ramirez, S.A.S., Valera, E., Cunningham, B.T., King, W.P., and Bashir, R. (2020). Rapid isothermal amplification and portable detection system for SARS-CoV-2. Proc Natl Acad Sci U S A 117, 22727-22735. 10.1073/pnas.2014739117.
Gardiner, A.S., Gutierrez, H.L., Luo, L., Davies, S., Savage, D.D., Bakhireva, L.N., and Perrone-Bizzozero, N.I. (2016). Alcohol use during pregnancy is associated with specific alterations in microRNA levels in maternal serum. Alc Clin Exp Res In press.
Gill, P., and Ghaemi, A. (2008). Nucleic acid isothermal amplification technologies: a review. Nucleosides Nucleotides Nucleic Acids 27, 224-243. 10.1080/15257770701845204.
Gopman, S. (2014). Prenatal and Postpartum Care of Women with Substance Use Disorders. Obstetrics and Gynecology Clinics of North America 41, 213-228. 10.1016/j.ogc.2014.02.004.
Grossman, M.R., Berkwitt, A.K., Osborn, R.R., Xu, Y., Esserman, D.A., Shapiro, E.D., and Bizzarro, M.J. (2017). An Initiative to Improve the Quality of Care of Infants With Neonatal Abstinence Syndrome. Pediatrics 139. 10.1542/peds.2016-3360.
Haight, S.C., Ko, J.Y., Tong, V.T., Bohm, M.K., and Callaghan, W.M. (2018). Opioid Use Disorder Documented at Delivery Hospitalization—United States, 1999-2014. MMWR Morb Mortal Wkly Rep 67, 845-849. 10.15585/mmwr.mm6731a1.
Hattie, J. (2009a). Visible learning : a synthesis of over 800 meta-analyses relating to achievement (Routledge).
He, Y., Yang, C., Kirkmire, C.M., and Wang, Z.J. (2010). Regulation of opioid tolerance by let-7 family microRNA targeting the mu opioid receptor. J Neurosci 30, 10251-10258. 10.1523/JNEUROSCI.2419-10.2010.
Heinze, G., and Schemper, M. (2002). A solution to the problem of separation in logistic regression. Stat Med 21, 2409-2419. 10.1002/sim.1047.
Herzlinger, R.A., Kandall, S.R., and Vaughan, H.G., Jr. (1977). Neonatal seizures associated with narcotic withdrawal. J Pediatr 91, 638-641. 10.1016/s0022-3476(77)80523-4.
Hudak, M.L., and Tan, R.C. (2012). Neonatal drug withdrawal. Pediatrics 129, 2011-3212.
Hwang, C.K., Wagley, Y., Law, P.Y., Wei, L.N., and Loh, H.H. (2012). MicroRNAs in opioid pharmacology. J Neuroimmune Pharmacol 7, 808-819. 10.1007/s11481-011-9323-2.
Isemann, B.T., Stoeckle, E.C., Taleghani, A.A., and Mueller, E.W. (2017). Early Prediction Tool to Identify the Need for Pharmacotherapy in Infants at Risk of Neonatal Abstinence Syndrome. Pharmacotherapy 37, 840-848. 10.1002/phar.1948.
Jacobson, S.W., Chiodo, L.M., Sokol, R.J., and Jacobson, J.L. (2002). Validity of maternal report of prenatal alcohol, cocaine, and smoking in relation to neurobehavioral outcome. Pediatrics 109, 815-825. 10.1542/peds.109.5.815.
Jansson, L.M., and Patrick, S.W. (2019). Neonatal Abstinence Syndrome. Pediatr Clin North Am 66, 353-367. 10.1016/j.pcl.2018.12.006.
Jantzie, L.L., Maxwell, J.R., Newville, J.C., Yellowhair, T.R., Kitase, Y., Madurai, N., Ramachandra, S., Bakhireva, L. N., Northington, F.J., Gerner, G., et al. (2020). Prenatal opioid exposure: The next neonatal neuroinflammatory disease. Brain, Behavior, and Immunity 84, 45-58. https://doi.org/10.1016/j.bbi.2019.11.007.

(56) References Cited

OTHER PUBLICATIONS

Ji, Y., Feng, G., Hou, Y., Yu, Y., Wang, R., and Yuan, H. (2020). Long noncoding RNA MEG3 decreases the growth of head and neck squamous cell carcinoma by regulating the expression of miR-421 and E-cadherin. Cancer Med 9, 3954-3963. 10.1002/cam4.3002.

Jones, H.E., Seashore, C., Johnson, E., Horton, E., O'Grady, K.E., and Andringa, K. (2016). Measurement of neonatal abstinence syndrome: Evaluation of short forms. J Opioid Manag 12, 19-23. 10.5055/jom.2016.0308.

Kaltenbach, K., O'Grady, K.E., Heil, S.H., Salisbury, A.L., Coyle, M.G., Fischer, G., Martin, P.R., Stine, S., and Jones, H.E. (2018). Prenatal exposure to methadone or buprenorphine: Early childhood developmental outcomes. Drug Alcohol Depend 185, 40-49. 10.1016/j.drugalcdep.2017.11.030.

Kandall, S.R., Albin, S., Gartner, L.M., Lee, K.S., Eidelman, A., and Lowinson, J. (1977). The narcotic-dependent mother: fetal and neonatal consequences. Early Hum Dev 1, 159-169. 10.1016/0378-3782(77)90017-2.

Koshkin, A.A., Singh, S.K., Nielsen, P., Rajwanshi, V.K., Kumar, R., Meldgaard, M., Olsen, C.E., and Wengel, J. (1998). LNA (Locked Nucleic Acids): Synthesis of the adenine, cytosine, guanine, 5-methylcytosine, thymine and uracil picyclonucleoside monomers, oligomerisation, and unprecedented nucleic acid recognition. Tetrahedron 54, 3607-3630. https://doi.org/10.1016/S0040-4020(98)00094-5.

Larson, J.J., Graham, D.L., Singer, L.T., Beckwith, A.M., Terplan, M., Davis, J.M., Martinez, J., and Bada, H.S. (2019). Cognitive and Behavioral Impact on Children Exposed to Opioids During Pregnancy. Pediatrics 144. 10.1542/peds.2019-0514.

Leeman, L.M., Brown, S.A., Albright, B., Skipper, B., Hsi, A., and Rayburn, W.F. (2011). Association between Intrapartum fetal heart rate patterns and neonatal abstinence syndrome in methadone exposed neonates. The journal of maternal-fetal & neonatal medicine : the official journal of the European Association of Perinatal Medicine, the Federation of Asia and Oceania Perinatal Societies, the International Society of Perinatal Obstetricians 24, 955-959. 10.3109/14767058.2010.536863.

Lennon, F.E., Mirzapoiazova, T., Mambetsariev, B., Poroyko, V.A., Salgia, R., Moss, J., and Singleton, P.A. (2014). The Mu opioid receptor promotes opioid and growth factor-induced proliferation, migration and Epithelial Mesenchymal Transition (EMT) in human lung cancer. PLoS One 9, e91577. 10.1371/journal.pone.0091577.

Lewis, T., Dinh, J., and Leeder, J.S. (2015). Genetic determinants of fetal opiate exposure and risk of neonatal abstinence syndrome: Knowledge deficits and prospects for future research. Clin Pharmacol Ther 98, 309-320. 10.1002/cpt.159.

Li, S., Hao, J., Hong, Y., Mai, J., and Huang, W. (2020). Long Non-Coding RNA NEAT1 Promotes the Proliferation, Migration, and Metastasis of Human Breast-Cancer Cells by Inhibiting miR-146b-5p Expression. Cancer Manag Res 12, 6091-6101. 10.2147/CMAR.S252295.

Li, Y., Han, X., Li, Q., Wang, C., Lou, Z., and Wang, X. (2019). Long noncoding RNA HOXD-AS1 induces epithelial-mesenchymal transition in breast cancer by acting as a competing endogenous RNA of miR-421. J Cell Biochem 120, 10633-10642. 10.1002/jcb.28353.

Lim, J., and Thiery, J.P. (2012). Epithelial-mesenchymal transitions: insights from development. Development 139, 3471-3486. 10.1242/dev.071209.

Long, X., Li, Y., Qiu, S., Liu, J., He, L., and Peng, Y. (2016). MIR-582-5p/miR-590-5p targeted CREB1/CREB5-NF-kappaB signaling and caused opioid-induced immunosuppression in human monocytes. Transl Psychiatry 6, e757. 10.1038/tp.2016.4.

Mahnke, A.H., Sideridis, G.D., Salem, N.A., Tseng, A.M., Carter, R.C., Dodge, N.C., Rathod, A.B., Molteno, C.D., Meintjes, E.M., Jacobson, S.W., et al. (2021a). Infant circulating MicroRNAs as biomarkers of effect in fetal alcohol spectrum disorders. Scientific reports 11, 1429. 10.1038/s41598-020-80734-y.

McCall, M.N., McMurray, H.R., Land, H., and Almudevar, A. (2014). On non-detects in qPCR data. Bioinformatics 30, 2310-2316. 10.1093/bioinformatics/btu239.

McGlone, L., and Mactier, H. (2015). Infants of opioid-dependent mothers: neurodevelopment at six months. Early Hum Dev 91, 19-21. 10.1016/j.earlhumdev.2014.10.006.

Monnelly, V.J., Anblagan, D., Quigley, A., Cabez, M.B., Cooper, E.S., Mactier, H., Semple, S.I., Bastin, M.E., and Boardman, J.P. (2018). Prenatal methadone exposure is associated with altered neonatal brain development. Neuroimage Clin 18, 9-14. 10.1016/j.nicl.2017.12.033.

Mulkey, S.B., and Plessis, A.D. (2018). The Critical Role of the Central Autonomic Nervous System in Fetal-Neonatal Transition. Semin Pediatr Neurol 28, 29-37. 10.1016/j.spen.2018.05.004.

National Survey on Drug Use and Health ICPSR 34481-v3. Ann Arbor (MI): US Department of Health and Human Services, Substance Abuse and Mental Health Services Administration. Center for Behavioral Health Statistics and Quality; 2011.

Nematian, S.E., Mamillapalli, R., Kadakia, T.S., Majidi Zolbin, M., Moustafa, S., and Taylor, H.S. (2018). Systemic Inflammation Induced by microRNAs: Endometriosis-Derived Alterations in Circulating microRNA 125b-5p and Let-7b-5p Regulate Macrophage Cytokine Production. J Clin Endocrinol Metab 103, 64-74. 10.1210/jc.2017-01199.

Newman, A.I., Mauer-Vakil, D., Coo, H., Newton, L., Wilkerson, E., McKnight, S., and Brogly, S.B. (2020). Rooming-in for Infants at Risk for Neonatal Abstinence Syndrome: Outcomes 5 Years following Its Introduction as the Standard of Care at One Hospital. Am J Perinatol. 10.1055/s-0040-1719182.

O'Connor, A.B., Collett, A., Alto, W.A., and O'Brien, L.M. (2013). Breastfeeding rates and the relationship between breastfeeding and neonatal abstinence syndrome in women maintained on buprenorphine during pregnancy. J Midwifery Womens Health 58, 383-388. 10.1111/jmwh.12009.

O'Connor, A.B., O'Brien, L., Alto, W.A., and Wong, J. (2016). Does concurrent in utero exposure to buprenorphine and antidepressant medications influence the course of neonatal abstinence syndrome? J Matern Fetal Neonatal Med 29, 112-114. 10.3109/14767058.2014.987750.

Oei, J., and Lui, K. (2007). Management of the newborn infant affected by maternal opiates and other drugs of dependency. J Paediatr Child Health 43, 9-18. 10.1111/j.1440-1754.2007.00994.x.

Oji-Mmuo, C.N., Gardner, F.C., and Doheny, K.K. (2018). Heightened sympathetic arousal is demonstrated by skin conductance responsivity to auditory stimuli in a small cohort of neonates with opiate withdrawal. Brain Res Bull 138, 106-111. 10.1016/j.brainresbull.2017.06.007.

Patrick, S.W., Slaughter, J.C., Harrell, F.E., Jr., Martin, P.R., Hartmann, K., Dudley, J., Stratton, S., and Cooper, W.O. (2021). Development and Validation of a Model to Predict Neonatal Abstinence Syndrome. J Pediatr 229, 154-160 e156. 10.1016/j.jpeds.2020.10.030.

Rosenthal, R. (1994). Parametric Measures of Effect Size. In The handbook of research synthesis., (Russell Sage Foundation), pp. 231-244.

Salem, N.A., Mahnke, A.H., Wells, A.B., Tseng, A.M., Yevtushok, L., Zymak-Zakutnya, N., Wertlecki, W., Chambers, C.D., Miranda, R.C., and Collaborative Initiative on Fetal Alcohol Spectrum, D. (2020). Association between fetal sex and maternal plasma microRNA responses to prenatal alcohol exposure: evidence from a birth outcome-stratified cohort. Biol Sex Differ 11, 51. 10.1186/s13293-020-00327-2.

SAS Institute Inc. (2014). Chapter 60 The Logistic Procedure. SAS/STAT® 13.2 User's Guide. SAS Institute Inc.

Shah, J.S., Soon, P.S., and Marsh, D.J. (2016). Comparison of Methodologies to Detect Low Levels of Hemolysis in Serum for Accurate Assessment of Serum microRNAs. PLoS One 11, e0153200. 10.1371/journal.pone.0153200.

Shahjin, F., Guda, R.S., Schaal, V.L., Odegaard, K., Clark, A., Gowen, A., Xiao, P., Lisco, S.J., Pendyala, G., and Yelamanchili, S.V. (2019). Brain-Derived Extracellular Vesicle microRNA Signatures Associated with In Utero and Postnatal Oxycodone Exposure. Cells 9. 10.3390/cells9010021.

(56) References Cited

OTHER PUBLICATIONS

Staszewski, C.L., Garretto, D., Garry, E.T., Ly, V., Davis, J.A., and Herrera, K.M. (2020). Comparison of buprenorphine and methadone in the management of maternal opioid use disorder in full term pregnancies. J Perinat Med 48, 677-680. 10.1515/jpm-2020-0106.
Stover, M.W., and Davis, J.M. (2015). Opioids in pregnancy and neonatal abstinence syndrome. Semin Perinatol 39, 561-565. 10.1053/j.semperi.2015.08.013.
Toyama, K., Kiyosawa, N., Watanabe, K., and Ishizuka, H. (2017). Identification of Circulating miRNAs Differentially Regulated by Opioid Treatment. Int J Mol Sci 18. 10.3390/ijms18091991.
Tseng, A.M., Mahnke, A.H., Wells, A.B., Salem, N.A., Allan, A.M., Roberts, V.H., Newman, N., Walter, N.A., Kroenke, C.D., Grant, K.A., et al. (2019). Maternal circulating miRNAs that predict infant FASD outcomes influence placental maturation. Life Sci Alliance 2. 10.26508/Isa.201800252.
Vasan, V., Kitase, Y., Newville, J., Robinson, S., Gerner, G., Burton, V., and Jantzie, L. (2021). Neonatal opioid exposure: public health crisis and novel neuroinflammatory disease. Neural Regeneration Research 16, 430-432. 10.4103/1673-5374.293136.
Wachman, E.M., Hayes, M.J., Lester, B.M., Terrin, N., Brown, M.S., Nielsen, D.A., and Davis, J.M. (2014). Epigenetic variation in the mu-opioid receptor gene in infants with neonatal abstinence syndrome. J Pediatr 165, 472-478. 10.1016/j.jpeds.2014.05.040.
Wachman, E.M., Schiff, D.M., and Silverstein, M. (2018). Neonatal Abstinence Syndrome: Advances in Diagnosis and Treatment. JAMA 319, 1362-1374. 10.1001/jama.2018.2640.
Yang, F.Q., Zhang, J.Q., Jin, J.J., Yang, C.Y., Zhang, W.J., Zhang, H.M., Zheng, J.H., and Weng, Z.M. (2018). HOXA11-AS promotes the growth and invasion of renal cancer by sponging miR-146b-5p to upregulate MMP16 expression. J Cell Physiol 233, 9611-9619. 10.1002/jcp.26864.
Zelson, C., Rubio, E., and Wasserman, E. (1971). Neonatal narcotic addiction: 10 year observation. Pediatrics 48, 178-189.
National Academies of Sciences Engineering and Medicine (U.S.). Committee on Medication-Assisted Treatment for Opioid Use Disorder, Leshner, A.I., Mancher, M., National Academies of Sciences Engineering and Medicine (U.S.). Board on Health Sciences Policy., and National Academies of Sciences Engineering and Medicine (U.S.). Health and Medicine Division. (2019). Medications for opioid use disorder save lives (The National Academies Press).

* cited by examiner

FIGURE 1S

Supplementary Table S1: miRNA primers altered between panel versions

| miRNA | MIMAT | Analysis Status |
|---|---|---|
| hsa-miR-17-5p | MIMAT0000070 | Exclude |
| hsa-miR-26a-5p | MIMAT0000082 | Include |
| hsa-miR-27a-3p | MIMAT0000084 | Include |
| hsa-miR-30d-5p | MIMAT0000245 | Exclude |
| hsa-miR-181a-5p | MIMAT0000256 | Include |
| hsa-miR-223-3p | MIMAT0000280 | Include |
| hsa-miR-128-3p | MIMAT0000424 | Include |
| hsa-miR-132-3p | MIMAT0000426 | Include |
| hsa-miR-143-3p | MIMAT0000435 | Include |
| hsa-miR-126-5p | MIMAT0000444 | Include |
| hsa-miR-185-5p | MIMAT0000455 | Include |
| hsa-miR-186-5p | MIMAT0000456 | Include |
| hsa-miR-320a | MIMAT0000510 | Include |
| hsa-miR-99b-5p | MIMAT0000689 | Include |
| hsa-miR-361-5p | MIMAT0000703 | Include |
| hsa-miR-331-3p | MIMAT0000760 | Exclude |
| hsa-miR-339-5p | MIMAT0000764 | Include |
| hsa-miR-335-5p | MIMAT0000765 | Include |
| hsa-miR-133b | MIMAT0000770 | Include |
| hsa-miR-451a | MIMAT0001631 | Include |
| hsa-miR-485-3p | MIMAT0002176 | Include |
| hsa-miR-495-3p | MIMAT0002817 | Include |
| hsa-miR-574-3p | MIMAT0003239 | Exclude |
| hsa-miR-320b | MIMAT0005792 | Include |

FIGURE 3S

Supplementary Table S3: Expression and Eligibility Criteria[a] Performance, With and Without Stratification by Type of Maternal MOUD, for All Assessed miRNAs

| | | Need for pharmalogical treatment | | | | | | | | | | | | Prolonged Hospitalization… |
|---|---|---|---|---|---|---|---|---|---|---|---|---|---|---|
| | | All samples[1] | | | | Maternal methadone-exposed[2] | | | | Maternal buprenorpine-exposed[3] | | | | All samples[4]… |
| MIMAT | miRNA | Difference Mean[7] | Difference SD | Cohen's *d* | p-value[9] | Difference Mean[7] | Difference SD | Cohen's *d* | p-value[9] | Difference Mean[7] | Difference SD | Cohen's *d* | p-value[9] | Difference Mean[8] |
| MIMAT0000062 | hsa-let-7a-5p | -0.13 | 0.74 | -0.17 | 0.62 | 0.16 | 0.77 | 0.20 | 0.71 | -0.35 | 0.73 | -0.48 | 0.36 | -0.03 |
| MIMAT0000063 | hsa-let-7b-5p | -0.77 | 0.88 | -0.88 | 0.00 | -1.03 | 0.72 | -1.43 | 0.01 | -0.14 | 0.97 | -0.15 | 0.78 | -1.13 |
| MIMAT0000064 | hsa-let-7c-5p | -0.31 | 0.68 | -0.46 | 0.12 | -0.73 | 0.60 | -1.22 | 0.03 | -0.14 | 0.73 | -0.19 | 0.72 | -0.30 |
| MIMAT0000065 | hsa-let-7d-5p | -0.65 | 1.01 | -0.65 | 0.08 | -0.93 | 1.28 | -0.73 | 0.19 | -0.76 | 0.88 | -0.86 | 0.10 | -0.52 |
| MIMAT0000066 | hsa-let-7e-5p | -0.39 | 0.72 | -0.53 | 0.11 | -0.10 | 0.84 | -0.12 | 0.82 | -0.20 | 0.65 | -0.31 | 0.55 | -0.54 |
| MIMAT0000067 | hsa-let-7f-5p | -0.70 | 1.70 | -0.41 | 0.20 | -1.06 | 1.91 | -0.55 | 0.31 | 0.05 | 1.63 | 0.03 | 0.95 | -0.51 |
| MIMAT0000068 | hsa-miR-15a-5p | 0.26 | 1.20 | 0.22 | 0.50 | 0.27 | 1.51 | 0.18 | 0.74 | 0.09 | 1.06 | 0.08 | 0.87 | 0.53 |
| MIMAT0000069 | hsa-miR-16-5p | 0.34 | 0.72 | 0.47 | 0.13 | 0.70 | 0.64 | 1.09 | 0.05 | -0.07 | 0.71 | -0.10 | 0.85 | 0.22 |
| MIMAT0000072 | hsa-miR-18a-5p | 0.43 | 0.77 | 0.56 | 0.05 | 0.41 | 0.54 | 0.75 | 0.17 | 0.00 | 0.86 | 0.00 | 0.99 | 0.35 |
| MIMAT0000073 | hsa-miR-19a-3p | 0.17 | 0.69 | 0.25 | 0.45 | 0.06 | 0.75 | 0.08 | 0.88 | 0.07 | 0.67 | 0.10 | 0.85 | 0.07 |
| MIMAT0000074 | hsa-miR-19b-3p | 0.17 | 0.60 | 0.28 | 0.40 | 0.01 | 0.65 | 0.02 | 0.97 | 0.07 | 0.56 | 0.12 | 0.81 | 0.10 |
| MIMAT0000075 | hsa-miR-20a-5p | 0.24 | 0.67 | 0.35 | 0.26 | 0.28 | 0.65 | 0.42 | 0.43 | -0.07 | 0.68 | -0.10 | 0.84 | 0.15 |
| MIMAT0000076 | hsa-miR-21-5p | -0.27 | 0.59 | -0.47 | 0.08 | -0.32 | 0.46 | -0.69 | 0.21 | 0.16 | 0.63 | 0.25 | 0.62 | -0.43 |
| MIMAT0000077 | hsa-miR-22-3p | -0.20 | 0.93 | -0.22 | 0.56 | -0.59 | 1.25 | -0.47 | 0.38 | 0.16 | 0.69 | 0.24 | 0.65 | -0.25 |
| MIMAT0000078 | hsa-miR-23a-3p | -0.47 | 0.81 | -0.58 | 0.03 | -0.22 | 0.53 | -0.42 | 0.44 | -0.09 | 0.91 | -0.10 | 0.84 | -0.59 |
| MIMAT0000080 | hsa-miR-24-3p | -0.37 | 0.85 | -0.44 | 0.10 | 0.01 | 0.61 | 0.02 | 0.97 | -0.06 | 0.94 | -0.06 | 0.90 | -0.52 |
| MIMAT0000081 | hsa-miR-25-3p | 0.30 | 0.72 | 0.41 | 0.20 | 0.42 | 0.71 | 0.59 | 0.28 | -0.13 | 0.70 | -0.18 | 0.73 | 0.21 |
| MIMAT0000082 | hsa-miR-26a-5p | -0.03 | 0.60 | -0.05 | 0.86 | 0.22 | 0.59 | 0.38 | 0.48 | -0.15 | 0.62 | -0.24 | 0.64 | 0.16 |
| MIMAT0000083 | hsa-miR-26b-5p | -0.27 | 0.88 | -0.30 | 0.37 | -0.34 | 1.14 | -0.30 | 0.58 | -0.22 | 0.76 | -0.29 | 0.57 | -0.17 |
| MIMAT0000084 | hsa-miR-27a-3p | -0.36 | 0.82 | -0.44 | 0.11 | -0.38 | 0.54 | -0.69 | 0.21 | 0.15 | 0.94 | 0.16 | 0.76 | -0.51 |
| MIMAT0000085 | hsa-miR-28-5p | -1.38 | 2.78 | -0.50 | 0.19 | -1.27 | 3.71 | -0.34 | 0.52 | -1.98 | 2.20 | -0.90 | 0.09 | -1.55 |
| MIMAT0000086 | hsa-miR-29a-3p | -1.01 | 1.30 | -0.78 | 0.02 | -1.38 | 1.24 | -1.12 | 0.05 | 0.03 | 1.27 | 0.03 | 0.96 | -1.24 |
| MIMAT0000087 | hsa-miR-30a-5p | -0.73 | 0.91 | -0.80 | 0.03 | -1.18 | 1.10 | -1.07 | 0.06 | 0.09 | 0.69 | 0.13 | 0.80 | -0.98 |
| MIMAT0000090 | hsa-miR-32-5p | 0.01 | 0.94 | 0.01 | 0.98 | -0.12 | 1.17 | -0.11 | 0.84 | -0.11 | 0.84 | -0.13 | 0.80 | 0.04 |
| MIMAT0000091 | hsa-miR-33a-5p | -0.01 | 0.85 | -0.01 | 0.97 | -1.03 | 0.98 | -1.05 | 0.06 | 0.78 | 0.69 | 1.13 | 0.03 | 0.04 |
| MIMAT0000092 | hsa-miR-92a-3p | 0.25 | 0.57 | 0.44 | 0.10 | 0.25 | 0.42 | 0.61 | 0.27 | -0.01 | 0.62 | -0.02 | 0.97 | 0.19 |
| MIMAT0000093 | hsa-miR-93-5p | 0.11 | 0.89 | 0.13 | 0.73 | -0.13 | 1.18 | -0.11 | 0.84 | -0.22 | 0.70 | -0.31 | 0.54 | 0.06 |
| MIMAT0000097 | hsa-miR-99a-5p | -0.33 | 0.92 | -0.36 | 0.24 | -0.60 | 0.84 | -0.71 | 0.20 | 0.01 | 0.97 | 0.01 | 0.99 | -0.61 |
| MIMAT0000098 | hsa-miR-100-5p | -0.30 | 2.26 | -0.13 | 0.63 | 0.69 | 1.93 | 0.36 | 0.51 | -0.56 | 2.46 | -0.23 | 0.66 | -0.41 |
| MIMAT0000099 | hsa-miR-101-3p | -0.09 | 0.86 | -0.11 | 0.77 | -0.29 | 1.14 | -0.25 | 0.64 | -0.04 | 0.72 | -0.06 | 0.90 | -0.22 |
| MIMAT0000100 | hsa-miR-29b-3p | -0.80 | 1.87 | -0.43 | 0.16 | -0.49 | 1.77 | -0.28 | 0.61 | 0.13 | 1.93 | 0.07 | 0.90 | -0.70 |
| MIMAT0000101 | hsa-miR-103a-3p | 0.18 | 0.74 | 0.25 | 0.36 | 0.20 | 0.77 | 0.27 | 0.62 | -0.27 | 0.71 | -0.38 | 0.46 | 0.41 |
| MIMAT0000103 | hsa-miR-106a-5p | 0.31 | 0.69 | 0.45 | 0.14 | 0.54 | 0.56 | 0.97 | 0.08 | -0.15 | 0.72 | -0.21 | 0.68 | 0.26 |
| MIMAT0000104 | hsa-miR-107 | 0.01 | 0.86 | 0.02 | 0.96 | -0.32 | 1.08 | -0.29 | 0.59 | -0.26 | 0.73 | -0.36 | 0.49 | 0.21 |

FIGURE 3S Cont'd

| | | | | | | | | | | | | | | |
|---|---|---|---|---|---|---|---|---|---|---|---|---|---|---|
| MIMAT0000222 | hsa-miR-192-5p | 0.19 | 0.72 | 0.26 | 0.39 | -0.06 | 0.71 | -0.09 | 0.87 | 0.25 | 0.72 | 0.35 | 0.50 | 0.09 |
| MIMAT0000227 | hsa-miR-197-3p | 0.30 | 0.94 | 0.32 | 0.28 | 0.33 | 0.77 | 0.43 | 0.43 | 0.18 | 1.06 | 0.17 | 0.75 | 0.45 |
| MIMAT0000231 | hsa-miR-199a-5p | -0.43 | 1.41 | -0.30 | 0.39 | -1.63 | 1.75 | -0.93 | 0.09 | 0.26 | 1.09 | 0.24 | 0.65 | -0.37 |
| MIMAT0000232 | hsa-miR-199a-3p | -0.02 | 0.81 | -0.03 | 0.93 | -0.48 | 0.82 | -0.58 | 0.28 | 0.23 | 0.83 | 0.28 | 0.59 | -0.10 |
| MIMAT0000243 | hsa-miR-148a-3p | 0.09 | 0.67 | 0.14 | 0.72 | -0.42 | 0.98 | -0.43 | 0.42 | 0.37 | 0.44 | 0.84 | 0.11 | -0.05 |
| MIMAT0000244 | hsa-miR-30c-5p | -0.28 | 0.50 | -0.55 | 0.05 | -0.40 | 0.46 | -0.88 | 0.11 | -0.12 | 0.55 | -0.21 | 0.68 | -0.31 |
| MIMAT0000250 | hsa-miR-139-5p | 0.33 | 1.53 | 0.21 | 0.49 | 0.54 | 1.57 | 0.35 | 0.52 | -0.06 | 1.59 | -0.04 | 0.94 | 0.23 |
| MIMAT0000252 | hsa-miR-7-5p | 0.31 | 0.89 | 0.34 | 0.24 | 0.19 | 1.01 | 0.19 | 0.72 | -0.31 | 0.81 | -0.39 | 0.45 | 0.40 |
| MIMAT0000254 | hsa-miR-10b-5p | -0.25 | 0.92 | -0.28 | 0.30 | -0.37 | 0.89 | -0.42 | 0.44 | 0.16 | 0.93 | 0.18 | 0.73 | -0.59 |
| MIMAT0000255 | hsa-miR-34a-5p | -0.21 | 1.23 | -0.17 | 0.47 | 0.03 | 1.03 | 0.02 | 0.96 | 0.88 | 1.22 | 0.73 | 0.16 | -0.55 |
| MIMAT0000256 | hsa-miR-181a-5p | 0.00 | 0.81 | 0.00 | 1.00 | 0.06 | 0.89 | 0.07 | 0.89 | -0.03 | 0.80 | -0.03 | 0.95 | 0.23 |
| MIMAT0000266 | hsa-miR-205-5p | -0.03 | 3.32 | -0.01 | 0.97 | 1.41 | 3.94 | 0.36 | 0.51 | -0.27 | 2.91 | -0.09 | 0.86 | -0.67 |
| MIMAT0000267 | hsa-miR-210-3p | -0.19 | 0.79 | -0.24 | 0.55 | -0.31 | 1.16 | -0.27 | 0.61 | -0.17 | 0.56 | -0.30 | 0.56 | -0.25 |
| MIMAT0000272 | hsa-miR-215-5p | 0.30 | 1.03 | 0.29 | 0.29 | 0.11 | 0.84 | 0.13 | 0.81 | 0.04 | 1.11 | 0.04 | 0.94 | 0.33 |
| MIMAT0000278 | hsa-miR-221-3p | 0.07 | 0.79 | 0.09 | 0.79 | 0.02 | 0.92 | 0.02 | 0.97 | 0.30 | 0.75 | 0.40 | 0.44 | 0.18 |
| MIMAT0000279 | hsa-miR-222-3p | -0.21 | 0.71 | -0.29 | 0.28 | 0.02 | 0.72 | 0.03 | 0.96 | -0.13 | 0.70 | -0.18 | 0.73 | -0.23 |
| MIMAT0000280 | hsa-miR-223-3p | -0.02 | 0.75 | -0.02 | 0.95 | 0.11 | 0.82 | 0.13 | 0.80 | -0.31 | 0.72 | -0.44 | 0.40 | 0.18 |
| MIMAT0000414 | hsa-let-7g-5p | 0.06 | 0.71 | 0.09 | 0.74 | 0.26 | 0.65 | 0.39 | 0.46 | -0.36 | 0.74 | -0.49 | 0.34 | 0.26 |
| MIMAT0000415 | hsa-let-7i-5p | -0.12 | 0.47 | -0.25 | 0.38 | -0.13 | 0.49 | -0.27 | 0.62 | -0.14 | 0.47 | -0.30 | 0.56 | -0.01 |
| MIMAT0000417 | hsa-miR-15b-5p | 0.01 | 0.81 | 0.01 | 0.98 | -0.44 | 1.19 | -0.37 | 0.50 | -0.02 | 0.53 | -0.04 | 0.93 | -0.05 |
| MIMAT0000418 | hsa-miR-23b-3p | -0.40 | 0.77 | -0.52 | 0.05 | -0.39 | 0.54 | -0.73 | 0.18 | 0.07 | 0.85 | 0.08 | 0.87 | -0.51 |
| MIMAT0000419 | hsa-miR-27b-3p | -0.34 | 0.70 | -0.49 | 0.05 | -0.44 | 0.46 | -0.96 | 0.09 | 0.38 | 0.75 | 0.51 | 0.32 | -0.54 |
| MIMAT0000420 | hsa-miR-30b-5p | -0.33 | 1.22 | -0.27 | 0.27 | -0.24 | 0.77 | -0.32 | 0.56 | -0.15 | 1.46 | -0.10 | 0.85 | -0.28 |
| MIMAT0000421 | hsa-miR-122-5p | -0.59 | 1.93 | -0.31 | 0.37 | -1.65 | 2.03 | -0.81 | 0.14 | 0.70 | 1.90 | 0.37 | 0.48 | -0.54 |
| MIMAT0000423 | hsa-miR-125b-5p | -0.40 | 1.15 | -0.35 | 0.19 | -0.25 | 0.89 | -0.29 | 0.59 | 0.30 | 1.26 | 0.24 | 0.65 | -0.67 |
| MIMAT0000424 | hsa-miR-128-3p | 0.41 | 0.64 | 0.64 | 0.01 | 0.28 | 0.74 | 0.39 | 0.47 | 0.17 | 0.59 | 0.29 | 0.57 | 0.54 |
| MIMAT0000425 | hsa-miR-130a-3p | 0.08 | 0.68 | 0.12 | 0.77 | -0.38 | 1.00 | -0.37 | 0.49 | 0.34 | 0.40 | 0.84 | 0.11 | -0.04 |
| MIMAT0000426 | hsa-miR-132-3p | -0.12 | 1.17 | -0.10 | 0.73 | -0.63 | 1.26 | -0.50 | 0.36 | 0.42 | 1.17 | 0.36 | 0.49 | -0.18 |
| MIMAT0000427 | hsa-miR-133a-3p | 0.45 | 4.47 | 0.10 | 0.70 | -1.41 | 4.91 | -0.29 | 0.59 | 0.74 | 4.24 | 0.17 | 0.74 | 0.12 |
| MIMAT0000431 | hsa-miR-140-5p | 0.19 | 0.58 | 0.33 | 0.24 | -0.03 | 0.58 | -0.05 | 0.92 | 0.43 | 0.60 | 0.71 | 0.17 | 0.12 |
| MIMAT0000432 | hsa-miR-141-3p | -0.76 | 2.70 | -0.28 | 0.32 | -0.18 | 2.19 | -0.08 | 0.88 | -1.08 | 3.05 | -0.36 | 0.49 | -0.23 |
| MIMAT0000433 | hsa-miR-142-5p | -0.13 | 0.85 | -0.15 | 0.70 | -0.66 | 1.17 | -0.57 | 0.30 | 0.14 | 0.64 | 0.22 | 0.67 | 0.02 |
| MIMAT0000434 | hsa-miR-142-3p | -0.27 | 0.84 | -0.32 | 0.23 | -0.49 | 0.71 | -0.70 | 0.20 | -0.33 | 0.93 | -0.35 | 0.49 | -0.11 |
| MIMAT0000435 | hsa-miR-143-3p | -0.15 | 1.47 | -0.10 | 0.72 | -1.27 | 1.52 | -0.84 | 0.13 | 1.02 | 1.38 | 0.73 | 0.16 | -0.37 |
| MIMAT0000436 | hsa-miR-144-3p | -0.06 | 1.12 | -0.06 | 0.87 | -0.49 | 1.34 | -0.37 | 0.50 | -0.13 | 1.02 | -0.13 | 0.80 | -0.06 |
| MIMAT0000437 | hsa-miR-145-5p | -0.14 | 1.24 | -0.12 | 0.66 | -0.63 | 1.32 | -0.48 | 0.38 | 0.29 | 1.23 | 0.23 | 0.65 | -0.28 |
| MIMAT0000438 | hsa-miR-152-3p | 0.25 | 0.46 | 0.53 | 0.02 | 0.29 | 0.29 | 1.02 | 0.07 | 0.23 | 0.54 | 0.42 | 0.42 | 0.19 |
| MIMAT0000440 | hsa-miR-191-5p | 0.08 | 0.56 | 0.14 | 0.66 | 0.24 | 0.52 | 0.46 | 0.39 | -0.37 | 0.57 | -0.65 | 0.21 | 0.30 |
| MIMAT0000443 | hsa-miR-125a-5p | -0.73 | 1.24 | -0.59 | 0.03 | -0.92 | 0.85 | -1.08 | 0.05 | 0.01 | 1.41 | 0.01 | 0.99 | -0.86 |
| MIMAT0000444 | hsa-miR-126-5p | 0.09 | 0.99 | 0.09 | 0.76 | -0.15 | 1.05 | -0.14 | 0.79 | 0.58 | 0.96 | 0.60 | 0.25 | -0.03 |
| MIMAT0000445 | hsa-miR-126-3p | -0.18 | 0.67 | -0.27 | 0.27 | -0.55 | 0.46 | -1.21 | 0.03 | 0.21 | 0.77 | 0.28 | 0.59 | -0.22 |
| MIMAT0000446 | hsa-miR-127-3p | 0.32 | 0.95 | 0.33 | 0.24 | -0.30 | 0.94 | -0.32 | 0.55 | 0.46 | 0.98 | 0.47 | 0.37 | 0.51 |

FIGURE 3S Cont'd

| | | | | | | | | | | | | | | |
|---|---|---|---|---|---|---|---|---|---|---|---|---|---|---|
| MIMAT0000448 | hsa-miR-136-5p | -0.12 | 1.11 | -0.11 | 0.74 | -1.32 | 1.16 | -1.13 | 0.05 | 0.52 | 1.02 | 0.51 | 0.33 | -0.09 |
| MIMAT0000449 | hsa-miR-146a-5p | 0.24 | 0.83 | 0.30 | 0.35 | 0.03 | 0.76 | 0.04 | 0.94 | 0.39 | 0.89 | 0.44 | 0.40 | 0.48 |
| MIMAT0000451 | hsa-miR-150-5p | -0.18 | 0.79 | -0.23 | 0.40 | -0.03 | 0.61 | -0.04 | 0.93 | -0.47 | 0.89 | -0.53 | 0.31 | -0.03 |
| MIMAT0000452 | hsa-miR-154-5p | 0.62 | 0.85 | 0.72 | 0.00 | 0.34 | 0.77 | 0.44 | 0.41 | 0.55 | 0.93 | 0.59 | 0.26 | 0.60 |
| MIMAT0000455 | hsa-miR-185-5p | 0.05 | 0.89 | 0.05 | 0.88 | -0.03 | 1.06 | -0.03 | 0.96 | -0.28 | 0.80 | -0.35 | 0.50 | 0.03 |
| MIMAT0000456 | hsa-miR-186-5p | 0.36 | 0.72 | 0.50 | 0.09 | 0.75 | 0.73 | 1.03 | 0.07 | 0.04 | 0.73 | 0.05 | 0.92 | 0.37 |
| MIMAT0000460 | hsa-miR-194-5p | -0.05 | 0.71 | -0.08 | 0.81 | -0.28 | 0.86 | -0.32 | 0.55 | 0.17 | 0.63 | 0.27 | 0.60 | 0.01 |
| MIMAT0000461 | hsa-miR-195-5p | -0.24 | 1.31 | -0.18 | 0.52 | -1.20 | 1.34 | -0.90 | 0.11 | 0.63 | 1.29 | 0.49 | 0.35 | -0.45 |
| MIMAT0000617 | hsa-miR-200c-3p | -0.33 | 2.38 | -0.14 | 0.58 | 0.34 | 1.67 | 0.21 | 0.70 | -0.55 | 2.76 | -0.20 | 0.70 | -0.29 |
| MIMAT0000646 | hsa-miR-155-5p | -0.54 | 2.53 | -0.21 | 0.51 | 1.17 | 1.89 | 0.62 | 0.26 | -3.01 | 2.71 | -1.11 | 0.04 | -0.04 |
| MIMAT0000680 | hsa-miR-106b-5p | 0.01 | 0.72 | 0.01 | 0.97 | -0.07 | 0.78 | -0.10 | 0.86 | -0.13 | 0.70 | -0.18 | 0.72 | 0.04 |
| MIMAT0000681 | hsa-miR-29c-3p | -0.62 | 1.11 | -0.56 | 0.07 | -0.86 | 0.99 | -0.87 | 0.12 | 0.36 | 1.11 | 0.32 | 0.53 | -0.75 |
| MIMAT0000688 | hsa-miR-301a-3p | -0.11 | 1.14 | -0.10 | 0.77 | -0.33 | 1.24 | -0.27 | 0.62 | -0.69 | 1.10 | -0.63 | 0.23 | 0.08 |
| MIMAT0000689 | hsa-miR-99b-5p | -0.62 | 1.58 | -0.39 | 0.21 | -1.28 | 1.39 | -0.92 | 0.10 | -0.22 | 1.73 | -0.13 | 0.81 | -0.80 |
| MIMAT0000691 | hsa-miR-130b-3p | -0.42 | 1.22 | -0.35 | 0.41 | -0.54 | 1.35 | -0.40 | 0.46 | -0.20 | 1.14 | -0.18 | 0.73 | -0.57 |
| MIMAT0000692 | hsa-miR-30e-5p | 0.25 | 0.56 | 0.45 | 0.11 | 0.32 | 0.58 | 0.54 | 0.32 | 0.09 | 0.57 | 0.15 | 0.77 | 0.17 |
| MIMAT0000693 | hsa-miR-30e-3p | -0.12 | 0.92 | -0.13 | 0.65 | -0.40 | 0.75 | -0.53 | 0.33 | 0.44 | 1.01 | 0.43 | 0.40 | -0.04 |
| MIMAT0000703 | hsa-miR-361-5p | -0.05 | 0.54 | -0.09 | 0.78 | -0.04 | 0.70 | -0.06 | 0.91 | 0.03 | 0.46 | 0.07 | 0.90 | -0.16 |
| MIMAT0000707 | hsa-miR-363-3p | -0.09 | 0.79 | -0.11 | 0.75 | -0.47 | 1.02 | -0.46 | 0.39 | 0.08 | 0.66 | 0.13 | 0.81 | -0.14 |
| MIMAT0000710 | hsa-miR-365a-3p | -0.91 | 1.50 | -0.61 | 0.04 | -1.69 | 1.08 | -1.56 | 0.01 | 0.37 | 1.62 | 0.23 | 0.66 | -1.21 |
| MIMAT0000720 | hsa-miR-376c-3p | 0.43 | 1.04 | 0.41 | 0.10 | -0.13 | 0.70 | -0.18 | 0.74 | 0.66 | 1.21 | 0.54 | 0.30 | 0.52 |
| MIMAT0000727 | hsa-miR-374a-5p | -0.32 | 1.14 | -0.28 | 0.43 | -0.73 | 1.55 | -0.47 | 0.38 | -0.12 | 0.91 | -0.13 | 0.80 | -0.21 |
| MIMAT0000729 | hsa-miR-376a-3p | 0.11 | 0.93 | 0.12 | 0.76 | -0.92 | 1.13 | -0.82 | 0.14 | 0.53 | 0.75 | 0.70 | 0.18 | 0.15 |
| MIMAT0000732 | hsa-miR-378a-3p | -0.16 | 0.77 | -0.20 | 0.59 | -0.40 | 1.13 | -0.36 | 0.51 | -0.27 | 0.51 | -0.53 | 0.31 | -0.22 |
| MIMAT0000737 | hsa-miR-382-5p | 0.59 | 0.95 | 0.63 | 0.05 | 0.26 | 0.93 | 0.28 | 0.61 | 0.83 | 0.99 | 0.84 | 0.11 | 0.60 |
| MIMAT0000752 | hsa-miR-328-3p | -0.17 | 0.75 | -0.23 | 0.50 | -0.49 | 0.95 | -0.52 | 0.34 | 0.42 | 0.63 | 0.66 | 0.20 | -0.49 |
| MIMAT0000753 | hsa-miR-342-3p | 0.10 | 0.64 | 0.16 | 0.65 | 0.64 | 0.69 | 0.93 | 0.09 | -0.26 | 0.59 | -0.43 | 0.40 | 0.14 |
| MIMAT0000756 | hsa-miR-326 | 1.67 | 5.15 | 0.32 | 0.20 | 0.70 | 5.08 | 0.14 | 0.80 | 5.34 | 5.23 | 1.02 | 0.05 | 1.92 |
| MIMAT0000757 | hsa-miR-151a-3p | 0.03 | 0.64 | 0.05 | 0.90 | -0.12 | 0.94 | -0.13 | 0.81 | 0.14 | 0.44 | 0.33 | 0.53 | 0.06 |
| MIMAT0000759 | hsa-miR-148b-3p | 0.14 | 0.60 | 0.23 | 0.46 | 0.24 | 0.62 | 0.39 | 0.47 | -0.12 | 0.61 | -0.20 | 0.71 | 0.09 |
| MIMAT0000761 | hsa-miR-324-5p | 0.99 | 2.30 | 0.43 | 0.04 | 1.14 | 1.98 | 0.58 | 0.29 | -0.05 | 2.51 | -0.02 | 0.97 | 0.11 |
| MIMAT0000762 | hsa-miR-324-3p | 0.23 | 0.98 | 0.23 | 0.34 | 1.55 | 1.38 | 1.12 | 0.05 | -0.43 | 0.54 | -0.80 | 0.13 | 0.23 |
| MIMAT0000763 | hsa-miR-338-3p | 0.08 | 1.08 | 0.07 | 0.82 | -1.05 | 1.03 | -1.02 | 0.07 | 0.86 | 1.06 | 0.81 | 0.12 | 0.38 |
| MIMAT0000764 | hsa-miR-339-5p | 0.13 | 0.82 | 0.15 | 0.60 | -0.46 | 0.81 | -0.57 | 0.29 | 0.37 | 0.82 | 0.45 | 0.38 | 0.15 |
| MIMAT0000765 | hsa-miR-335-5p | -0.08 | 0.91 | -0.09 | 0.75 | -0.23 | 0.89 | -0.26 | 0.63 | 0.36 | 0.92 | 0.39 | 0.45 | -0.14 |
| MIMAT0000770 | hsa-miR-133b | -0.92 | 1.81 | -0.51 | 0.08 | -2.18 | 1.79 | -1.22 | 0.03 | -0.52 | 1.76 | -0.29 | 0.57 | -0.89 |
| MIMAT0001340 | hsa-miR-423-3p | 0.26 | 0.49 | 0.53 | 0.05 | 0.36 | 0.45 | 0.79 | 0.15 | 0.15 | 0.52 | 0.29 | 0.57 | 0.27 |
| MIMAT0001341 | hsa-miR-424-5p | -0.38 | 1.20 | -0.32 | 0.28 | -0.45 | 0.97 | -0.46 | 0.39 | 0.39 | 1.30 | 0.30 | 0.57 | -0.48 |
| MIMAT0001343 | hsa-miR-425-3p | 0.33 | 0.90 | 0.37 | 0.19 | 0.61 | 0.96 | 0.64 | 0.24 | -0.44 | 0.85 | -0.51 | 0.33 | 0.46 |
| MIMAT0001412 | hsa-miR-18b-5p | 0.53 | 0.74 | 0.71 | 0.02 | 0.48 | 0.64 | 0.75 | 0.17 | -0.05 | 0.77 | -0.06 | 0.90 | 0.64 |
| MIMAT0001413 | hsa-miR-20b-5p | -0.71 | 1.46 | -0.48 | 0.22 | -1.29 | 1.96 | -0.66 | 0.23 | -0.21 | 1.14 | -0.19 | 0.72 | -0.87 |
| MIMAT0001631 | hsa-miR-451a | 0.03 | 0.90 | 0.03 | 0.93 | -0.07 | 1.16 | -0.06 | 0.91 | 0.15 | 0.77 | 0.20 | 0.70 | -0.12 |

FIGURE 3S Cont'd

| | | | | | | | | | | | | | | |
|---|---|---|---|---|---|---|---|---|---|---|---|---|---|---|
| MIMAT0001639 | hsa-miR-409-3p | 0.49 | 1.04 | 0.47 | 0.13 | 0.02 | 1.06 | 0.02 | 0.97 | 0.42 | 1.06 | 0.40 | 0.44 | 0.77 |
| MIMAT0002174 | hsa-miR-484 | 0.39 | 0.54 | 0.72 | 0.02 | 0.35 | 0.45 | 0.76 | 0.17 | 0.01 | 0.54 | 0.02 | 0.97 | 0.40 |
| MIMAT0002176 | hsa-miR-485-3p | -0.01 | 1.24 | -0.01 | 0.98 | -1.07 | 1.27 | -0.84 | 0.13 | 0.17 | 1.20 | 0.14 | 0.78 | 0.33 |
| MIMAT0002177 | hsa-miR-486-5p | 0.35 | 0.82 | 0.43 | 0.17 | 0.76 | 0.72 | 1.05 | 0.06 | -0.21 | 0.83 | -0.25 | 0.62 | 0.20 |
| MIMAT0002809 | hsa-miR-146b-5p | -0.75 | 0.93 | -0.80 | 0.01 | -1.85 | 0.96 | -1.94 | 0.00 | 0.09 | 0.85 | 0.10 | 0.85 | -0.47 |
| MIMAT0002817 | hsa-miR-495-3p | 0.46 | 1.01 | 0.46 | 0.07 | 0.69 | 1.04 | 0.66 | 0.23 | 0.12 | 1.00 | 0.12 | 0.81 | 0.61 |
| MIMAT0002820 | hsa-miR-497-5p | 0.28 | 2.24 | 0.12 | 0.62 | -0.32 | 1.64 | -0.20 | 0.71 | 0.80 | 2.60 | 0.31 | 0.55 | 0.20 |
| MIMAT0002876 | hsa-miR-505-3p | 0.13 | 0.76 | 0.18 | 0.60 | -0.22 | 0.51 | -0.44 | 0.42 | -0.52 | 0.80 | -0.65 | 0.22 | 0.38 |
| MIMAT0002888 | hsa-miR-532-5p | 0.33 | 0.71 | 0.46 | 0.12 | 0.59 | 0.84 | 0.70 | 0.20 | -0.15 | 0.63 | -0.25 | 0.63 | 0.39 |
| MIMAT0003218 | hsa-miR-92b-3p | 0.19 | 1.96 | 0.10 | 0.65 | 0.97 | 3.12 | 0.31 | 0.56 | 0.55 | 0.92 | 0.60 | 0.25 | -0.12 |
| MIMAT0003249 | hsa-miR-584-5p | 0.54 | 0.75 | 0.73 | 0.01 | 0.35 | 0.76 | 0.46 | 0.39 | 0.43 | 0.77 | 0.56 | 0.28 | 0.48 |
| MIMAT0003258 | hsa-miR-590-5p | -0.18 | 0.88 | -0.21 | 0.53 | -0.60 | 0.83 | -0.73 | 0.19 | -0.08 | 0.91 | -0.09 | 0.86 | -0.41 |
| MIMAT0003322 | hsa-miR-652-3p | 0.40 | 0.58 | 0.70 | 0.01 | 0.51 | 0.45 | 1.11 | 0.05 | 0.21 | 0.65 | 0.33 | 0.53 | 0.50 |
| MIMAT0003338 | hsa-miR-660-5p | 0.18 | 0.52 | 0.34 | 0.28 | 0.49 | 0.52 | 0.94 | 0.09 | 0.06 | 0.53 | 0.12 | 0.81 | 0.00 |
| MIMAT0003339 | hsa-miR-421 | 0.91 | 0.86 | 1.06 | 0.00 | 1.21 | 0.72 | 1.68 | 0.01 | 1.05 | 0.94 | 1.12 | 0.04 | 0.86 |
| MIMAT0003393 | hsa-miR-425-5p | 0.21 | 0.44 | 0.48 | 0.13 | 0.12 | 0.47 | 0.25 | 0.64 | 0.06 | 0.44 | 0.13 | 0.81 | 0.19 |
| MIMAT0003885 | hsa-miR-454-3p | -0.78 | 1.86 | -0.42 | 0.23 | -1.38 | 2.04 | -0.68 | 0.22 | -1.70 | 1.75 | -0.97 | 0.07 | -0.43 |
| MIMAT0003888 | hsa-miR-766-3p | 0.80 | 4.38 | 0.18 | 0.48 | 0.55 | 5.07 | 0.11 | 0.84 | 1.37 | 4.14 | 0.33 | 0.52 | 0.86 |
| MIMAT0004482 | hsa-let-7b-3p | -0.61 | 3.94 | -0.16 | 0.62 | 0.68 | 4.68 | 0.14 | 0.79 | -1.57 | 3.65 | -0.43 | 0.41 | 1.13 |
| MIMAT0004484 | hsa-let-7d-3p | 0.25 | 0.75 | 0.33 | 0.34 | 0.49 | 0.87 | 0.57 | 0.29 | 0.22 | 0.70 | 0.32 | 0.54 | 0.29 |
| MIMAT0004495 | hsa-miR-22-5p | -0.69 | 2.95 | -0.23 | 0.52 | -1.52 | 3.36 | -0.45 | 0.40 | -0.91 | 2.80 | -0.32 | 0.53 | -1.24 |
| MIMAT0004502 | hsa-miR-28-3p | -0.83 | 2.58 | -0.32 | 0.38 | -1.80 | 3.35 | -0.54 | 0.32 | 0.94 | 2.12 | 0.44 | 0.39 | -0.99 |
| MIMAT0004509 | hsa-miR-93-3p | -0.01 | 1.46 | -0.01 | 0.99 | 0.85 | 1.89 | 0.45 | 0.40 | -1.13 | 1.12 | -1.01 | 0.06 | -0.08 |
| MIMAT0004518 | hsa-miR-16-2-3p | -0.07 | 1.04 | -0.07 | 0.86 | -0.62 | 1.34 | -0.46 | 0.39 | -0.19 | 0.87 | -0.21 | 0.68 | -0.15 |
| MIMAT0004553 | hsa-miR-7-1-3p | -0.07 | 3.33 | -0.02 | 0.94 | 1.70 | 3.39 | 0.50 | 0.36 | 1.29 | 3.25 | 0.40 | 0.44 | -1.16 |
| MIMAT0004570 | hsa-miR-223-5p | -1.06 | 2.02 | -0.52 | 0.10 | -1.14 | 2.07 | -0.55 | 0.31 | -2.39 | 2.01 | -1.19 | 0.03 | -0.02 |
| MIMAT0004586 | hsa-miR-15b-3p | 0.14 | 0.85 | 0.16 | 0.58 | 0.29 | 0.85 | 0.34 | 0.53 | -0.33 | 0.86 | -0.39 | 0.45 | 0.23 |
| MIMAT0004597 | hsa-miR-140-3p | 0.20 | 0.52 | 0.38 | 0.25 | 0.20 | 0.59 | 0.35 | 0.52 | 0.30 | 0.48 | 0.62 | 0.23 | 0.08 |
| MIMAT0004600 | hsa-miR-144-5p | -0.01 | 0.92 | -0.01 | 0.98 | -0.03 | 0.63 | -0.04 | 0.93 | -0.69 | 0.98 | -0.70 | 0.18 | 0.23 |
| MIMAT0004606 | hsa-miR-136-3p | 0.26 | 1.14 | 0.23 | 0.45 | -0.71 | 1.20 | -0.59 | 0.28 | 1.19 | 1.06 | 1.13 | 0.03 | 0.03 |
| MIMAT0004614 | hsa-miR-193a-5p | -0.18 | 1.06 | -0.17 | 0.61 | -0.63 | 1.03 | -0.61 | 0.26 | -0.02 | 1.08 | -0.02 | 0.97 | -0.29 |
| MIMAT0004672 | hsa-miR-106b-3p | 0.18 | 1.11 | 0.16 | 0.58 | -0.35 | 1.07 | -0.32 | 0.55 | 0.06 | 1.15 | 0.05 | 0.92 | 0.30 |
| MIMAT0004683 | hsa-miR-362-3p | 0.92 | 1.62 | 0.57 | 0.01 | 2.28 | 1.49 | 1.53 | 0.01 | 0.52 | 1.68 | 0.31 | 0.55 | 1.19 |
| MIMAT0004697 | hsa-miR-151a-5p | -0.13 | 0.36 | -0.36 | 0.26 | -0.07 | 0.37 | -0.18 | 0.74 | 0.12 | 0.33 | 0.37 | 0.47 | -0.15 |
| MIMAT0004702 | hsa-miR-339-3p | -1.18 | 3.06 | -0.39 | 0.28 | -0.70 | 3.00 | -0.23 | 0.66 | -2.84 | 3.17 | -0.89 | 0.09 | -0.45 |
| MIMAT0004748 | hsa-miR-423-5p | 0.28 | 0.43 | 0.65 | 0.03 | 0.57 | 0.44 | 1.28 | 0.03 | -0.03 | 0.42 | -0.08 | 0.87 | 0.25 |
| MIMAT0004761 | hsa-miR-483-5p | -0.25 | 1.22 | -0.20 | 0.51 | -0.80 | 1.13 | -0.71 | 0.20 | 0.89 | 1.24 | 0.72 | 0.17 | -0.33 |
| MIMAT0004774 | hsa-miR-501-3p | 0.81 | 2.12 | 0.38 | 0.18 | 1.35 | 2.50 | 0.54 | 0.32 | 0.87 | 1.98 | 0.44 | 0.40 | 0.72 |
| MIMAT0004775 | hsa-miR-502-3p | 0.00 | 0.94 | 0.00 | 1.00 | -0.24 | 1.26 | -0.19 | 0.73 | 0.23 | 0.76 | 0.30 | 0.56 | -0.24 |
| MIMAT0004780 | hsa-miR-532-3p | -0.15 | 0.88 | -0.17 | 0.63 | 0.49 | 0.62 | 0.78 | 0.15 | -0.84 | 0.95 | -0.88 | 0.09 | -0.33 |
| MIMAT0004810 | hsa-miR-629-5p | 0.77 | 1.29 | 0.59 | 0.05 | 1.14 | 0.91 | 1.26 | 0.03 | 0.64 | 1.44 | 0.44 | 0.39 | 0.77 |
| MIMAT0004911 | hsa-miR-874-3p | -0.10 | 3.08 | -0.03 | 0.91 | 1.11 | 4.30 | 0.26 | 0.63 | 0.52 | 2.22 | 0.24 | 0.65 | -0.27 |

FIGURE 3S Cont'd

| | | | | | | | | | | | | | | |
|---|---|---|---|---|---|---|---|---|---|---|---|---|---|---|
| MIMAT0004949 | hsa-miR-877-5p | -1.73 | 4.81 | -0.36 | 0.27 | -2.88 | 4.99 | -0.58 | 0.29 | -0.23 | 4.89 | -0.05 | 0.93 | -1.28 |
| MIMAT0004954 | hsa-miR-543 | 1.30 | 3.18 | 0.41 | 0.04 | 2.78 | 3.15 | 0.88 | 0.11 | 0.96 | 3.29 | 0.29 | 0.57 | 1.23 |
| MIMAT0004955 | hsa-miR-374b-5p | -0.04 | 0.87 | -0.04 | 0.88 | -0.14 | 1.10 | -0.12 | 0.82 | 0.11 | 0.76 | 0.14 | 0.78 | 0.06 |
| MIMAT0005792 | hsa-miR-320b | 0.04 | 0.51 | 0.07 | 0.80 | 0.44 | 0.45 | 0.99 | 0.08 | -0.19 | 0.54 | -0.34 | 0.51 | -0.06 |
| MIMAT0005793 | hsa-miR-320c | -0.22 | 0.67 | -0.33 | 0.36 | -0.52 | 0.85 | -0.61 | 0.26 | 0.05 | 0.57 | 0.08 | 0.88 | -0.35 |
| MIMAT0005911 | hsa-miR-1260a | -0.51 | 1.86 | -0.27 | 0.32 | -0.01 | 1.41 | -0.01 | 0.99 | -0.69 | 2.14 | -0.32 | 0.54 | -0.46 |
| MIMAT0006764 | hsa-miR-320d | 0.27 | 0.54 | 0.50 | 0.08 | 0.48 | 0.61 | 0.79 | 0.15 | 0.33 | 0.52 | 0.64 | 0.22 | 0.19 |
| MIMAT0010133 | hsa-miR-2110 | -0.01 | 3.34 | 0.00 | 0.99 | 0.49 | 3.25 | 0.15 | 0.78 | -0.03 | 3.46 | -0.01 | 0.99 | -0.11 |

[a] Eligibility criteria for predictive models: $p < 0.10$ and $d > 0.40$ for mean difference in miRNA expression

[1] *Not-Pharmacologically-Treated* n = 41, *Pharmacologically-Treated* n = 17

[2] *Not-Pharmacologically-Treated* n = 10, *Pharmacologically-Treated* n = 11

[3] *Not-Pharmacologically-Treated* n = 31, *Pharmacologically-Treated* n = 6

[4] *Length of Stay < 14 days* n = 43, *Length of Stay ≥ 14 days* n = 15

[5] *Length of Stay < 14 days* n = 10, *Length of Stay ≥ 14 days* n = 11

[6] *Length of Stay < 14 days* n = 33, *Length of Stay ≥ 14 days* n = 4

[7] ΔΔCT $[(-\Delta CT_{Pharmacologically\text{-}Treated}) - (-\Delta CT_{Not\text{-}Pharmacologically\text{-}Treated})]$; 1 ΔΔCT approximates a two-fold change in expression

[8] ΔΔCT $[(-\Delta CT_{LOS \geq 14\ days}) - (-\Delta CT_{LOS < 14\ days})]$; 1 ΔΔCT approximates a two-fold change in expression

[9] Student's t-test

LOS, length of hospital stay; MIMAT, mirBase accession number for mature miRNA; SD, standard deviation

FIGURE 4S

Supplemental Table S6: Predictive Model Construction and Performance

| *Need for pharmacological treatment models* | | | | | | | | | |
|---|---|---|---|---|---|---|---|---|---|
| | Model 1 | | | Model2 | | | Model 3 | | |
| | Firth Model[1] | | Bias-adjusted | Firth Model[1] | | Bias-adjusted | Firth Model[1] | | Bias-adjusted |
| *Logistic Regression Model* | Estimate | P-value | Estimate | Estimate | P-value | Estimate | Estimate | P-value | Estimate |
| AUC, estimate | 0.940 | | 0.905 | 0.961 | | 0.909 | 0.971 | | 0.904 |
| Factors, parameter estimates (SE) | | | | | | | | | |
| hsa-let-7d-5p | -1.32 (0.59) | 0.03 | | -1.24 (0.64) | 0.05 | | -1.03 (0.62) | 0.10 | |
| hsa-miR-128-3p | 2.19 (0.89) | 0.01 | | 1.24 (0.93) | 0.19 | | 0.92 (0.89) | 0.30 | |
| hsa-miR-30c-5p | -2.08 (1.12) | 0.06 | | -2.33 (1.32) | 0.08 | | -2.16 (1.32) | 0.10 | |
| hsa-miR-421 | 0.83 (0.58) | 0.15 | | 0.79 (0.58) | 0.17 | | 0.87 (0.58) | 0.13 | |
| hsa-miR-584-5p | 1.83 (0.81) | 0.02 | | 1.42 (0.91) | 0.12 | | 1.13 (0.85) | 0.18 | |
| gestational age (weeks) | ---- | | | -0.73 (0.41) | 0.07 | | -0.66 (0.41) | 0.10 | |
| methadone vs buprenorphine | ---- | | | ---- | | | 1.15 (0.88) | 0.19 | |
| | Firth Model[1] | | Bias-adjusted | Firth Model[1] | | Bias-adjusted | Firth Model[1] | | Bias-adjusted |
| *Predictions from Model*[2] | Estimate | 95% CI | Estimate | Estimate | 95% CI | Estimate | Estimate | 95% CI | Estimate |
| Prediction Probability Point | ≥ 0.46 | | | ≥ 0.46 | | | ≥ 0.60 | | |
| Pharm treatment, correct | 15 | | 12 | 16 | | 14 | 15 | | 12 |
| Pharm treatment, incorrect | 2 | | 5 | 3 | | 5 | 2 | | 4 |
| No Pharm treatment, correct | 39 | | 36 | 38 | | 36 | 39 | | 37 |
| No Pharm treatment, incorrect | 2 | | 5 | 1 | | 3 | 2 | | 5 |
| Accuracy, % correct of total | 93.1 | | 82.8 | 93.1 | | 86.2 | 93.1 | | 84.5 |
| Sensitivity, % | 88.2 | (63.6;98.5) | 70.6 | 94.1 | (71.3;99.9) | 82.4 | 88.2 | (63.6;98.5) | 70.6 |
| Specificity, % | 95.1 | (83.5;99.4) | 87.8 | 92.7 | (80.1;98.5) | 87.8 | 95.1 | (83.5;99.4) | 90.2 |
| Positive predictive value, % | 88.2 | (63.6;98.5) | 70.6 | 84.2 | (60.4;96.6) | 73.7 | 88.2 | (63.6;98.5) | 75.0 |
| Negative predictive value, % | 95.1 | (83.5;99.4) | 87.8 | 97.4 | (86.5;99.9) | 92.3 | 95.1 | (83.5;99.4) | 88.1 |

| *Prolonged hospitalization predictive model* | | | | | | | | | |
|---|---|---|---|---|---|---|---|---|---|
| | Model 1 | | | Model 2 | | | Model 3 | | |
| | Firth Model[1] | | Bias-adjusted | Firth Model[1] | | Bias-adjusted | Firth Model[1] | | Bias-adjusted |
| *Logistic Regression Model* | Estimate | P-value | Estimate | Estimate | P-value | Estimate | Estimate | P-value | Estimate |
| AUC, estimate | 0.994 | | 0.946 | 0.999 | | 0.970 | 0.991 | | 0.966 |
| Factors, parameter estimates (SE) | | | | | | | | | |
| hsa-let-7b-5p | -3.46 (1.45) | 0.02 | | -3.57 (1.56) | 0.02 | | ----- | | |

FIGURE 4S (Cont'd)

| | | | | | | | | | |
|---|---|---|---|---|---|---|---|---|---|
| hsa-miR-10b-5p | -1.29 (0.89) | 0.15 | | ---- | | | ---- | | |
| hsa-miR-128-3p | 2.86 (1.48) | 0.05 | | 4.16 (2.33) | 0.07 | | ---- | | |
| hsa-miR-30c-5p | -8.06 (3.49) | 0.02 | | -6.63 (3.30) | 0.04 | | -3.71 (2.09) | 0.08 | |
| hsa-miR-421 | 3.25 (1.42) | 0.02 | | 1.95 (1.04) | 0.06 | | 3.35 (1.47) | 0.02 | |
| gestational age (weeks) | ---- | | | -1.36 (0.66) | 0.04 | | -1.67 (0.58) | 0.004 | |
| methadone vs buprenorphine | ---- | | | ---- | | | 3.82 (1.71) | 0.03 | |
| | Firth Model[1] | | Bias-adjusted | Firth Model[1] | | Bias-adjusted | Firth Model[1] | | Bias-adjusted |
| ***Predictions from Model[2]*** | **Estimate** | **95% CI** | **Estimate** | **Estimate** | **95% CI** | **Estimate** | **Estimate** | **95% CI** | **Estimate** |
| Prediction Probability Point | ≥ 0.55 | | | ≥ 0.45 | | | ≥ 0.40 | | |
| LOS ≥14 days, correct | 14 | | 11 | 15 | | 14 | 15 | | 13 |
| LOS ≥14 days, incorrect | 1 | | 4 | 1 | | 2 | 2 | | 3 |
| LOS <14 days, correct | 42 | | 39 | 42 | | 41 | 41 | | 40 |
| LOS <14 days, incorrect | 1 | | 4 | 0 | | 1 | 0 | | 2 |
| Accuracy, % correct of total | 96.6 | | 86.2 | 98.3 | | 94.8 | 96.6 | | 91.4 |
| Sensitivity, % | 93.3 | (68.1;99.8) | 73.3 | 100.0 | (78.2;100.0) | 93.3 | 100.0 | (78.2;100.0) | 86.7 |
| Specificity, % | 97.7 | (87.7;99.9) | 90.7 | 97.7 | (87.7;99.9) | 95.3 | 95.3 | (84.2;99.4) | 93.0 |
| Positive predictive value, % | 93.3 | (68.1;99.8) | 73.3 | 93.8 | (69.8;99.8) | 87.5 | 88.2 | (63.6;98.5) | 81.3 |
| Negative predictive value, % | 97.7 | (87.7;99.9) | 90.7 | 100.0 | (91.6;100.00) | 97.6 | 100.0 | (91.3;100.0) | 95.2 |

[1] maximum likelihood estimates adjusted for small sample size using Firth's penalized likelihood approach

[2] based on using prediction probability point specified for each model

Model 1 includes signature miRNAs

Model 2 includes signature miRNAs and gestational age

Model 3 includes signature miRNAs, gestational age, and the type maternal MOUD

AUC, area under receiver operating characteristic curve; CI, confidence interval; MOUD, medication for opioid use disorder; SE, standard error

FIGURE 13

Table 1

Table 1. Validity of miRNAs Batteries in Umbilical Cord Plasma (including a combination of 1-6 miRNAs) the Most Predictive of Severe NOWS

| | **6 miRNAs** AUC (95% CI) | **5 miRNAs** AUC (95% CI) | **4 miRNAs** AUC (95% CI) | **3 miRNAs** AUC (95% CI) | **2 miRNAs** AUC (95% CI) | **1 miRNA** AUC (95% CI) |
|---|---|---|---|---|---|---|
| | 0.881 (0.77,0.99) | 0.881 (0.77,0.99) | 0.876 (0.77,0.99) | 0.869 (0.76,0.98) | 0.837 (0.72,0.96) | 0.793 (0.64,0.95) |
| **Specific miRNA** | β (se) p | β (se) p | β (se) p | β (se) p | β (se) p | β (se) p |
| *Intercept* | *0.31 (5.64) 0.956* | *0.84 (4.44) 0.851* | *-2.21 (1.43) 0.124* | *-1.24 (0.83) 0.137* | *-0.90 (0.75) 0.231* | *-1.87 (0.58) 0.001* |
| **hsa_miR_652_3p** | -2.35 (1.23) 0.057 | -2.35 (1.25) 0.061 | -1.91 (1.05) 0.068 | -2.02 (1.02) 0.047 | -2.39 (0.98) 0.014 | -2.47 (0.91) 0.007 |
| **hsa_miR_423_5p** | -1.12 (1.11) 0.314 | -1.14 (1.12) 0.309 | -0.90 (1.05) 0.392 | | | |
| **hsa_miR_365a_3p** | 0.61 (0.51) 0.229 | 0.56 (0.38) 0.134 | 0.50 (0.37) 0.174 | 0.51 (0.38) 0.175 | | |
| hsa_miR_20a_5p | 0.58 (1.02) 0.569 | 0.65 (0.91) 0.475 | | | | |
| hsa_miR_222_3p | -0.15 (0.99) 0.881 | | | | | |
| **hsa_let_7b_5p** | 0.80 (0.51) 0.114 | 0.83 (0.47) 0.077 | 0.78 (0.46) 0.088 | 0.82 (0.47) 0.083 | 0.86 (0.43) 0.044 | |

FIGURE 16

Table 2

| Indicative of NOWS | Predictive of length of stay | Predictive of extended stay (>14 days) |
|---|---|---|
| **hsa-miR-652-3p** | **hsa-miR-652-3p** | hsa-miR-652-3p |
| **hsa-miR-365a-3p** | **hsa-miR-365a-3p** | hsa-miR-365a-3p |
| **hsa-let-7b-5p** | **hsa-let-7b-5p** | hsa-let-7b-5p |
| **hsa-miR-423-5p** | hsa-miR-423-5p | hsa-miR-423-5p |
| **hsa-miR-18b-5p** | hsa-miR-18b-5p | hsa-miR-18b-5p |
| **hsa-miR-100-5p** | hsa-miR-100-5p | hsa-miR-100-5p |
| **hsa-miR-29a-3p** | hsa-miR-29a-3p | hsa-miR-29a-3p |
| hsa-miR-27b-3p | hsa-miR-27b-3p | hsa-miR-27b-3p |
| hsa-miR-21-5p | hsa-miR-21-5p | hsa-miR-21-5p |
| hsa-miR-629-5p | hsa-miR-629-5p | hsa-miR-629-5p |
| hsa-miR-30c-5p | hsa-miR-30c-5p | hsa-miR-30c-5p |
| hsa-miR-141-3p | hsa-miR-141-3p | hsa-miR-141-3p |
| hsa-miR-29c-3p | hsa-miR-29c-3p | hsa-miR-29c-3p |
| **hsa-miR-20a-5p** | hsa-miR-20a-5p | |
| **hsa-miR-222-3p** | hsa-miR-222-3p | |
| **hsa-miR-331-3p** | | |
| hsa-miR-34a-5p | | |
| hsa-miR-154-5p | | |
| hsa-miR-18a-5p | | |
| hsa-miR-28-5p | | |
| hsa-miR-532-3p | | |
| | **hsa-miR-103a-3p** | hsa-miR-103a-3p |
| | hsa-miR-200a-3p | **hsa-miR-200a-3p** |
| | hsa-let-7e-5p | hsa-let-7e-5p |
| | hsa-miR-191-5p | hsa-miR-191-5p |
| | hsa-miR-30a-5p | hsa-miR-30a-5p |
| | hsa-miR-885-5p | hsa-miR-885-5p |
| | hsa-miR-23a-3p | hsa-miR-23a-3p |
| | hsa-miR-125a-5p | hsa-miR-125a-5p |
| | hsa-miR-125b-5p | hsa-miR-125b-5p |
| | hsa-miR-205-5p | hsa-miR-205-5p |
| | hsa-miR-326 | |
| | | hsa-miR-23b-3p |
| | | hsa-miR-382-5p |
| | | hsa-miR-93-5p |
| | | hsa-miR-24-3p |

FIGURE 19

Table 3 Maternal Socio-demographic, Medical Characteristics, and Substance Use Patterns

| Variable | Not-Pharmacologically Treated (N=41) | Pharmacologically-Treated (N=17) | p-value |
|---|---|---|---|
| *Socio-demographic and medical characteristics* | | | |
| | Mean ± SD | Mean ± SD | |
| Maternal age at enrollment (yrs) | 29.2 ± 5.9 | 27.2 ± 5.4 | 0.23[0] |
| Gestational age at enrollment (wks) | 22.1 ± 7.4 | 20.2 ± 6.8 | 0.41[1] |
| Body mass index (BMI) | 25.2 ± 5.2 | 24.6 ± 5.9 | 0.68[0] |
| | N (%) | N (%) | |
| Race: | | | 0.79[3] |
| White | 37 (90.2%) | 15 (88.2%) | |
| American Indian | 3 (7.3%) | 1 (5.9%) | |
| Other or Mixed | 1 (2.4%) | 1 (5.9%) | |
| Ethnicity: Hispanic/Latina | 31 (75.6%) | 12 (70.6%) | 0.75[3] |
| Marital/cohabiting status: | | | 0.26[3] |
| Single/separated/divorced | 19 (46.3%) | 5 (29.4%) | |
| Married/cohabiting | 22 (53.7%) | 12 (70.6%) | |
| Educational Level: less than high school | 15 (36.6%) | 5 (29.4%) | 0.89[3] |
| Employed (at enrollment) | 17 (41.5%) | 5 (29.4%) | 0.55[3] |
| Health insurance: | | | 0.35[3] |
| Employer-based insurance/Self-purchased/Other | 2 (4.9%) | 1 (5.9%) | |
| Medicaid | 39 (95.1%) | 16 (94.1%) | |
| Gravidity: Primigravida | 5 (12.2%) | 4 (23.5%) | 0.43[3] |
| Parity: nulliparous | 8 (19.5%) | 6 (35.3%) | 0.20[2] |
| Medical conditions: | | | |
| Hepatitis C | 9 (22.0%) | 6 (35.3%) | 0.03[2] |
| Non-severe preeclampsia/gestational hypertension | 4 (9.8%) | 3 (17.6%) | 0.41[3] |
| Severe preeclampsia (requiring emergency delivery) | 1 (2.4%) | 1 (5.9%) | 0.50[3] |
| Chronic hypertension (diagnosed before pregnancy) | 1 (2.4%) | 2 (11.8%) | 0.20[3] |
| *Substance use patterns* | | | |
| | N (%) | N (%) | |
| MOUD | | | <0.01[3] |
| Buprenorphine | 31 (75.6%) | 6 (35.3%) | |
| Methadone | 10 (24.4%) | 11 (64.7%) | |
| Other opioids: | | | |
| Heroin | 15 (36.6%) | 6 (35.3%) | 0.93[2] |
| Misuse of opioid analgesics | 16 (39.0%) | 6 (35.3%) | 0.79[2] |
| Alcohol use | 14 (34.1%) | 2 (11.8%) | 0.11[3] |
| Positive for 1 ethanol biomarker | | | |
| Benzodiazepines | 12 (29.3%) | 3 (17.6%) | 0.36[2] |
| Sedatives | 2 (4.9%) | 1 (5.9%) | 1.00[3] |
| Marijuana | 18 (43.9%) | 7 (41.2%) | 0.85[2] |
| Other substances | 2 (4.9%) | 0 (0.0%) | 1.00[3] |

FIGURE 19 (Cont'd)

| Variable | Not-Pharmacologically Treated (N=41) | Pharmacologically-Treated (N=17) | p-value |
|---|---|---|---|
| Any tobacco use | 36 (87.8%) | 16 (94.1%) | 0.47[2] |
| Any stimulants[4] | 6 (14.6%) | 1 (5.9%) | 1.00[3] |
| | Mean ± SD | Mean ± SD | |
| AUDIT score | 7.1 ± 11.1 | 1.6 ± 2.3 | 0.11[1] |
| Absolute alcohol(oz) per day[5] | 0.3 ± 0.7 | 0.01 ± 0.04 | 0.08[1] |

[0] based on pooled variances t-test
[1] based on Mann-Whitney test
[2] based on Chi-square test
[3] based on Fisher's exact test
[4] any use of methamphetamines, cocaine, crack MDMA, PCP, or other inhalants (more than occasional use of stimulants anytime in pregnancy and any use after the first trimester were exclusionary criteria)
[5] average use from 3 timeline follow-back (TLFB) calendars
AUDIT, Alcohol Use Disorders Identification Test
MOUD, medications for opioid use disorder
NOWS, neonatal opioid withdrawal syndrome
SD, standard deviation

FIGURE 20

Table 3. Perinatal and Infant Characteristics

| Variable | Not-Pharmacologically-Treated (N = 41) | Pharmacologically-Treated (N = 17) | p-value |
|---|---|---|---|
| | Mean ± SD | Mean ± SD | |
| Gestational age at delivery (weeks) | 38.8 ± 1.4 | 36.9 ± 1.0 | <0.001[1] |
| Infant birth weight (grams) | 2999.0 ± 453.6 | 2702.7 ± 249.7 | 0.01[°] |
| Length of hospitalization (days) | 6.0 ± 3.6 | 19.5 ± 9.5 | <0.001[1] |
| APGAR score at 1 minute | 8.0 ± 0.6 | 7.5 ± 1.5 | 0.10[1] |
| APGAR score at 5 minutes | 8.7 ± 1.4 | 8.7 ± 0.8 | 0.41[1] |
| | N (%) | N (%) | |
| Preterm delivery (< 37 weeks) | 2 (4.9%) | 4 (23.5%) | 0.06[3] |
| Delivery type: vaginal | 35 (85.4%) | 12 (70.6%) | 0.19[2] |
| APGAR score < 7 at 1 minute | 1 (2.4%) | 1 (5.9%) | 0.50[3] |
| APGAR score < 7 at 5 minutes | 1 (2.4%) | 1 (5.9%) | 0.50[3] |
| Infant's gender: boy | 21 (51.2%) | 7 (41.2%) | 0.49[2] |
| Length of hospitalization ≥ 14 days | 2 (4.9%) | 13 (76.5%) | <0.001[3] |
| Neonatal complications: | | | |
| Hyperbilirubinemia requiring phototherapy | 16 (39.0%) | 8 (47.1%) | 0.77[3] |
| Respiratory distress | 4 (9.8%) | 8 (47.1%) | <0.01[3] |
| Hypoglycemia | 0 (0.0%) | 2 (11.8%) | 0.08[3] |
| Tachypnea | 1 (2.4%) | 2 (11.8%) | 0.20[3] |
| Bradycardia | 3 (7.3%) | 2 (11.8%) | 0.62[3] |
| Sepsis | 0 (0.0%) | 0 (100.0%) | 1.00[3] |

° based on pooled variances t-test

[1] based on Mann-Whitney test

[2] based on Chi-square test

[3] based on Fisher's exact test

APGAR score, appearance, pulse, grimace, activity, and respiration score; NOWS, neonatal opioid withdrawal syndrome; SD, standard deviation

FIGURE 21

Table 5. Summary of Preliminary Analysis Results for miRNA Candidates for Predictive Models

| | | Pharmacological Treatment | | LOS ≥ 14 Days | |
|---|---|---|---|---|---|
| MiRNA | Potential Model | Difference[1] Mean (SD) | Cohen's *d* | Difference[1] Mean (SD) | Cohen's *d* |
| hsa-let-7b-5p | BOTH | -0.77 (0.88)^ | 0.88 | -1.13 (0.81)^ | 1.40 |
| hsa-miR-125a-5p | BOTH | -0.73 (1.24)^ | 0.59 | -0.86 (1.22)^ | 0.70 |
| hsa-miR-128-3p | BOTH | 0.41 (0.64)^ | 0.64 | 0.54 (0.62)^ | 0.86 |
| hsa-miR-154-5p | BOTH | 0.62 (0.85)^ | 0.72 | 0.60 (0.86)^ | 0.69 |
| hsa-miR-18b-5p | BOTH | 0.53 (0.74)^ | 0.71 | 0.64 (0.73)^ | 0.87 |
| hsa-miR-21-5p | BOTH | -0.27 (0.59)~ | 0.47 | -0.43 (0.57)^ | 0.76 |
| hsa-miR-23a-3p | BOTH | -0.47 (0.81)^ | 0.58 | -0.59 (0.80)^ | 0.74 |
| hsa-miR-23b-3p | BOTH | -0.40 (0.77)~ | 0.52 | -0.51 (0.76)^ | 0.67 |
| hsa-miR-24-3p | BOTH | -0.37 (0.85)~ | 0.44 | -0.52 (0.84)^ | 0.62 |
| hsa-miR-27b-3p | BOTH | -0.34 (0.70)^ | 0.49 | -0.54 (0.67)^ | 0.81 |
| hsa-miR-29a-3p | BOTH | -1.01 (1.30)^ | 0.78 | -1.24 (1.26)^ | 0.99 |
| hsa-miR-29c-3p | BOTH | -0.62 (1.11)~ | 0.56 | -0.75 (1.09)^ | 0.68 |
| hsa-miR-30a-5p | BOTH | -0.73 (0.91)^ | 0.80 | -0.98 (0.87)^ | 1.13 |
| hsa-miR-30c-5p | BOTH | -0.28 (0.50)~ | 0.55 | -0.31 (0.50)^ | 0.63 |
| hsa-miR-362-3p | BOTH | 0.92 (1.62)^ | 0.57 | 1.19 (1.59)^ | 0.74 |
| hsa-miR-365a-3p | BOTH | -0.91 (1.50)^ | 0.61 | -1.21 (1.46)^ | 0.83 |
| hsa-miR-382-5p | BOTH | 0.59 (0.95)~ | 0.63 | 0.60 (0.95)~ | 0.63 |
| hsa-miR-421 | BOTH | 0.91 (0.86)^ | 1.06 | 0.86 (0.87)^ | 0.98 |
| hsa-miR-423-3p | BOTH | 0.26 (0.49)~ | 0.53 | 0.27 (0.49)~ | 0.55 |
| hsa-miR-423-5p | BOTH | 0.28 (0.43)^ | 0.65 | 0.25 (0.43)~ | 0.58 |
| hsa-miR-484 | BOTH | 0.39 (0.54)^ | 0.72 | 0.40 (0.54)^ | 0.74 |
| hsa-miR-495-3p | BOTH | 0.46 (1.01)~ | 0.46 | 0.61 (1.00)^ | 0.61 |
| hsa-miR-584-5p | BOTH | 0.54 (0.75)^ | 0.73 | 0.48 (0.76)^ | 0.64 |
| hsa-miR-629-5p | BOTH | 0.77 (1.29)~ | 0.59 | 0.77 (1.30)^ | 0.59 |
| hsa-miR-652-3p | BOTH | 0.40 (0.58)^ | 0.70 | 0.50 (0.56)^ | 0.90 |
| hsa-let-7d-5p | Pharm Trt | -0.65 (1.01)~ | 0.65 | -0.52 (1.03) | 0.51 |
| hsa-miR-133b | Pharm Trt | -0.92 (1.81)~ | 0.51 | -0.89 (1.81) | 0.49 |
| hsa-miR-146b-5p | Pharm Trt | -0.75 (0.93)^ | 0.80 | -0.47 (0.97) | 0.49 |
| hsa-miR-152-3p | Pharm Trt | 0.25 (0.46)^ | 0.53 | 0.19 (0.47) | 0.42 |
| hsa-miR-186-5p | Pharm Trt | 0.36 (0.72)~ | 0.50 | 0.37 (0.73) | 0.51 |
| hsa-miR-18a-5p | Pharm Trt | 0.43 (0.77)^ | 0.56 | 0.35 (0.78) | 0.45 |
| hsa-miR-223-5p | Pharm Trt | -1.06 (2.02)~ | 0.52 | -0.02 (2.08) | 0.01 |
| hsa-miR-320d | Pharm Trt | 0.27 (0.54)~ | 0.50 | 0.19 (0.55) | 0.34 |
| hsa-miR-324-5p | Pharm Trt | 0.99 (2.30)^ | 0.43 | 0.11 (2.34) | 0.05 |
| hsa-miR-543 | Pharm Trt | 1.30 (3.18)^ | 0.41 | 1.23 (3.19)~ | 0.39 |
| hsa-let-7e-5p | LOS | -0.39 (0.72) | 0.53 | -0.54 (0.71)^ | 0.77 |
| hsa-miR-103a-3p | LOS | 0.18 (0.74) | 0.25 | 0.41 (0.72)~ | 0.57 |
| hsa-miR-10b-5p | LOS | -0.25 (0.92) | 0.28 | -0.59 (0.89)^ | 0.66 |
| hsa-miR-125b-5p | LOS | -0.40 (1.15) | 0.35 | -0.67 (1.12)^ | 0.60 |
| hsa-miR-127-3p | LOS | 0.32 (0.95) | 0.33 | 0.51 (0.94)~ | 0.54 |
| hsa-miR-146a-5p | LOS | 0.24 (0.83) | 0.30 | 0.48 (0.81)~ | 0.59 |
| hsa-miR-191-5p | LOS | 0.08 (0.56) | 0.14 | 0.30 (0.55)^ | 0.54 |
| hsa-miR-27a-3p | LOS | -0.36 (0.82) | 0.44 | -0.51 (0.81)^ | 0.63 |
| hsa-miR-328-3p | LOS | -0.17 (0.75) | 0.23 | -0.49 (0.73)~ | 0.67 |
| hsa-miR-34a-5p | LOS | -0.21 (1.23) | 0.17 | -0.55 (1.21)~ | 0.46 |
| hsa-miR-376c-3p | LOS | 0.43 (1.04) | 0.41 | 0.52 (1.03)~ | 0.50 |
| hsa-miR-409-3p | LOS | 0.49 (1.04) | 0.47 | 0.77 (1.01)^ | 0.76 |

FIGURE 21 CONT'D

Table 5 Cont'd

| MiRNA | Potential Model | Pharmacological Treatment Difference[1] Mean (SD) | Pharmacological Treatment Cohen's *d* | LOS ≥ 14 Days Difference[1] Mean (SD) | LOS ≥ 14 Days Cohen's *d* |
|---|---|---|---|---|---|
| hsa-miR-425-3p | LOS | 0.33 (0.90) | 0.37 | 0.46 (0.89)~ | 0.52 |
| hsa-miR-505-3p | LOS | 0.13 (0.76) | 0.18 | 0.38 (0.74)^ | 0.51 |
| hsa-miR-532-5p | LOS | 0.33 (0.71) | 0.46 | 0.39 (0.71)~ | 0.55 |
| hsa-miR-99a-5p | LOS | -0.33 (0.92) | 0.36 | -0.61 (0.89)^ | 0.69 |

[1]miRNA meeting criteria based on unadjusted mean difference analyses. Difference (ΔΔCT) is mean for *Pharmacologically-Treated* less *Not-Pharmacologically Treated, LOS ≥ 14 days* less *LOS < 14 days.* miRNAs were selected as candidates for a model if effect size (Cohen's *d*) > 0.4 and if mean expression difference $p < 0.10$.

P-values for mean difference: ^ <0.05, ~ <0.10

SD, standard deviation

FIGURE 22

Table 5: Predictive Validity of the miRNA Signature[a] for Identification of Infants with NOWS Requiring Pharmacologic Treatment or Prolonged Hospitalization

| | Model 1 | | | Model 2 | | | Model 3 | | |
|---|---|---|---|---|---|---|---|---|---|
| | Firth Model[1] | | Bias-adjusted | Firth Model[1] | | Bias-adjusted | Firth Model[1] | | Bias-adjusted |
| *Indices of validity*[2] | Estimate | 95% CI | Estimate | Estimate | 95% CI | Estimate | Estimate | 95% CI | Estimate |
| **Need for pharmacologic treatment** | | | | | | | | | |
| Accuracy, % correct of total | 93.1 | | 82.8 | 93.1 | | 86.2 | 93.1 | | 84.5 |
| Sensitivity, % | 88.2 | (63.6;98.5) | 70.6 | 94.1 | (71.3;99.9) | 82.4 | 88.2 | (63.6;98.5) | 70.6 |
| Specificity, % | 95.1 | (83.5;99.4) | 87.8 | 92.7 | (80.1;98.5) | 87.8 | 95.1 | (83.5;99.4) | 90.2 |
| PPV, % | 88.2 | (63.6;98.5) | 70.6 | 84.2 | (60.4;96.6) | 73.7 | 88.2 | (63.6;98.5) | 75.0 |
| NPV, % | 95.1 | (83.5;99.4) | 87.8 | 97.4 | (86.5;99.9) | 92.3 | 95.1 | (83.5;99.4) | 88.1 |
| **Prolonged hospitalization** | | | | | | | | | |
| Accuracy, % correct of total | 96.6 | | 86.2 | 98.3 | | 94.8 | 96.6 | | 91.4 |
| Sensitivity, % | 93.3 | (68.1;99.8) | 73.3 | 100.0 | (78.2;100.0) | 93.3 | 100.0 | (78.2;100.0) | 86.7 |
| Specificity, % | 97.7 | (87.7;99.9) | 90.7 | 97.7 | (87.7;99.9) | 95.3 | 95.3 | (84.2;99.4) | 93.0 |
| PPV, % | 93.3 | (68.1;99.8) | 73.3 | 93.8 | (69.8;99.8) | 87.5 | 88.2 | (63.6;98.5) | 81.3 |
| NPV, % | 97.7 | (87.7,99.9) | 90.7 | 100.0 | (91.6;100.0) | 97.6 | 100.0 | (91.3;100.0 | 95.2 |

[a] Includes let-7d-5p, miR-128-3p, miR-30c-5p, miR-421, miR-584-5p for need for pharmacologic treatment and let-7b-5p, miR-10b-5p, miR-128-3p, miR-30c-5p, and miR-421 for prolonged hospitalization. For prolonged hospitalization, miR-10b-5p was dropped from Model 2 and miR-10b-5p, let-7b-5p, and miR-128-3p were dropped from Model 3 due to lack of convergence.

[1] maximum likelihood estimates adjusted for small sample size using Firth's penalized likelihood approach

[2] based on using prediction probability point specified for each model (pharmacological treatment: Models 1 and 2: ≥ 0.46, Model 3: ≥ 0.60; prolonged hospitalization: Model 1: ≥ 0.55, Model 2: ≥ 0.45, Model 3: ≥ 0.40)

Model 1 includes signature miRNAs

Model 2 includes signature miRNAs and gestational age

Model 3 includes signature miRNAs, gestational age, and the type maternal MOUD

CI, confidence interval; MOUD, medication for opioid use disorder; NPV, negative predictive value; PPV, positive predictive value

FIGURE 26

| miRNA | Model | SEQUENCE | MIMAT | Pharm Trt | LT Hospital | SEQ ID NO |
|---|---|---|---|---|---|---|
| hsa-let-7b-5p | BOTH | UGAGGUAGUAGGUUGUGUGGUU | MIMAT0000063 | *Decreased* | *Decreased* | SEQ ID NO:1 |
| hsa-miR-125a-5p | BOTH | UCCCUGAGACCCUUUAACCUGUGA | MIMAT0000443 | *Decreased* | *Decreased* | SEQ ID NO:2 |
| hsa-miR-128-3p | BOTH | UCACAGUGAACCGGUCUCUUU | MIMAT0000424 | Increased | Increased | SEQ ID NO:3 |
| hsa-miR-154-5p | BOTH | UAGGUUAUCCGUGUUGCCUUCG | MIMAT0000452 | Increased | Increased | SEQ ID NO:4 |
| hsa-miR-18b-5p | BOTH | UAAGGUGCAUCUAGUGCAGUUAG | MIMAT0001412 | Increased | Increased | SEQ ID NO:5 |
| hsa-miR-21-5p | BOTH | UAGCUUAUCAGACUGAUGUUGA | MIMAT0000076 | *Decreased* | *Decreased* | SEQ ID NO:6 |
| hsa-miR-23a-3p | BOTH | AUCACAUUGCCAGGGAUUUCC | MIMAT0000078 | *Decreased* | *Decreased* | SEQ ID NO:7 |
| hsa-miR-23b-3p | BOTH | AUCACAUUGCCAGGGAUUACC | MIMAT0000418 | *Decreased* | *Decreased* | SEQ ID NO:8 |
| hsa-miR-24-3p | BOTH | UGGCUCAGUUCAGCAGGAACAG | MIMAT0000080 | *Decreased* | *Decreased* | SEQ ID NO:9 |
| hsa-miR-27b-3p | BOTH | UUCACAGUGGCUAAGUUCUGC | MIMAT0000419 | *Decreased* | *Decreased* | SEQ ID NO:10 |
| hsa-miR-29a-3p | BOTH | UAGCACCAUCUGAAAUCGGUUA | MIMAT0000086 | *Decreased* | *Decreased* | SEQ ID NO:11 |
| hsa-miR-29c-3p | BOTH | UAGCACCAUUUGAAAUCGGUUA | MIMAT0000681 | *Decreased* | *Decreased* | SEQ ID NO:12 |
| hsa-miR-30a-5p | BOTH | UGUAAACAUCCUCGACUGGAAG | MIMAT0000087 | *Decreased* | *Decreased* | SEQ ID NO:13 |
| hsa-miR-30c-5p | BOTH | UGUAAACAUCCUACACUCUCAGC | MIMAT0000244 | *Decreased* | *Decreased* | SEQ ID NO:14 |
| hsa-miR-362-3p | BOTH | AACACACCUAUUCAAGGAUUCA | MIMAT0004683 | Increased | Increased | SEQ ID NO:15 |
| hsa-miR-365a-3p | BOTH | UAAUGCCCCUAAAAAUCCUUAU | MIMAT0000710 | *Decreased* | *Decreased* | SEQ ID NO:16 |
| hsa-miR-382-5p | BOTH | GAAGUUGUUCGUGGUGGAUUCG | MIMAT0000737 | Increased | Increased | SEQ ID NO:17 |
| hsa-miR-421 | BOTH | AUCAACAGACAUUAAUUGGGCGC | MIMAT0003339 | Increased | Increased | SEQ ID NO:18 |
| hsa-miR-423-3p | BOTH | AGCUCGGUCUGAGGCCCCUCAGU | MIMAT0001340 | Increased | Increased | SEQ ID NO:19 |
| hsa-miR-423-5p | BOTH | UGAGGGGCAGAGAGCGAGACUUU | MIMAT0004748 | Increased | Increased | SEQ ID NO:20 |
| hsa-miR-484 | BOTH | UCAGGCUCAGUCCCCUCCCGAU | MIMAT0002174 | Increased | Increased | SEQ ID NO:21 |
| hsa-miR-495-3p | BOTH | AAACAAACAUGGUGCACUUCUU | MIMAT0002817 | Increased | Increased | SEQ ID NO:22 |
| hsa-miR-584-5p | BOTH | UUAUGGUUUGCCUGGGACUGAG | MIMAT0003249 | Increased | Increased | SEQ ID NO:23 |
| hsa-miR-629-5p | BOTH | UGGGUUUACGUUGGGAGAACU | MIMAT0004810 | Increased | Increased | SEQ ID NO:24 |
| hsa-miR-652-3p | BOTH | AAUGGCGCCACUAGGGUUGUG | MIMAT0003322 | Increased | Increased | SEQ ID NO:25 |
| hsa-let-7d-5p | Pharm Trt | AGAGGUAGUAGGUUGCAUAGUU | MIMAT0000065 | *Decreased* | | SEQ ID NO:26 |
| hsa-miR-133b | Pharm Trt | UUUGGUCCCCUUCAACCAGCUA | MIMAT0000770 | *Decreased* | | SEQ ID NO:27 |
| hsa-miR-146b-5p | Pharm Trt | UGAGAACUGAAUUCCAUAGGCU | MIMAT0002809 | *Decreased* | | SEQ ID NO:28 |
| hsa-miR-152-3p | Pharm Trt | UCAGUGCAUGACAGAACUUGG | MIMAT0000438 | Increased | | SEQ ID NO:29 |

FIGURE 26 (Cont'd)

| miRNA | Model | SEQUENCE | MIMAT | Pharm Trt | LT Hospital | SEQ ID NO. |
|---|---|---|---|---|---|---|
| hsa-miR-186-5p | Pharm Trt | CAAAGAAUUCUCCUUUUGGGCU | MIMAT0000456 | **Increased** | | SEQ ID NO:30 |
| hsa-miR-18a-5p | Pharm Trt | UAAGGUGCAUCUAGUGCAGAUAG | MIMAT0000072 | **Increased** | | SEQ ID NO:31 |
| hsa-miR-223-5p | Pharm Trt | CGUGUAUUUGACAAGCUGAGUU | MIMAT0004570 | *Decreased* | | SEQ ID NO:32 |
| hsa-miR-320d | Pharm Trt | AAAAGCUGGGUUGAGAGGA | MIMAT0006764 | **Increased** | | SEQ ID NO:33 |
| hsa-miR-324-5p | Pharm Trt | CGCAUCCCCUAGGGCAUUGGUGU | MIMAT0000761 | **Increased** | | SEQ ID NO:34 |
| hsa-miR-543 | Pharm Trt | AAACAUUCGCGGUGCACUUCUU | MIMAT0004954 | **Increased** | | SEQ ID NO:35 |
| hsa-let-7e-5p | LOS | UGAGGUAGGAGGUUGUAUAGUU | MIMAT0000066 | | *Decreased* | SEQ ID NO:36 |
| hsa-miR-103a-3p | LOS | AGCAGCAUUGUACAGGGCUAUGA | MIMAT0000101 | | **Increased** | SEQ ID NO:37 |
| hsa-miR-10b-5p | LOS | UACCCUGUAGAACCGAAUUUGUG | MIMAT0000254 | | *Decreased* | SEQ ID NO:38 |
| hsa-miR-125b-5p | LOS | UCCCUGAGACCCUAACUUGUGA | MIMAT0000423 | | *Decreased* | SEQ ID NO:39 |
| hsa-miR-127-3p | LOS | UCGGAUCCGUCUGAGCUUGGCU | MIMAT0000446 | | **Increased** | SEQ ID NO:40 |
| hsa-miR-146a-5p | LOS | UGAGAACUGAAUUCCAUGGGUU | MIMAT0000449 | | **Increased** | SEQ ID NO:41 |
| hsa-miR-191-5p | LOS | CAACGGAAUCCCAAAAGCAGCUG | MIMAT0000440 | | **Increased** | SEQ ID NO:42 |
| hsa-miR-27a-3p | LOS | UUCACAGUGGCUAAGUUCCGC | MIMAT0000084 | | *Decreased* | SEQ ID NO:43 |
| hsa-miR-328-3p | LOS | CUGGCCCUCUCUGCCCUUCCGU | MIMAT0000752 | | *Decreased* | SEQ ID NO:44 |
| hsa-miR-34a-5p | LOS | UGGCAGUGUCUUAGCUGGUUGU | MIMAT0000255 | | *Decreased* | SEQ ID NO:45 |
| hsa-miR-376c-3p | LOS | AACAUAGAGGAAAUUCCACGU | MIMAT0000720 | | **Increased** | SEQ ID NO:46 |
| hsa-miR-409-3p | LOS | GAAUGUUGCUCGGUGAACCCCU | MIMAT0001639 | | **Increased** | SEQ ID NO:47 |
| hsa-miR-425-3p | LOS | AUCGGGAAUGUCGUGUCCGCCC | MIMAT0001343 | | **Increased** | SEQ ID NO:48 |
| hsa-miR-505-3p | LOS | CGUCAACACUUGCUGGUUUCCU | MIMAT0002876 | | **Increased** | SEQ ID NO:49 |
| hsa-miR-532-5p | LOS | CAUGCCUUGAGUGUAGGACCGU | MIMAT0002888 | | **Increased** | SEQ ID NO:50 |
| hsa-miR-99a-5p | LOS | AACCCGUAGAUCCGAUCUUGUG | MIMAT0000097 | | *Decreased* | SEQ ID NO:51 |

Bold font indicates miRNAs overexpressed (positive association) with predicted outcome, *italicized font* indicates miRNAs under-expressed (negative association)

FIGURE 27

Table 7. Summary of miRNAs included in each tier and corresponding AUC values[1].

| | Tier A | Tier B | Tier C |
|---|---|---|---|
| Need for Pharm Treatment | AUC = 0.940 (0.905)<br>**hsa.miR.128.3p** *hsa.let.7d.5p*<br>**hsa.miR.421** *hsa.miR.30c.5p*<br>**hsa.miR.584.5p** | AUC = 0.940 (0.838)<br>**hsa.miR.495.3p** *hsa.let.7b.5p*<br>**hsa.miR.629.5p** *hsa.miR.146b.5p*<br>**hsa.miR.652.3p** *hsa.miR.223.5p* | AUC = 0.844 (0.787)<br>**hsa.miR.362.3p** *hsa.miR.30a.5p*<br>**hsa.miR.382.5p**<br>**hsa.miR.484** |
| LOS ≥14Days | AUC = 0.994 (0.946)<br>**hsa.miR.128.3p** *hsa.let.7b.5p*<br>**hsa.miR.421** *hsa.miR.10b.5p*<br>*hsa.miR.30c.5p* | AUC = 0.988 (0.931)<br>**hsa.miR.18b.5p** *hsa.miR.30a.5p*<br>**hsa.miR.409.3p** *hsa.miR.328.3p*<br>**hsa.miR.423.5p**<br>**hsa.miR.584.5p** | AUC = 0.986 (0.909)<br>**hsa.miR.103a.3p** *hsa.miR.21.5p*<br>**hsa.miR.146a.5p**<br>**hsa.miR.382.5p**<br>**hsa.miR.484**<br>**hsa.miR.495.3p** |

[1] AUC values in parenthesis are bias-adjusted AUC values
Bold font indicates miRNAs overexpressed (positive association) with predicted outcome
*Italicized font* indicates miRNAs under-expressed (negative association)

FIGURE 28

Table 8 Validity Indices Associated with miRNA Clusters (All Tier Models)

| | Need for pharmacologic Treatment | | | | LOS ≥14 Days | | | |
|---|---|---|---|---|---|---|---|---|
| | (Tiers A, B, C) | | (Tiers A & B) | | (Tiers A, B, C) | | (Tiers A & C) | |
| | Estimate | 95% CI | Estimate | 95% CI | Estimate | 95% CI | Estimate | 95% CI |
| AUC | 96.1 | | 96.3 | | 99.8 | | 99.8 | |
| (Bias-adj AUC) | (91.3) | | (92.0) | | (98.0) | | (98.0) | |
| Accuracy | 94.8 | | 94.8 | | 98.3 | | 98.3 | |
| Sensitivity | 88.2 | (63.6,98.5) | 88.2 | (63.6,98.5) | 100.0 | (78.2,100.0) | 100.0 | (78.2,100.0) |
| Specificity | 97.6 | (87.1,99.9) | 97.6 | (87.1,99.9) | 97.7 | (87.7,99.9) | 97.7 | (87.7,99.9) |
| PPV | 93.8 | (69.8,99.8) | 93.8 | (69.7,99.8) | 93.8 | (69.8,99.8) | 93.8 | (69.8,99.8) |
| NPV | 95.2 | (83.8,99.4) | 95.2 | (83.8,99.4) | 100.0 | (91.6,100.0) | 100.0 | (91.6,100.0) |
| Model Components* | Par Est (SE) | P-value | Par Est (SE) | P-value | Par Est (SE) | P-value | Par Est (SE) | P-value |
| Tier A | 4.69 (1.80) | 0.009 | 4.74 (1.78) | 0.008 | 6.65 (3.32) | 0.05 | 6.79 (2.97) | 0.02 |
| Tier B | 4.86 (2.31) | 0.04 | 4.67 (2.09) | 0.03 | -1.15 (3.82) | 0.76 | -- | |
| Tier C | -0.68 (2.64) | 0.80 | -- | | 5.53 (4.05) | 0.17 | 4.73 (2.55) | 0.06 |

FIGURE 29

Sequences of 51 Relevant miRNAs with SEQ ID NOs.

| miRNA | SEQUENCE | SEQ ID NO |
|---|---|---|
| hsa-let-7b-5p | UGAGGUAGUAGGUUGUGUGGUU | SEQ ID NO: 1 |
| hsa-miR-125a-5p | UCCCUGAGACCCUUUAACCUGUGA | SEQ ID NO:2 |
| hsa-miR-128-3p | UCACAGUGAACCGGUCUCUUU | SEQ ID NO:3 |
| hsa-miR-154-5p | UAGGUUAUCCGUGUUGCCUUCG | SEQ ID NO:4 |
| hsa-miR-18b-5p | UAAGGUGCAUCUAGUGCAGUUAG | SEQ ID NO:5 |
| hsa-miR-21-5p | UAGCUUAUCAGACUGAUGUUGA | SEQ ID NO:6 |
| hsa-miR-23a-3p | AUCACAUUGCCAGGGAUUUCC | SEQ ID NO:7 |
| hsa-miR-23b-3p | AUCACAUUGCCAGGGAUUACC | SEQ ID NO:8 |
| hsa-miR-24-3p | UGGCUCAGUUCAGCAGGAACAG | SEQ ID NO:9 |
| hsa-miR-27b-3p | UUCACAGUGGCUAAGUUCUGC | SEQ ID NO:10 |
| hsa-miR-29a-3p | UAGCACCAUCUGAAAUCGGUUA | SEQ ID NO:11 |
| hsa-miR-29c-3p | UAGCACCAUUUGAAAUCGGUUA | SEQ ID NO:12 |
| hsa-miR-30a-5p | UGUAAACAUCCUCGACUGGAAG | SEQ ID NO:13 |
| hsa-miR-30c-5p | UGUAAACAUCCUACACUCUCAGC | SEQ ID NO:14 |
| hsa-miR-362-3p | AACACACCUAUUCAAGGAUUCA | SEQ ID NO:15 |
| hsa-miR-365a-3p | UAAUGCCCCUAAAAAUCCUUAU | SEQ ID NO:16 |
| hsa-miR-382-5p | GAAGUUGUUCGUGGUGGAUUCG | SEQ ID NO:17 |
| hsa-miR-421 | AUCAACAGACAUUAAUUGGGCGC | SEQ ID NO:18 |
| hsa-miR-423-3p | AGCUCGGUCUGAGGCCCCUCAGU | SEQ ID NO:19 |
| hsa-miR-423-5p | UGAGGGGCAGAGAGCGAGACUUU | SEQ ID NO:20 |
| hsa-miR-484 | UCAGGCUCAGUCCCCUCCCGAU | SEQ ID NO:21 |
| hsa-miR-495-3p | AAACAAACAUGGUGCACUUCUU | SEQ ID NO:22 |
| hsa-miR-584-5p | UUAUGGUUUGCCUGGGACUGAG | SEQ ID NO:23 |
| hsa-miR-629-5p | UGGGUUUACGUUGGGAGAACU | SEQ ID NO:24 |
| hsa-miR-652-3p | AAUGGCGCCACUAGGGUUGUG | SEQ ID NO:25 |
| hsa-let-7d-5p | AGAGGUAGUAGGUUGCAUAGUU | SEQ ID NO:26 |
| hsa-miR-133b | UUUGGUCCCCUUCAACCAGCUA | SEQ ID NO:27 |
| hsa-miR-146b-5p | UGAGAACUGAAUUCCAUAGGCU | SEQ ID NO:28 |
| hsa-miR-152-3p | UCAGUGCAUGACAGAACUUGG | SEQ ID NO:29 |
| hsa-miR-186-5p | CAAAGAAUUCUCCUUUUGGGCU | SEQ ID NO:30 |
| hsa-miR-18a-5p | UAAGGUGCAUCUAGUGCAGAUAG | SEQ ID NO:31 |
| hsa-miR-223-5p | CGUGUAUUUGACAAGCUGAGUU | SEQ ID NO:32 |
| hsa-miR-320d | AAAAGCUGGGUUGAGAGGA | SEQ ID NO:33 |
| hsa-miR-324-5p | CGCAUCCCCUAGGGCAUUGGUGU | SEQ ID NO:34 |
| hsa-miR-543 | AAACAUUCGCGGUGCACUUCUU | SEQ ID NO:35 |
| hsa-let-7e-5p | UGAGGUAGGAGGUUGUAUAGUU | SEQ ID NO:36 |
| hsa-miR-103a-3p | AGCAGCAUUGUACAGGGCUAUGA | SEQ ID NO:37 |
| hsa-miR-10b-5p | UACCCUGUAGAACCGAAUUUGUG | SEQ ID NO:38 |
| hsa-miR-125b-5p | UCCCUGAGACCCUAACUUGUGA | SEQ ID NO:39 |
| hsa-miR-127-3p | UCGGAUCCGUCUGAGCUUGGCU | SEQ ID NO:40 |
| hsa-miR-146a-5p | UGAGAACUGAAUUCCAUGGGUU | SEQ ID NO:41 |
| hsa-miR-191-5p | CAACGGAAUCCCAAAAGCAGCUG | SEQ ID NO:42 |
| hsa-miR-27a-3p | UUCACAGUGGCUAAGUUCCGC | SEQ ID NO:43 |

FIGURE 29 (Cont'd)

| miRNA | SEQUENCE | SEQ ID NO |
|---|---|---|
| hsa-miR-328-3p | CUGGCCCUCUCUGCCCUUCCGU | SEQ ID NO:44 |
| hsa-miR-34a-5p | UGGCAGUGUCUUAGCUGGUUGU | SEQ ID NO:45 |
| hsa-miR-376c-3p | AACAUAGAGGAAAUUCCACGU | SEQ ID NO:46 |
| hsa-miR-409-3p | GAAUGUUGCUCGGUGAACCCCU | SEQ ID NO:47 |
| hsa-miR-425-3p | AUCGGGAAUGUCGUGUCCGCCC | SEQ ID NO:48 |
| hsa-miR-505-3p | CGUCAACACUUGCUGGUUUCCU | SEQ ID NO:49 |
| hsa-miR-532-5p | CAUGCCUUGAGUGUAGGACCGU | SEQ ID NO:50 |
| hsa-miR-99a-5p | AACCCGUAGAUCCGAUCUUGUG | SEQ ID NO:51 |

SEQUENCE LISTING

<160> NUMBER OF SEQ ID NOS: 51

<210> SEQ ID NO 1
<211> LENGTH: 22
<212> TYPE: RNA
<213> ORGANISM: Human

<400> SEQUENCE: 1
ugagguagua gguugugugg uu 22

<210> SEQ ID NO 2
<211> LENGTH: 24
<212> TYPE: RNA
<213> ORGANISM: Human

<400> SEQUENCE: 2
ucccugagac ccuuuaaccu guga 24

<210> SEQ ID NO 3
<211> LENGTH: 21
<212> TYPE: RNA
<213> ORGANISM: Human

<400> SEQUENCE: 3
ucacagugaa ccggucucuu u 21

<210> SEQ ID NO 4
<211> LENGTH: 22
<212> TYPE: RNA
<213> ORGANISM: Human

<400> SEQUENCE: 4
uagguuaucc guguugccuu cg 22

<210> SEQ ID NO 5
<211> LENGTH: 23
<212> TYPE: RNA
<213> ORGANISM: Human

<400> SEQUENCE: 5
uaaggugcau cuagugcagu uag 23

<210> SEQ ID NO 6
<211> LENGTH: 22
<212> TYPE: RNA
<213> ORGANISM: HUMAN

<400> SEQUENCE: 6
uagcuuauca gacugauguu ga 22

<210> SEQ ID NO 7
<211> LENGTH: 21
<212> TYPE: RNA
<213> ORGANISM: HUMAN

<400> SEQUENCE: 7
aucacauugc cagggauuuc c 21

<210> SEQ ID NO 8
<211> LENGTH: 21
<212> TYPE: RNA
<213> ORGANISM: HUMAN

<400> SEQUENCE: 8
aucacauugc cagggauuac c 21

<210> SEQ ID NO 9
<211> LENGTH: 22
<212> TYPE: RNA
<213> ORGANISM: HUMAN

<400> SEQUENCE: 9
uggcucaguu cagcaggaac ag 22

<210> SEQ ID NO 10
<211> LENGTH: 21
<212> TYPE: RNA
<213> ORGANISM: HUMAN

<400> SEQUENCE: 10
uucacagugg cuaaguucug c 21

<210> SEQ ID NO 11
<211> LENGTH: 22
<212> TYPE: RNA
<213> ORGANISM: HUMAN

<400> SEQUENCE: 11
uagcaccauc ugaaaucggu ua 22

<210> SEQ ID NO 12
<211> LENGTH: 22
<212> TYPE: RNA
<213> ORGANISM: HUMAN

<400> SEQUENCE: 12
uagcaccauu ugaaaucggu ua 22

<210> SEQ ID NO 13
<211> LENGTH: 22
<212> TYPE: RNA
<213> ORGANISM: HUMAN

<400> SEQUENCE: 13
uguaaacauc cucgacugga ag 22

<210> SEQ ID NO 14
<211> LENGTH: 23
<212> TYPE: RNA
<213> ORGANISM: HUMAN

<400> SEQUENCE: 14
uguaaacauc cuacacucuc agc 23

<210> SEQ ID NO 15
<211> LENGTH: 22
<212> TYPE: RNA
<213> ORGANISM: HUMAN

<400> SEQUENCE: 15
aacacaccua uucaaggauu ca 22

<210> SEQ ID NO 16
<211> LENGTH: 22
<212> TYPE: RNA
<213> ORGANISM: HUMAN

<400> SEQUENCE: 16
uaaugccccu aaaaauccuu au 22

<210> SEQ ID NO 17
<211> LENGTH: 22
<212> TYPE: RNA
<213> ORGANISM: HUMAN

<400> SEQUENCE: 17
gaaguuguuc gugguggauu cg 22

<210> SEQ ID NO 18
<211> LENGTH: 23
<212> TYPE: RNA
<213> ORGANISM: HUMAN

<400> SEQUENCE: 18
aucaacagac auuaauuggg cgc 23

<210> SEQ ID NO 19
<211> LENGTH: 23
<212> TYPE: RNA
<213> ORGANISM: HUMAN

<400> SEQUENCE: 19
agcucggucu gaggccccuc agu 23

<210> SEQ ID NO 20
<211> LENGTH: 23
<212> TYPE: RNA
<213> ORGANISM: HUMAN

<400> SEQUENCE: 20
ugaggggcag agagcgagac uuu 23

<210> SEQ ID NO 21
<211> LENGTH: 22
<212> TYPE: RNA
<213> ORGANISM: HUMAN

<400> SEQUENCE: 21
ucaggcucag uccccucccg au 22

<210> SEQ ID NO 22
<211> LENGTH: 22
<212> TYPE: RNA
<213> ORGANISM: HUMAN

<400> SEQUENCE: 22
aaacaaacau ggugcacuuc uu 22

<210> SEQ ID NO 23
<211> LENGTH: 22
<212> TYPE: RNA
<213> ORGANISM: HUMAN

<400> SEQUENCE: 23
uuaugguuug ccugggacug ag 22

<210> SEQ ID NO 24
<211> LENGTH: 21
<212> TYPE: RNA
<213> ORGANISM: HUMAN

<400> SEQUENCE: 24
uggguuuacg uugggagaac u 21

<210> SEQ ID NO 25
<211> LENGTH: 21
<212> TYPE: RNA
<213> ORGANISM: HUMAN

<400> SEQUENCE: 25
aauggcgcca cuaggguugu g 21

<210> SEQ ID NO 26
<211> LENGTH: 22
<212> TYPE: RNA
<213> ORGANISM: HUMAN

<400> SEQUENCE: 26
agagguagua gguugcauag uu 22

<210> SEQ ID NO 27
<211> LENGTH: 22
<212> TYPE: RNA
<213> ORGANISM: HUMAN

<400> SEQUENCE: 27
uuuggucccc uucaaccagc ua 22

<210> SEQ ID NO 28
<211> LENGTH: 22
<212> TYPE: RNA
<213> ORGANISM: HUMAN

<400> SEQUENCE: 28
ugagaacuga auuccauagg cu 22

<210> SEQ ID NO 29
<211> LENGTH: 21
<212> TYPE: RNA
<213> ORGANISM: HUMAN

<400> SEQUENCE: 29
ucagugcaug acagaacuug g 21

<210> SEQ ID NO 30
<211> LENGTH: 22
<212> TYPE: RNA
<213> ORGANISM: HUMAN

<400> SEQUENCE: 30
caaagaauuc uccuuuuggg cu 22

<210> SEQ ID NO 31
<211> LENGTH: 23
<212> TYPE: RNA
<213> ORGANISM: HUMAN

<400> SEQUENCE: 31
uaaggugcau cuagugcaga uag 23

<210> SEQ ID NO 32
<211> LENGTH: 22
<212> TYPE: RNA

<213> ORGANISM: HUMAN

<400> SEQUENCE: 32
cguguauuug acaagcugag uu 22

<210> SEQ ID NO 33
<211> LENGTH: 19
<212> TYPE: RNA
<213> ORGANISM: HUMAN

<400> SEQUENCE: 33
aaaagcuggg uugagagga 19

<210> SEQ ID NO 34
<211> LENGTH: 23
<212> TYPE: RNA
<213> ORGANISM: HUMAN

<400> SEQUENCE: 34
cgcauccccu agggcauugg ugu 23

<210> SEQ ID NO 35
<211> LENGTH: 22
<212> TYPE: RNA
<213> ORGANISM: HUMAN

<400> SEQUENCE: 35
aaacauucgc ggugcacuuc uu 22

<210> SEQ ID NO 36
<211> LENGTH: 22
<212> TYPE: RNA
<213> ORGANISM: HUMAN

<400> SEQUENCE: 36
ugagguagga gguuguauag uu 22

<210> SEQ ID NO 37
<211> LENGTH: 23
<212> TYPE: RNA
<213> ORGANISM: HUMAN

<400> SEQUENCE: 37
agcagcauug uacagggcua uga 23

<210> SEQ ID NO 38
<211> LENGTH: 23
<212> TYPE: RNA
<213> ORGANISM: HUMAN

<400> SEQUENCE: 38
uacccuguag aaccgaauuu gug 23

<210> SEQ ID NO 39
<211> LENGTH: 22
<212> TYPE: RNA
<213> ORGANISM: HUMAN

<400> SEQUENCE: 39
ucccugagac ccuaacuugu ga 22

<210> SEQ ID NO 40
<211> LENGTH: 22

<212> TYPE: RNA
<213> ORGANISM: HUMAN

<400> SEQUENCE: 40
ucggauccgu cugagcuugg cu 22

<210> SEQ ID NO 41
<211> LENGTH: 22
<212> TYPE: RNA
<213> ORGANISM: HUMAN

<400> SEQUENCE: 41
ugagaacuga auuccauggg uu 22

<210> SEQ ID NO 42
<211> LENGTH: 23
<212> TYPE: RNA
<213> ORGANISM: HUMAN

<400> SEQUENCE: 42
caacggaauc ccaaaagcag cug 23

<210> SEQ ID NO 43
<211> LENGTH: 21
<212> TYPE: RNA
<213> ORGANISM: HUMAN

<400> SEQUENCE: 43
uucacagugg cuaaguuccg c 21

<210> SEQ ID NO 44
<211> LENGTH: 22
<212> TYPE: RNA
<213> ORGANISM: HUMAN

<400> SEQUENCE: 44
cuggcccucu cugcccuucc gu 22

<210> SEQ ID NO 45
<211> LENGTH: 22
<212> TYPE: RNA
<213> ORGANISM: HUMAN

<400> SEQUENCE: 45
uggcaguguc uuagcugguu gu 22

<210> SEQ ID NO 46
<211> LENGTH: 21
<212> TYPE: RNA
<213> ORGANISM: HUMAN

<400> SEQUENCE: 46
aacauagagg aaauuccacg u 21

<210> SEQ ID NO 47
<211> LENGTH: 22
<212> TYPE: RNA
<213> ORGANISM: HUMAN

<400> SEQUENCE: 47
gaauguugcu cggugaaccc cu 22

<210> SEQ ID NO 48

-continued

<211> LENGTH: 22
<212> TYPE: RNA
<213> ORGANISM: HUMAN

<400> SEQUENCE: 48
aucgggaaug ucguguccgc cc 22

<210> SEQ ID NO 49
<211> LENGTH: 22
<212> TYPE: RNA
<213> ORGANISM: HUMAN

<400> SEQUENCE: 49
cgucaacacu ugcugguuuc cu 22

<210> SEQ ID NO 50
<211> LENGTH: 22
<212> TYPE: RNA
<213> ORGANISM: HUMAN

<400> SEQUENCE: 50
caugccuuga guguaggacc gu 22

<210> SEQ ID NO 51
<211> LENGTH: 22
<212> TYPE: RNA
<213> ORGANISM: HUMAN

<400> SEQUENCE: 51
aacccguaga uccgaucuug ug 22

SIGNATURE miRNA TO PREDICT NEONATAL OPIOID WITHDRAWAL SYNDROME (NOWS)

RELATED APPLICATIONS

This application is a United States national filing phase of PCT application no. PCT/US21/39154 filed on Jun. 25, 2021, which claims the benefit of priority of U.S. provisional application Ser. No. US63/044,528, filed Jun. 26, 2020, the entire contents of each said applications are incorporated by reference herein.

GOVERNMENT SUPPORT

This invention was made with government support under R21HD090733 awarded by the National Institutes of Health. The government has certain rights in the invention.

FIELD OF THE INVENTION

The present invention relates to the discovery of miRNAs which can be isolated from the blood of neonates, especially the umbilical cord or placental blood (plasma, leukocytes) of neonates, which have been determined to be biomarkers for neonatal opioid withdrawal syndrome (NOWS). One or more of these biomarkers may be measured in the blood, preferably the umbilical cord blood or placental blood of neonates suspected of having opioid withdrawal syndrome, and compared with a standard wherein the measurement of the one or more biomarkers evidences the presence of opioid syndrome in the neonate whose blood has been measured so that effective measures can be taken to treat the withdrawal syndrome and inhibit, limit and/or reverse withdrawal syndrome in the neonate shortly after birth. In an embodiment, the cord blood, or other blood sample of a neonate may be obtained and analyzed for opioid withdrawal syndrome. In an embodiment, one or more biomarkers as identified herein may be utilized to determine the effectiveness of therapy by measuring the biomarker at more than one time during a period of therapy (often at the start of therapy and then at least one additional time after therapy commences) to determine whether the one or more biomarkers have been lowered or increased compared to a standard (which preferably may include the one or more biomarkers at the commencement of therapy) which will evidence the effectiveness of the therapy. The therapy may thus be continued, terminated or modified pursuant to the measurements of the one or more biomarkers and compared to a standard.

BACKGROUND AND OVERVIEW OF THE INVENTION

Increased rates of opioid use and misuse in the general population, termed the 'opioid epidemic, are reflected in the increased rates of opioid use in pregnant women. In the U.S., an analysis of hospital discharge data following in-hospital delivery found that among women who had just given birth, the rates of opioid use disorder (OUD) increased more than 4-fold from 1999 to 2014 (Haight et al., 2018). During pregnancy, medication for opioid use disorder (MOUD) consisting of either the partial opioid receptor agonist, buprenorphine, or the full opioid receptor agonist, methadone, is the recommended treatment modality for OUD (American College of Obstetricians and Gynecologists, 2017; National Academies of Sciences Engineering and Medicine (U.S.). Committee on Medication-Assisted Treatment for Opioid Use Disorder et al., 2019). Both chronic opioid use and MOUD can result in neonatal opioid withdrawal syndrome (NOWS), formerly/alternatively labeled as neonatal abstinence syndrome (NAS). Rates of NOWS have also drastically risen, increasing more than 2.5-fold from 2009 to 2017 (Healthcare Cost and Utilization Project, 2021).

NOWS symptoms can include respiratory, gastrointestinal, and feeding problems and often require prolonged hospitalization, and infants can develop serious complications, including, in 2-7% of opioid-exposed neonates, seizures (Doberczak et al., 1991; Herzlinger et al., 1977; Kandall et al., 1977; Zelson et al., 1971). The long-term consequences of prenatal opioid exposure (POE) are unclear as it is often hard to separate the effect of POE from contributing effects of other substances and adverse pregnancy and perinatal environments. Some studies reported that POE might be associated with infant emotional regulation and stress activity (Bakhireva et al., 2019; Beauchamp et al., 2020), systemic inflammation (Jantzie et al., 2020; Vasan et al., 2021), and altered neurodevelopment (Baldacchino et al., 2015; McGlone and Mactier, 2015; Monnelly et al., 2018), however, other studies have been generally reassuring with respect to the effects on cognitive development (Bakhireva et al., 2019; Kaltenbach et al., 2018; Larson et al., 2019). It is estimated that 31-97% of neonates with POE will develop at least some withdrawal symptoms (Chavan et al., 2017; Hudak and Tan, 2012; Staszewski et al., 2020), though there is substantial variability in the incidence, onset, duration, and severity of NOWS. No single factor or combination of known factors bas sufficiently explained the variability in NOWS severity (Lewis et al., 2015; Stover and Davis, 2015). While some protective factors have been identified, i.e. the type of maternal MOUD (buprenorphine vs. methadone), initiation of breastfeeding, rooming-in practices, non-pharmacological interventions, such as Eat, Sleep, Console (ESC), and genetics (Lewis et al., 2015; Newman et al., 2020; O'Connor et al., 2013; O'Connor et al., 2016; Oei and Lui, 2007), large unexplained variability in the severity of NOWS symptoms and severity suggest that additional factors might be at play. Current tools to measure NOWS severity rely on the detection and scoring of symptoms (Grossman et al., 2017; Isemann et al., 2017; Jansson and Patrick, 2019; Jones et al., 2016; Oji-Mmuo et al., 2018; Wachman et al., 2018). One predictive tool recently created is based on maternal and infant characteristics to indicate risk of NOWS development (Patrick et al., 2021), but this tool does not capture underlying biological vulnerabilities within the neonate, such as epigenetic factors. Consequently, there is an unmet need for biomarkers to proactively identify neonates at high-risk and low-risk for NOWS development to improve observation, treatment, and outcomes for infants with POE.

microRNAs (miRNAs) are small non-coding RNA molecules that intracellularly regulate RNA translation (Ambros, 2004; Bartel, 2004) but also can be released extracellularly, including into the circulation, where they are thought to be a mechanism of cell-to-cell communication (Bär et al., 2019). Extracellular miRNA profiles are altered by opioid exposure. A study in healthy adult male volunteers found 96 plasma circulating miRNAs altered by 24 h of either hydromorphine or oxycodone exposure, with 27% of these miRNAs altered similarly by both drug exposures (Toyama et al., 2017). Extracellular serum miRNAs were found to differentiate alcohol- and opioid-using pregnant women from alcohol- and opioid-naïve pregnant women (Gardiner et al., 2016). Circulating miRNAs have also been shown to be predictive of outcomes following prenatal exposures and potentially mediators of the effects of prenatal exposures. The inventors previously found that plasma miRNAs assessed at mid-pregnancy could predict future adverse birth outcomes following alcohol exposure, i.e., identify infants with neurobehavioral and growth deficits associated with fetal alcohol spectrum disorders from unaffected infants (Balaraman et al., 2016; Salem et al., 2020). These maternal miRNAs that were predictive of infant outcomes were shown preclinically to produce placental and fetal growth deficits, recapitulating, in the absence of alcohol, the intra-uterine growth restriction seen with prenatal alcohol exposure (Tseng et al., 2019). Recently, the inventors have shown that plasma miRNAs in early infancy can also be predictive of growth deficits and neurobehavioral outcomes following prenatal alcohol exposure (Mahnke et al., 2021b). These studies show that extracellular miRNA expression is altered by prenatal drug exposures and can be indicative of future adverse health outcomes.

The primary objective of the study which led to the present invention was to determine if extracellular plasma miRNAs, derived from the umbilical cord at birth, could be used to predict the existence and severity of NOWS, indicated the need for pharmacologic treatment with opioids (with or without other agents and length of hospital stay for a neonate. The inventors hypothesized, given their previous research showing that circulating miRNAs could predict infant outcomes following ethanol exposure, that neonatal circulating miRNAs would have predictive value for both metrics of NOWS severity.

In utero exposure to opioids and medication for opioid use disorders (MOUD) can result in Neonatal Opioid Withdrawal Syndrome (NOWS), which now affects 6 in every 1,000 hospital births. There is a broad variability in the onset and severity of NOWS, and decisions about treatment for NOWS are typically delayed until the onset of withdrawal symptoms. In the present application, the inventors assess if miRNAs within the circulation of a neonate (in particular, umbilical cord blood) can serve as biomarkers to proactively identify opioid/MOUD exposed neonates at risk of developing NOWS. From a prospective cohort study, ENRICH at the University of New Mexico (UNM), cases (infants Pharmacologically-Treated for NOWS) and controls (Not-Pharmacologically Treated) were identified. Using quantitative real-time PCR (qPCR), the inventors assessed the levels of 179 unique miRNAs that were present in circulation (cord blood) both intra- and extracellularly, in plasma and leukocytes, respectively. NOWS cases had substantially longer hospitalization compared to controls (19.5 vs. 6.0 days; $p<0.001$). Preliminary analysis of miRNA expression from 58 neonates (58 plasma samples and 33 leukocyte samples, with 28 of the plasma/leukocyte samples derived from the same neonate) showed a large number of the miRNAs assessed are present in >80% of samples (171 in plasma, 110 in leukocytes). Effect size estimates indicate that a number of miRNAs are differentially expressed between treated-for-NOWS and non-treated-for-NOWS infants, with some miRNAs altered with a large effect size (Cohen's $d>0.8$). Interestingly, only one of these miRNAs is altered with a large effect size in both plasma and leukocytes, indicating that unique profiles of miRNAs are altered intra- and extra-cellularly. Additionally, the miRNAs altered in leukocytes may be reflective of altered intracellular biology or subpopulation composition. These data indicate that leukocytes are not the only or primary source of plasma circulating miRNAs. Due to the higher variability in leukocyte miRNAs, likely due to changes in subpopulation proportion, the inventors have further examined plasma miRNAs, which are easier to isolate and provide more reliable expression profiles.

The present invention attempts to address this recurring and growing problem by providing a diagnostic method for predicting NOWS in neonates and taking steps very shortly after the birth of an effected neonate to treat the neonate opioid withdrawal symptoms and minimize deleterious impact on the child. It is noted that the longer after the birth of the child that therapy for NOWS is initiated, the greater the likelihood that permanent damage (principally neurological) will occur in the neonate.

BRIEF DESCRIPTION OF THE INVENTION

Pursuant to the present invention, the inventors have provided a method to assess if miRNAs, obtained from neonatal sources including but not limited to placental/umbilical cord blood, can serve as biomarkers to proactively identify opioid/MOUD exposed neonates at risk of having or developing NOWS. From a prospective cohort study, ENRICH at UNM. discussed above, cases (infants treated-for-NOWS) and controls (not-treated-for-NOWS) were identified. Using qPCR, the inventors assessed the levels of 179 unique miRNAs that were present in circulation (cord blood) both intra- and extracellularly, in plasma and leukocytes, respectively. Preliminary analysis of miRNA expression from 58 neonates (58 plasma samples and 33 leukocyte samples, with 28 of the plasma/leukocyte samples derived from the same neonate) showed a large number of the miRNAs assessed are present in >80% of samples (173 in plasma, 110 in leukocytes). Effect size estimates indicated that a number of miRNAs are differentially expressed between infants pharmacologically treated-for-NOWS and not-treated-for-NOWS infants, with some miRNAs altered with a large effect size ($d>0.8$). Interestingly and unexpectedly, only one of these miRNAs is altered with a large effect size in both plasma and leukocytes, indicating that unique profiles of miRNAs are altered intra- and extra-cellularly. Additionally, the miRNAs altered in leukocytes may be reflective of altered intracellular biology or subpopulation composition. These data indicate that leukocytes are not the only or primary source of plasma circulating miRNAs. Due to the higher variability in leukocyte miRNAs, likely due to changes in subpopulation proportion, the inventors have further examined plasma miRNAs, which are easier to isolate and provide more reliable expression profiles, thus providing insight into neurodevelopmental outcomes which will also be measured in this cohort and provide additional insight into therapy for NOWS once the neonate is born.

Pursuant to the present invention a sample of blood is obtained from a neonate's umbilical cord and the cord blood is analyzed for the altered expression of miRNA using methods which are standard (qPCR, miRNA arrays, RNA-Seq, multiplex miRNA profiling, etc. with qPCR analysis more often used). In the present invention, at least three (3) miRNA as presented and described herein and up to the 51 miRNA (see FIGS. 28 and 31), which have been identified as being associated with severe NOWS are analyzed for their presence and concentration in plasma derived from blood from neonatal sources including but not limited to placental/umbilical cord blood, and compared to a standard for each of the miRNA analyzed (e.g., the standard is a known concentration of miRNA in the umbilical cord blood derived plasma in the neonates prenatally exposed to opioids who do not develop severe NOWS requiring pharmacologic treatment or prolonged hospitalization) to identify NOWS in a neonate in order to determine the appropriateness of pharmacological treatment and/or long-term hospital stay or alternatively, to monitor therapy in a neonate undergoing therapy for NOWS.

Of the above 51 described miRNA (see also FIGS. 28 and 31), measuring at least three miRNA (hsa-miR-128-3p SEQ ID NO:3 for up-regulation, hsa-miR-421 SEQ IDO NO:18 for up-regulation and hsa-miR-30c-5p SEQ ID NO:14 for down-regulation) in umbilical cord blood and comparing the concentrations of the miRNA with a standard (such that the measured concentration of the miRNA is above or below a standard as set forth in FIG. 26 hereof) can be used to predict at high accuracy that a neonate does or does not have NOWS severe enough to implement pharmacological treatment and long-term hospital stay in order to treat the diagnosed neonate. The first three miRNA described above which are analyzed may be supplemented with analysis of miRNAs from the list of 51 miRNAs in order to increase the reliability of the diagnosis for implementation of treatment. Tables 7 and 8 of FIGS. 29 and 30 provide additional miRNAs which are often used to supplement the list of the three miRNAs presented above to increase the accuracy of the diagnosis. In addition to diagnosing NOWS and establishing a treatment option for the neonate diagnosed with NOWS, the analysis of miRNAs may be used also to monitor the progress of pharmacological treatment of the neonate diagnosed with NOWS and/or the point in a long-term hospital stay where the neonate is well enough or is estimated to be well enough to be released from intensive care and/or from the hospital in general. Thus, the method of the present invention may be used to accurately predict the diagnosis and treatment options for neonates with NOWS and to assist in monitoring therapy of the neonate with NOWS to favorable effect.

In a first embodiment, the present invention is directed to a method for diagnosing the existence of NOWS in a neonatal patient or subject in need comprising obtaining a blood sample from umbilical cord at birth or soon thereafter and analyzing the blood sample for the concentration of three miRNAs to determine the presence of NOWS in the patient or subject: hsa-miR-128-3p (SEQ ID NO:3) which is overexpressed or up-regulated compared to a standard (often, a standard obtained from a population of neonates without NOWS), hsa-miR-421 (SEQ ID NO:18) which is also overexpressed or up-regulated compared to a standard and hsa-miR-30c-5p (SEQ ID NO:14) which is under-expressed or down-regulated compared to a standard to provide a diagnosis of NOWS in said patient or subject, wherein the diagnosis of NOWS is accompanied by treatment comprising pharmacological treatment as soon as is practical after the diagnosis and/or a hospital stay of at least 14 days, often both pharmacological treatment and long-term hospital stay.

In an embodiment. the analysis of the three miRNAs described above is supplemented with a further analysis of two miRNAs, specifically hsa-miR-let-7d-5p (SEQ ID NO:26) which is under-expressed or down-regulated compared to a standard and hsa-miR-584-5p (SEQ ID NO:23) which is overexpressed or up-regulated compared to a standard (in total, five miRNAs are measured in this embodiment) in order to diagnose or predict at high accuracy (approximately 90-94% or greater) NOWS with a recommendation for pharmacological treatment.

In alternative embodiments, the analysis of the five miRNAs above is supplemented with a further analysis of one or two miRNAs selected from the group consisting of hsa-miR-629-5p (SEQ ID NO:24, up-regulated) and hsa-miR-223-5p (SEQ ID NO:32, down-regulated) compared to a standard (in total, six or seven miRNAs are measured in this embodiment) in order to diagnose or predict at high accuracy (approximately 90-95% or greater) NOWS with a recommendation for pharmacological treatment.

In additional embodiments, the analysis of seven miRNAs as described above, i.e., hsa-miR-128-3p (SEQ ID NO:3, up-regulated), hsa-miR-421 (SEQ ID NO:18, up-regulated), hsa-miR-30c-5p (SEQ ID NO: 14, down-regulated), hsa-miR-let-7d-5p (SEQ ID NO:26, down-regulated), hsa-miR-584-5p (SEQ ID NO: 23, up-regulated), hsa-miR-629-5p (SEQ ID NO:24, up-regulated) and hsa-miR-223-5p (SEQ ID NO:32, down-regulated) is supplemented with a further analysis of from 1-4 (one, two, three or four, often four) miRNAs selected from the group consisting of hsa-miR-495-3p (SEQ ID NO:22, up-regulated), hsa-miR-652-3p (SEQ ID NO:15, up-regulated), hsa-let-7b-5p (SEQ ID NO:1, down-regulated) and hsa-miR-146b-5p (SEQ ID NO:28, down-regulated) compared with a standard (in total, from 8-11 miRNAs are measured in this embodiment) in order to diagnose or predict at high accuracy (approximately 90-96% or greater) NOWS with a recommendation for pharmacological treatment.

In a further embodiment, the analysis of three miRNAs hsa-miR-128-3p (SEQ ID NO:3, up-regulated), hsa-miR-421 (SEQ ID NO:18, up-regulated) and hsa-miR-30c-5p (SEQ ID NO: 14, down-regulated), is supplemented with a further analysis of hsa-let-7b-5p (SEQ ID NO1: down-regulated) and hsa-miR-10b-5p (SEQ ID NO:38, down-regulated) compared with a standard (in total five miRNAs are measured in this embodiment) in order to diagnose or predict at high accuracy (approximately 90-97% or greater) NOWS with a recommendation for longer term (≥14 days) hospital stay.

In yet an additional embodiment, the analysis of five miRNAs hsa-miR-128-3p (SEQ ID NO:3, up-regulated), hsa-miR-421 (SEQ ID NO:18, up-regulated), hsa-miR-30c-5p (SEQ ID NO:14, down-regulated, hsa-let-7b-5p (SEQ ID NO:1 down-regulated) and hsa-miR-10b-5p (SEQ ID NO:38, down-regulated) is supplemented with a further analysis of from one to six (one, two, three, four, five or six) miRNAs selected from the group of miRNAs consisting of hsa-miR-103a-3p (SEQ ID NO:37, up-regulated), hsa-miR-146a-5p (SEQ ID NO:41, up-regulated), hsa-miR-382-5p (SEQ ID NO:17, up-regulated), hsa-miR-484 (SEQ ID NO:21, up-regulated), hsa-miR-495-3p (SEQ ID NO:22, up-regulated) and hsa-miR-21-5p (SEQ ID NO:6, down-regulated) compared with a standard (in total from six to eleven miRNAs are measured in this embodiment) in order to diagnose or predict at high accuracy (approximately 95-99% or greater) NOWS with a recommendation for longer term (≥14 days) hospital stay.

In yet an additional embodiment, the analysis of three miRNAs hsa-miR-128-3p (SEQ ID NO:3, up-regulated), hsa-miR-421 (SEQ ID NO: 18, up-regulated) and hsa-miR-30c-5p (SEQ ID NO: 14, down-regulated) to establish NOWS in a neonatal patient requiring pharmacological treatment and/or long-term (≥14 days) hospital stay is supplemented with a further analysis of from one to twenty-two additional miRNAs (i.e., any 1, any 2, any 3, any 4, any 5, any 6, any 7, any 8, any 9, any 10, any 11, any 12, any 13, any 14, any 15, any 16, any 17, any 18, any 19, any 20, any 21 or all 22 remaining miRNAs, excluding SEQ ID NOs: 3, 18 and 14, above), from the list of miRNAs of SEQ ID NOs 1-25 of FIG. 26 exhibiting up-regulation or down-regulation as indicated in FIG. 26) to further increase the accuracy of the prediction of NOWS requiring pharmacological treatment and/or long-term hospital stay, often both pharmacological treatment and long-term hospital stay.

In still a further embodiment, the invention is directed to an analysis of five miRNAs hsa-miR-128-3p (SEQ ID NO:3, up-regulated), hsa-miR-421 (SEQ ID NO:18, up-regulated), hsa-miR-30c-5p (SEQ ID NO: 14, down-regulated), hsa-miR-let-7d-5p (SEQ ID NO:26, down-regulated) and hsa-miR-584-5p (SEQ ID NO:23, up-regulated) to establish NOWS in a neonatal patient requiring pharmacological treatment is supplemented with a further analysis of from one to nine additional miRNAs from the list of miRNAs of SEQ ID NOs 27-35 of FIG. 26 exhibiting up-regulation or down-regulation as indicated in FIG. 26 to increase the accuracy of the prediction of NOWS in a neonatal patient requiring pharmacological treatment.

In yet a further embodiment, the analysis of three miRNAs hsa-miR-128-3p (SEQ ID NO:3, up-regulated). hsa-miR-421 (SEQ ID NO:18, up-regulated) and hsa-miR-30c-5p (SEQ ID NO: 14, down-regulated) to establish NOWS in a neonatal patient requiring long-term (≥14 days) hospital stay is supplemented with a further analysis of from one to sixteen additional miRNAs from the list of miRNAs of SEQ ID NOs 36-51 of FIG. 26 exhibiting up-regulation or down-regulation as indicated in FIG. 26 to further increase the accuracy of the prediction of NOWS requiring long-term hospital stay.

In yet another embodiment, the invention is directed to an analysis of all 51 miRNAs presented in FIG. 26 (following FIG. 26 as to whether or not a miRNA is up-regulated or down-regulated compared to a standard for analysis) to establish NOWS in a neonatal patient requiring both pharmacological treatment and/or long-term hospital stay at very high accuracy.

Pursuant to the above-described methods. as the presence of NOWS in the neonate is confirmed (once diagnoses and a determining of NOWS and recommended therapy or long-term hospital stay is made), the neonate will be recommended for and then undergo NOWS (e.g. opiate withdrawal) therapy whereupon the diagnosed neonate is treated with one or more of effective amounts of buprenorphine, methadone, morphine, tincture of opium and mixtures thereof, which treatment may further include barbiturates (e.g. phenobaritol), clonidine, selective serotonin reuptake inhibitors (SSRIs) and benzodiazepines as alternative or additional agents and/or placed in long-term care in a hospital facility. Non-pharmacological NOWS intervention as described herein is often used to treat the neonate during a patient or subject's long-term hospitalization. NOWS pharmacological therapy is standard and typically utilizes one or more opiates in effective amounts (often less than 1 mg to up to 5-10 mg or more per day) in order to resolve and/or reverse NOWS. The duration of therapy for NOWS is usually 2-3 weeks or for that period which results in substantial attenuation of withdrawal and related neurological symptoms in the neonate (see opiate withdrawal symptoms of NOWS herein below). Duration of therapy may last for as little as 1-2 days to a month or more.

In addition to diagnosing for NOWS in a neonate, the method of the present invention also may be used to monitor therapy for NOWS in the neonate once therapy has commenced. In this method, the concentration of miRNA is measured over time (generally, at least once, and preferably more than once, often up to five or more times during therapy) and the concentration of miRNA in the blood (plasma or cellular fraction, often the plasma fraction) of a neonate being treated is compared with a standard, often a standard of the neonate before treatment has commenced and/or of a neonate or population of neonates without NOWS or having been successfully treated for NOWS, such that a decision may be made to continue therapy, discontinue therapy or modify therapy in the treated neonate. In many instances, the monitoring of therapy will measure the same miRNAs measured in making the original diagnosis of NOWS in the neonatal patient or subject as described herein above. Alternatively, the method for monitoring will measure at least one miRNA and often at least 3-5 miRNAs, 6-10 miRNAs, 11-15 miRNAs or 15-20+ miRNAs from the list of miRNAs 1-51 of FIG. 26 hereof to see if the measured miRNA is moderating to a normal level during and/or after therapy. In this method, an absence of favorable therapeutic progress will be made if similar concentrations of the same miRNAs used to make the original diagnosis remain unchanged from the original diagnosis. Favorable progress in or even an end to therapy may be established by measuring the same miRNAs used for the NOWS diagnosis described above (the miRNAs used to monitor therapy are often the same miRNAs used to make the original diagnosis and treatment recommendations as described herein above) and comparing those measurements with a standard of the neonate before treatment, or a standard from a neonate or population of neonates without NOWS or having recovered from NOWS, wherein a measurement of miRNAs in the treated patient or subject which indicates improved concentrations of miRNAs to those from the neonate before treatment or from neonates without NOWS or who have recovered from NOWS is evidence of favorable treatment progress or the ability to cease pharmacological treatment. Alternatively, at least one, often 3-5, 6-10, 11-15, 15-20 or more and up to 35 miRNA biomarkers from the list of miRNA biomarkers 1-35 of FIG. 26 may be used to monitor pharmacological therapy and at least one, often 3-5, 6-10, 11-15, 15-20 or more and up to 41 miRNA biomarkers from the list of miRNA biomarkers 1-25 and 36-51 of FIG. 26 may be used to monitor hospital stay. In each instance, when the biomarkers normalize to levels exhibited by the standard, effective therapy is occurring or has occurred. In each instance, when the miRNA biomarkers remain significantly elevated or reduced compared to the standard (e.g. pursuant to the original diagnosis of NOWS), a modification of therapy should be undertaken.

The following conclusions and characteristics are relevant to the present application:

Intra- and extra-cellular miRNAs are differentially expressed in infants receiving pharmacological treatment compared to infants receiving pharmacological treatment for NOWS;

Leukocytes are not the primary source for circulating plasma miRNAs;

Intra- and extra-cellular miRNAs implicate different biological pathways;

Plasma: Organism (liver, vascular) development;

Leukocyte: Cell cycle and hematological development;

Intra- and extra-cellular miRNAs may indicate NOWS vulnerability prior to symptoms; and Intra- and extra-cellular miRNAs implicate perturbation of novel growth and developmental pathways in treated-for-NOWS infants.

BRIEF DESCRIPTION OF THE FIGURES

FIG. 13 shows Table 1 which presents the area under the curve (AUC), representing sensitivity/specificity among all cutoff points, for the batteries of 1-6 miRNAs, as well as parameter estimate (β), standard error (se), and corresponding p-value from logistic regression. A combination of 3 miRNAs (hsa-miR-652-3p, hsa-miR-365a-3p, and hsa-let-7b-5p) achieved AUC=0.869 (95% CI: 0.76; 0.98). Addition of hsa-miR-423-5p, hsa-miR-20a-5p, and hsa-miR-222-3p improved AUC to 0.881 (95% CI: 0.77; 0.99). Addition of gestational age further improved AUC to 0.911.

FIG. 16, Table 2 shows a list of miRNAs that are associated with NOWS diagnosis or hospital stay. miRNAs in bold were significantly altered (p<0.05) in preliminary analysis while the additional miRNAs approached significance.

FIG. 19, Table 3 shows the material socio-demographic, medical characteristics and substance use patterns of the individuals involved in the study set forth in example 4, hereof.

FIG. 20, Table 4 shows perinatal and infant characteristics of subjects in the study presented in example 4, hereof.

FIG. 21, Table 5 shows the expression of miRNA candidates (at p<0.10) for predictive models.

FIG. 22, Table 6 shows predictive model performance. This table provides the results of forward step-wise logistic regression analysis evaluating predictive ability of the expression of these miRNAs on prolonged hospitalization after adjusting for gestational age and additionally MOUD.

FIG. 26 shows a complete list of the 51 miRNAs which are relevant to the present invention and can be used to diagnose NOWS in a neonate and the advisability/requirement of pharmacological treatment and/or long-term hospital stay (at least 14 days). This figure also identifies the sequence of each miRNA, the MIMAT number for each sequence, the relevance of the miRNA to the diagnosis of NOWS and therapy (both pharmacological treatment and/or long term hospitalization) of the diagnosed neonate and whether the relevance of the individual miRNA to the diagnosis and/or monitoring of therapy is expressed as an overexpression (up-regulation, in bold print) or underexpression (down-regulation, in italicized print) of the miRNA which would support the diagnosis of NOWS and treatment recommendation. Thus, if one were to analyze for example, miR-128-3p (SEQ ID NO:3), the overexpression or up-regulation of that miRNA in a neonate blood sample, preferably a plasma sample obtained from umbilical cord or placental blood would be predictive of NOWS. The same would be true for the other miRNAs which are listed in bold accordingly in FIG. 26. Likewise. if one were to analyze for example, miR-30c-5p (SEQ ID NO:14), the underexpression or down-regulation of that miRNA in a neonatal blood sample would be predictive of NOWS, as would similar miRNAs listed in italics in FIG. 26.

FIG. 27, Table 7 shows analyses for the identification of miRNAs from the list of 51 relevant miRNAs (FIGS. 26 and 29) tiered for relevance for the diagnosis of NOWS in a neonate. Using the selection criteria, 51 potential miRNA were identified for at least one of the two outcomes, pharmaceutical treatment (n=35) or LOS≥14 days (n=41). Final miRNA signature (identified using a stepwise logistic regression model) resulted in 5 miRNAs for each of NOWS outcomes (3 miRNAs were common across both outcomes)—Tier A. The '2$^{nd}$ tier' (Tier B) models identified additional 6 miRNA for each NOWS outcome and the 3$^{rd}$ Tier (Tier C) identified additional miRNAs, as presented in Table 7. Ultimately, the Tier C final predictive models included 4 miRNA for pharmaceutical treatment and 6 miRNA for LOS≥14 days.

FIG. 28, Table 8 shows the validity indices associated with miRNA clusters for all tier Models based upon the performance of tiered miRNA clusters, in combination, for predicting NOWS outcomes. In a predictive model for receipt of pharmacologic treatment including predicted probabilities from the 3 Tier group models (A, B, and C), Tier Group C was not significant (p=0.80). In a model that included miRNAs from Tier Group A and B, the resultant AUC was 0.963 (bias-adjusted AUC=0.920), p<0.05. In a predictive model for LOS≥14 days, Tier Group B was not significant (p=0.76). In a model that included miRNAs from Tier Group A and C, the resultant AUC 0.998 (bias-adjusted AUC=0.98), p<0.10. Thus, Table 8 shows performance for all three tiers and as well as after dropping non-significant tiers (which do not significantly improve model performance beyond the tiers already in the model). * Included in the prediction model are the predicted probability estimates associated with each of the Tier groups. The parameter estimates represent the increase (decrease) associated with the probability of the outcome (pharmacologic treatment or LOS≥14 days) for each unit increase in estimated probability for the Tier (For example, for the Tier A, B, C pharmacologic treatment model, an increase of 1% in estimated probability from Tier A increases the probability of pharmacologic treatment by 4.69.)

FIG. 29 shows a list of all 51 miRNAs which are relevant in diagnosing NOWS in neonates at risk and establishing therapeutic intervention in treating NOWS pursuant to the present invention. Also shown are each of their RNA sequences and SEQ ID NOs.

FIG. 1S, Supplementary Table S1 shows the miRNA primers altered between panel versions as two proof-of-concept samples were included in the analysis and had been run on earlier panel versions.

FIG. 3S, Supplementary Table S3 shows miRNA expression, effect size, and significance for comparing all samples, and by MOUD for treatment for NOWS.

FIG. 4S, Supplementary Table S6 shows a predictive model construction and performance.

DETAILED DESCRIPTION OF THE INVENTION

Figure 1:
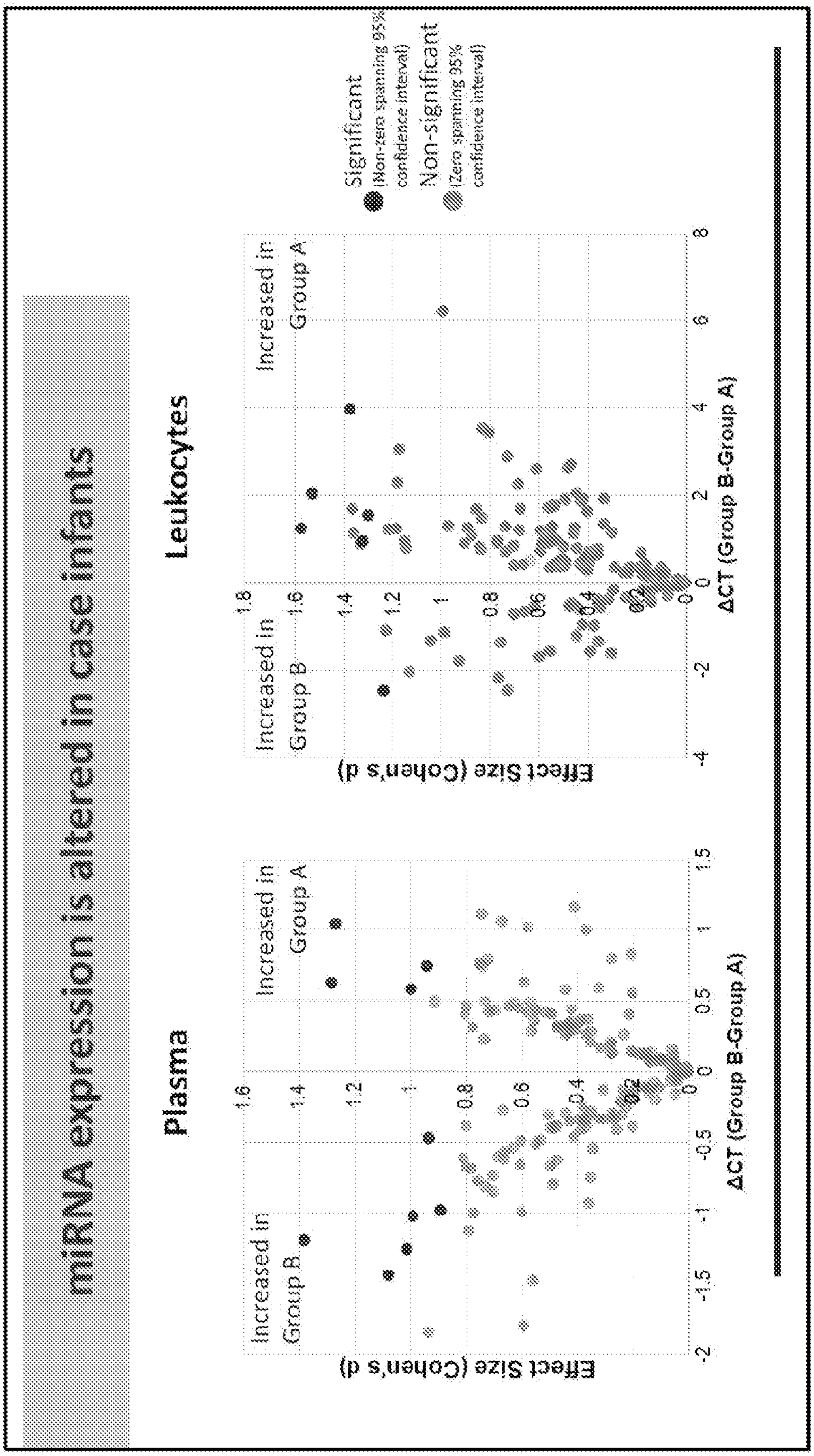
FIG. 1 shows in a preliminary sample, a number of miRNAs show differential expression between groups at a large effect size (Cohen's d>0.8). A subset of miRNAs are significantly altered between groups, with a non-zero spanning 95% confidence interval (maroon).
Figure 2:
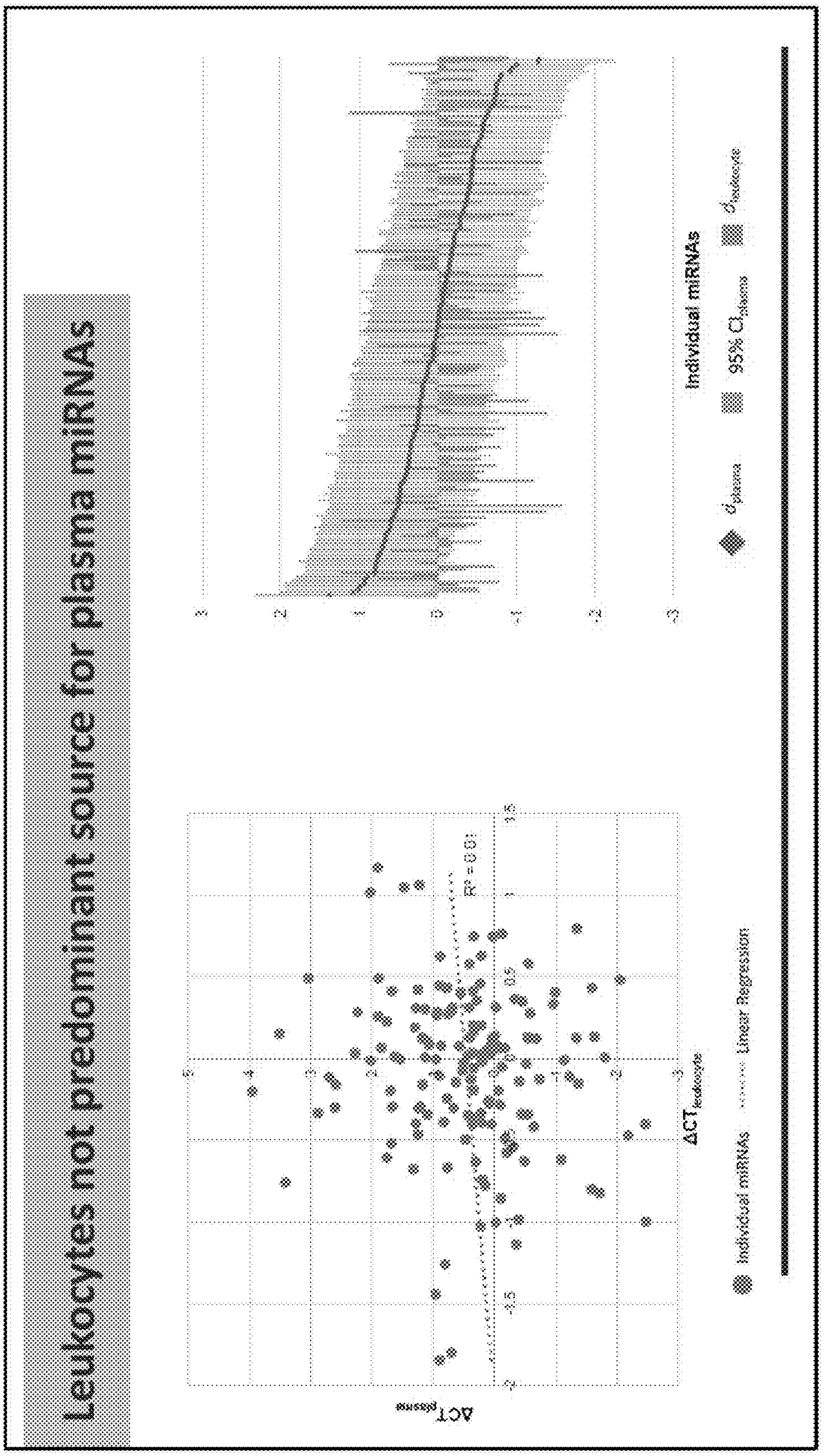
FIG. 2 shows Left: Plotting the change in cycle threshold for an individual miRNA in plasma verses the change in leukocytes shows that there is no overall linear relationship between changes in expression in the leukocytes and the plasma. Right: The alteration in miRNA expression in the plasma is shown from the most positive Cohen's d effect size (left) to most negative (right, blue diamonds). The 95% confidence interval of these effect sizes are shown in gray shading. The majority of miRNAs show a negative effect size in leukocytes (orange), with many miRNAs altered in opposite directions in plasma in comparison to leukocytes.
Figure 2S:
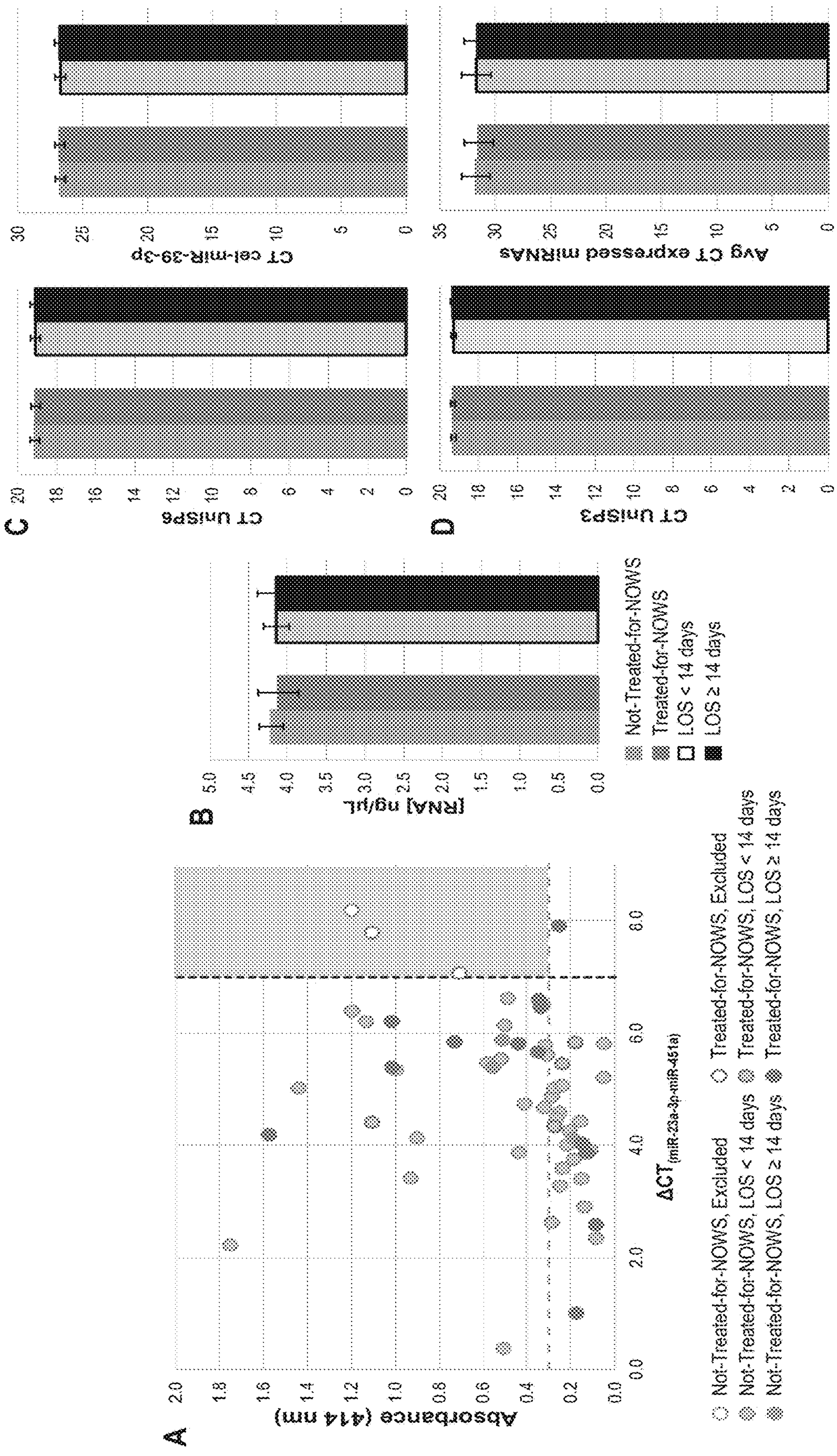
FIG. 2S shows RNA isolation metrics. (A) Comparison of hemolysis detection metrics of absorbance at 414 nm and expression of erythrocyte-enriched miRNA ($\Delta CT_{(miR\text{-}23a\text{-}3p-miR\text{-}451a)}$). Gray region indicates samples which were positive for both hemolysis measures and excluded from further analysis. (B) Total RNA concentration in plasma samples including the addition of carrier MS2 phage RNA. (C) Expression of spike-in miRNAs to detect reverse transcriptase and polymerase inhibition. (B) Plate performance metrics including expression of interpolate control (UniSP3) and average CT of expression for miRNAs.
Figure 3:
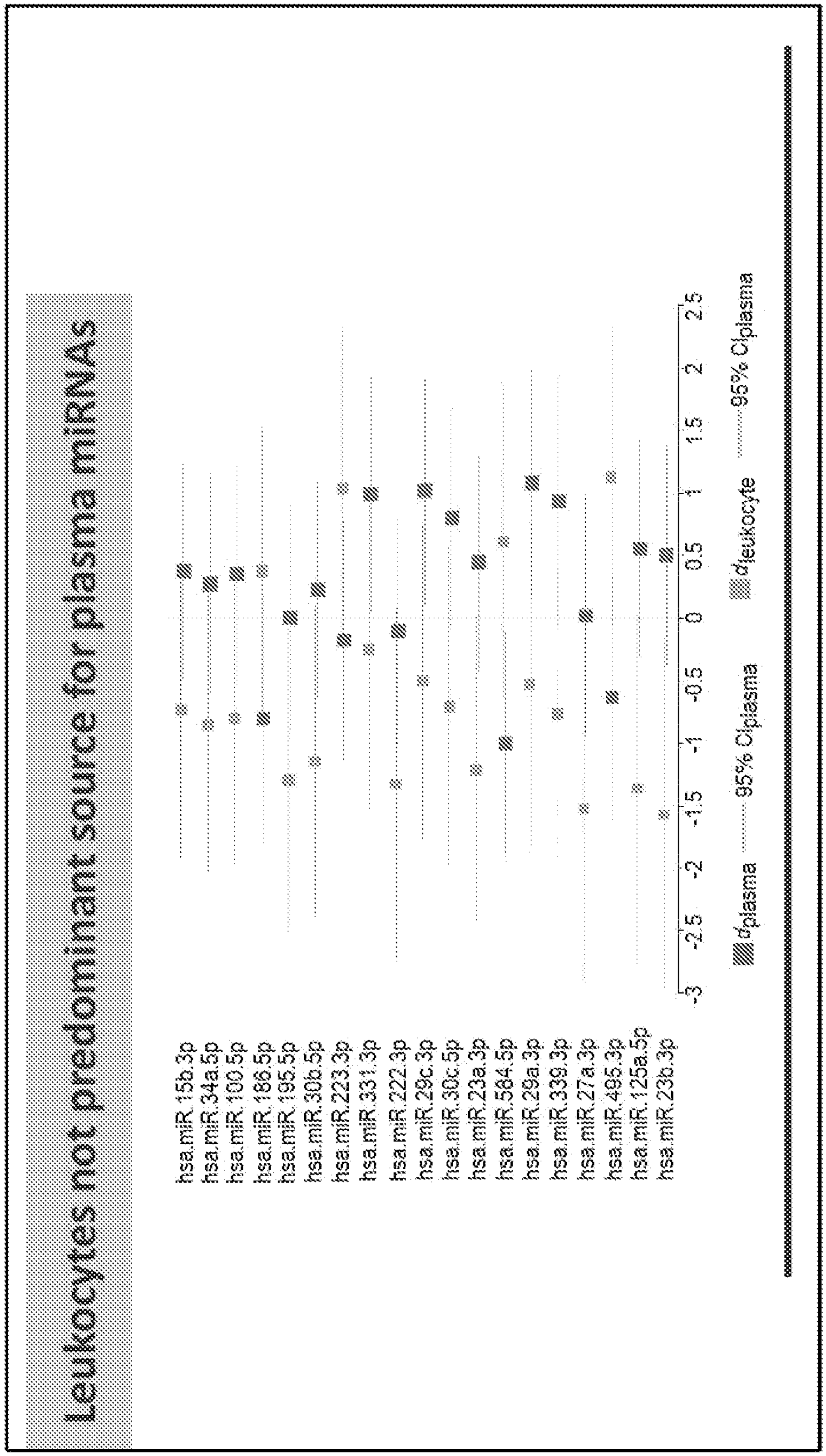
FIG. 3 shows further results evidencing that there is no overall linear relationship between changes in expression in the leukocytes and plasma.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "about" is used throughout the specification to describe an amount which is presented and up to 10% more or less than the amount which is specifically presented within the context of its use.

The term "patient" or "subject" is used throughout the specification to describe a neonate, most often a human neonate to whom treatment, including prophylactic treatment, with the compositions according to the present invention is provided (a patient or subject in need). For treatment of those infections, conditions or disease states (e.g. NOWS) which are specific for a patient or subject such as a human patient, the term patient refers to that specific animal. In many instances, diagnostic methods are applied to patients or subjects who are suspected of having opioid withdrawal syndrome and the diagnostic method is used to assess the severity of the disease state or disorder.

The term "blood sample" or "neonatal blood sample" is used to describe any blood sample obtained from a neonate at any time after birth. In rare instances, a blood sample may be obtained from a fetus prior to birth. Often, the blood sample is obtained from the umbilical cord or placenta. The blood is often separated into two fractions, a plasma fraction and a cellular fraction. Both the plasma fraction and the cellular fraction contain miRNAs which can be analyzed for miRNA content (type and concentration). Often, in the present invention, the plasma fraction of umbilical cord blood is used for analyzing miRNA content.

The term "compound" is used herein to refer to any specific chemical compound disclosed herein and in particular, an opioid or other agent which is used and is effective in the treatment or resolution of NOWS. Within its use in context, the term generally refers to a single small molecule as disclosed herein, but in certain instances may also refer to other forms of the compound. The term compound includes active metabolites of compounds and/or pharmaceutically acceptable salts (including alternative pharmaceutically acceptable salts) thereof. Also included under the term "compound" are stereoisomers (e.g., diastereoisomers, enantiomers), solvates (including hydrates) and polymorphs.

The term "effective amount" is used throughout the specification to describe concentrations or amounts of formulations or other components which are used in amounts, within the context of their use, to produce an intended effect according to the present invention, most often to treat NOWS or opioid withdrawal syndrome in neonates pursuant to the present invention. The formulations or component(s) may be used to produce a favorable change in a disease or condition treated, whether that change is a remission of the effects of a disease state or condition, a favorable physiological result, a reversal or attenuation of a disease state or condition treated, the prevention or the reduction in the likelihood of a condition or disease-state occurring, depending upon the disease or condition treated. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from about 0.001 mg/kg to about 15 mg/kg or more, about 0.01 mg/kg to about 10 mg/kg, about 0.1 to about 5 mg/kg, about 1 mg to about 10 mg/kg per day and as otherwise described herein. The person of ordinary skill may easily recognize variations in dosage schedules or amounts to be made during the course of therapy.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence of disease in one or more patients within that population of all patients, rather than prevent, in all patients, the occurrence or recurrence of a disease state.

The term "pharmaceutically acceptable" refers to a salt form or other derivative (such as an active metabolite or prodrug form) of the present compounds or a carrier, additive or excipient which is not unacceptably toxic to the subject to which it is administered.

"Treat", "treating", and "treatment", etc., as used herein, refer to any action providing a benefit to a patient at risk for or afflicted with a disease, including improvement in the condition through lessening or suppression of at least one symptom, delay in progression of the disease, reduction in the likelihood or delay in the onset of the disease, etc. Treatment, as used herein, may encompass both therapeutic and prophylactic treatment, but is typically therapeutic, depending on the context of the treatment. Treatment of NOWS may be pharmacologically based or non-pharmacologically based.

The term "miRNA analysis" is used to describe the method used to identify (verify) and quantify the miRNA in the neonate blood sample, especially an umbilical cord or placental blood sample in order to establish a diagnosis of NOWS. In preferred aspects, the present invention often makes use of a miRNA qPCR assay. Alternative assays may be used for identifying and quantifying miRNA in a sample. One of the most popular techniques for validating and accurately quantifying miRNAs is quantitative real time PCR (qPCR). This technique begins with the conversion of miRNA to cDNA. With the length of a miRNA being comparable to that of a typical DNA primer, cDNA synthesis from miRNAs presents its own challenges. The solution to this is to make the molecule longer, either by incorporating a poly(A) tail or stem-loop structure. Once the miRNA has been converted to cDNA it can be assayed using the same approach as a conventional qPCR experiment. Amplification is initiated with an miRNA-specific primer and a stem-loop/poly(A) primer. Either SYBR® Green or a TaqMan® probe are preferably used to detect the amplified product. In addition, Firefly™: a new multiplex platform for miRNA profiling may be used to identify and quantify miRNA in the present invention. In addition, Firefly™ technology can use Multiplex Cellular and Multiplex Circulating miRNA Assays that allow detection of up to 70 miRNAs simultaneously within multiple samples, allowing researchers to identify and quantify miRNA pursuant to the present invention quickly and conveniently.

Alternative methods for identifying and quantifying miRNA in an umbilical cord sample include miRNA arrays, RNA-seq assay and multiplex miRNA profiling, all using methods which are well known in the art.

The following provides an exemplary approach which can be used clinically to identify miRNAs in neonatal blood samples. Per national guidelines, infants born to women who used opioids during pregnancy are monitored (72-96 hours) in the hospital for signs of NOWS. Yet NOWs can present anywhere from birth to 7 days or more from birth, leading in some cases to costly readmissions after release. The Finnegan Neonatal Abstinence Scoring System (FNASS) is the main method for assessing opioid exposed infants for NOWS and is based on 31 opioid withdrawal related indicators, which are weighted. Other tools include the Neonatal Narcotic Withdrawal Index, the Ostrea tool, and the Eat, Sleep, Console (ESC) scoring and intervention system. However, subjective assessment of symptoms (such as quality of crying) by nurses administering these tools leads to widespread variation in scoring. The inability to reliably discriminate between infants at low and high risk for NOWS requires low-risk infants to stay 3-4 days in the hospital for observation. This is not only costly but can also disrupt maternal-infant bonding known to adversely affect long-term neurodevelopmental outcomes. Variability in the presentation of signs has led to treatment decisions being delayed until the onset of withdrawal symptoms. Yet, delays in pharmacologic treatment lead to the risk of increased infant morbidity. Current clinical tools to identify infants needing pharmacological treatment for NOWS are reactive rather than proactive, and current treatment guidelines of NOWS are far from optimal.

Accurate risk stratification shortly after birth will allow low-risk infants to be discharged from the hospital earlier, which will result in substantial healthcare cost savings. Identification of high-risk infants will inform decisions about most appropriate clinical monitoring and access to care (e.g., timely transfer of high-risk infants from rural/underserved areas to tertiary care facilities) as well as treatment approaches. Accurate identification of high-risk infants before manifestation of NOWS symptoms will allow for an improved treatment model (e.g., initiation of the second-line therapy with clonidine or other adjunctive agents sooner) which is expected to result overall in a shorter weaning protocol and shorter hospitalization.

The biomarker-based technology of the present invention is intended to improve clinical management of NOWS and improve short- and long-term outcomes of the growing number of infants who are afflicted with this condition.

Tests for plasma miRNAs typically will utilize standardized polymerase chain reaction (PCR) methodology as outlined in detail in two previous publications (Balaraman et al., 2016; Mahnke et al., 2021a). This methodology is routinely available in clinical, CLIA-certified laboratories. The final form of the test will be adapted to the equipment needed and can include microwell plate and microfluidics cartridge formats. Standardized protocols often include:

1. Collection of infant cord blood in EDTA-coated collection tubes.
2. Separation of blood into plasma and cellular phases.
3. Assessment of plasma purity by light absorbance at 414 nm for a target absorbance of less than 0.3 absorbance units.
4. Isolation of total RNA using standardized methodologies and kits (for example, miRNeasy mini kit, Qiagen Sciences, Germantown, MD or equivalent).
5. cDNA is synthesized from 6.25 ng RNA, diluted to 5 ng/μL using nuclease free water, in a 10 μL cDNA reaction mixture using the miRCURY LNA RT Kit (Qiagen Sciences, Germantown, MD) or equivalent.
6. miRNAs are assessed using a qRT-PCR or equivalent protocol for multiplexed quantification of test miRNAs as well as sample purity validation metrics (miR23a and miR451 and erythrocyte transcript SLC4A1/BAND3). Primers used to detect miRNAs should have high specificity and sensitivity. as seen with locked nucleic acid technology (Koshkin et al., 1998). Appropriate instrumentation includes the ABI7900HT or equivalent.
7. The presence of amplification of SLC4A1/BAND3 mRNA transcript is a criterion sample for quality control failure.
8. In the absence of amplification of SLC4A1/BAND3 mRNA, a cycle threshold difference of greater than 7 between miR-23a and miR-451 (Blondal et al., 2013) AND a plasma absorbance value >0.3 should be a criterion for sample quality control failure. It should be noted that absorbance alone is not a reliable hemolysis marker in infant blood samples (Mahnke et al., 2021a), likely due to the conversion of fetal to adult hemoglobin.

Alternative compatible methods to qRT-PCR include isothermal amplification (e.g. Ganguli et al., 2020; Gill and Ghaemi, 2008) and other similar technologies which may improve on the sensitivity and quantification of miRNA expression and allow for detection at point of care.

References which are instructive for determining the concentrations of miRNAs in blood samples, especially umbilical cord and/or placental blood samples and plasma and cellular fractions thereof include the following, reelevant portions of which are incorporated by reference herein.

Balaraman, S., Schafer, J.J., Tseng, A.M., Wertelecki, W., Yevtushok, L., Zymak-Zakutnya, N., Chambers, C.D., and Miranda, R.C. (2016). Plasma miRNA profiles in pregnant women predict infant outcomes following prenatal alcohol exposure. PLOS One 11, e0165081.

Blondal, T., Jensby Nielsen, S., Baker, A., Andreasen, D., Mouritzen, P., Wrang Teilum, M., and Dahlsveen, I.K. (2013). Assessing sample and miRNA profile quality in serum and plasma or other biofluids. Methods 59, S1-6.

Ganguli, A., Mostafa, A., Berger, J., Aydin, M.Y., Sun, F., Ramirez, S.A.S., Valera, E., Cunningham, B.T., King, W.P., and Bashir, R. (2020). Rapid isothermal amplification and portable detection system for SARS-COV-2. Proc Natl Acad Sci USA 117, 22727-22735.

Gill, P., and Ghaemi, A. (2008). Nucleic acid isothermal amplification technologies: a review. Nucleosides Nucleotides Nucleic Acids 27, 224-243.

Koshkin, A.A., Singh, S.K., Nielsen, P., Rajwanshi, V.K., Kumar, R., Meldgaard, M., Olsen, C.E., and Wengel, J. (1998). LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron 54, 3607-3630.

Mahnke, A.H., Sideridis, G.D., Salem, N.A., Tseng, A.M., Carter, R.C., Dodge, N.C., Rathod, A.B., Molteno, C.D., Meintjes, E.M., Jacobson, S.W., et al. (2021). Infant circulating MicroRNAs as biomarkers of effect in fetal alcohol spectrum disorders. Scientific reports 11, 1429.

The term "standard" is used to a describe a pre-determined measurement of concentration of one or more miRNAs established from a neonate or population of neonates with or without NOWS, treated for NOWS including cured of NOWS, for example, which can be used to compare a measurement from a neonate being diagnosed for NOWS and/or monitored for the treatment of NOWS pursuant to the present invention to establish the existence and severity of NOWS in a subject or patient (in order to recommend therapy and/or extended hospital stay) or to establish that a treatment protocol being used in a patient or subject diagnosed with NOWS is causing improvement in the NOWS condition and/or symptomology or can determine when a patient or subject may have therapy modified or terminated or be released from a hospital stay. For example, the standard is a known concentration of miRNA in the leukocytes and/or plasma of neonatal blood, including cord and/or placental blood of a neonate or neonate population without NOWS, a concentration of miRNA in the leukocytes and/or plasma of the blood of a neonate or population of neonates who have been diagnosed with NOWS before treatment, a concentration of miRNA in the leukocytes and/or plasma of neonatal blood after treatment for NOWS, or the concentration of miRNAs in the neonatal blood of a patient or subject before treatment commences. The skilled practitioner can readily provide other standards which can be used in the present invention.

The terms "overexpression" and "up-regulation" are used to describe the concentration of a particular miRNA in neonatal blood compared to a standard that is substantially above the concentration of the standard. Typically, in blood samples which are analyzed, miRNAs which are overexpressed or up-regulated are present in concentrations which generally are from 15% to 150% or more (up to about 200-300% or more) higher than the standard to which the analyzed miRNA is compared.

The terms "underexpression" and "down-regulation" are used to describe the concentration of a particular miRNA in neonatal blood compared to a standard that is substantially below the concentration of the standard. Typically, in blood samples which are analyzed, miRNAs which are underexpressed or down-regulated are present in concentrations which generally are from about 25% to about 90%, often about 30% to about 75%, often about one-third to two-thirds of the standard miRNA measurement to which the analyzed miRNA is compared.

The term "coadministration" is used to describe the administration of two active compounds. Although the term coadministration preferably includes the administration of two active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time. In the present invention, the term coadministration refers to the administration of an opioid such as buprenorphine, methadone, morphine, tincture of opium and mixtures thereof, which treatment may further include barbiturates (e.g., phenobarbital), clonidine, SSRIs and benzodiazepines in the treatment of NOWS which is diagnosed pursuant to the present invention.

The term "neonate opiate withdrawal syndrome" or "NOWS" is used to describe a syndrome which occurs in fetuses/neonates as a consequence of the use of addictive opioid and other substances by the mother prior to and/or during pregnancy. Drug and alcohol use during pregnancy can lead to many health problems in the fetus and baby. These health problems may include:

Tremors (trembling)
Irritability (excessive mood crying)
Sleep problems
High-pitched crying
Tight muscle tone
Hyperactive reflexes
Seizures
Yawning, stuffy nose, and sneezing
Poor feeding and suck
Vomiting
Diarrhea
Dehydration
Sweating The term "long-term hospitalization" or "long-term hospital stay" shall mean a stay in the hospital with attendant hospital level care of at least about 14 days until the patient is ready to be released from the hospital which may be at 14 days, 14-21 days, 21-60 days, 60-120 days up to six months or even longer.

The term "treatment of neonatal opioid withdrawal syndrome" or "intervention treatment of NOWS" (distinguished from long-term hospital stay) is used to describe pharmacological and non-pharmacological treatment methods which are used as standard practice to treat opioid withdrawal syndrome in neonates which have been diagnosed by the present invention. In the pharmacological treatment method, effective amounts of one or more opiates such as buprenorphine, methadone, morphine, tincture of opium and mixtures thereof may further include a barbiturate (e.g. phenobaritol), clonidine, selective serotonin reuptake inhibitors (SSRIs) and benzodiazepines as alternative or additional agents. The duration of pharmacological therapy for NOWS is often 1-7, more often 5-7 days or for that period which results in substantial attenuation of withdrawal and related neurological symptoms in the neonate. Duration of therapy, whether pharmacological or non-pharmacological may last for one or two days, several days to one-two weeks or from one to several weeks to several months. The term "pharmacological treatment of neonatal opioid withdrawal syndrome" is used to describe pharmacological treatment methods, described above, which are used as standard practice to treat opioid withdrawal syndrome in neonates.

Non-pharmacological treatments of NOWS focus on minimizing dysregulation and maximizing infant functioning. Treatments are heterogeneous interventions within three main categories of care. These are: environmental stimulation; feeding strategies; and functioning of the mother-infant dyad. Interventions may occur alone or in combination with other non-pharmacological and pharmacological treatments. Often, during extended hospital stay in which pharmacological intervention is not recommended, non-pharmacological intervention is often used to treat the neonate during the extended hospital stay.

Treatments addressing environmental stimulation reduce negative stimuli and promote positive experiences. Gentle handling and maintaining a low-light, quiet environment reduce negative stimulation. Infant containment or swaddling, bedding choice including vibrating beds, and infant positioning may also soothe infants. Positive experiences may include non-nutritive sucking and bathing. Aromatherapy, music therapy, massage, and acupuncture/acupressure are therapies that may also calm infants through stimulation.

Treatments addressing feeding strategies are directed to disorganized feeding and weight loss which are common in infants withdrawing from opioids. In general, breast milk and breastfeeding reduce withdrawal symptoms. Small, frequent feeds and infant-led feeding are often helpful to improve transfer of feeds. Higher calorie feeds or tube feeds may reduce weight loss in these infants. Breast milk or low-lactose formula may reduce gas and feeding discomfort.

The functioning of the mother-infant dyad is also an important feature of non-pharmacological therapy of NOWS. Treatments also address the health and support of the mother-infant dyad as a unit. Parental presence alone is an important aspect of non-pharmacological care. Rooming in and skin-to-skin care promote mother-infant bonding and infant regulation. Direct parental support promotes parental well-being. Well caregivers are better able to recognize and respond to infant cues. Parental supports enhance comfort and plan for respite. Examples include 'cuddler' programs and designated parental hospital spaces. Staff contribute to parental well-being by using trauma-informed care principles. A thorough needs assessment may also improve parental well-being. Needs may include addiction, social, mental health, legal, and custody supports.

In the pharmacological treatment of NOWS pursuant to the present invention, the compositions described herein for the treatment of NOWS may be administered by any route of administration, including parenteral, topical or oral administration among others, in preferred aspects of the invention, the opioid and optional additional agent is preferably administered parenterally by IV administration to the neonate. By delivering drugs IV, the IV administration may be adapted readily to allow samples of blood to be taken from the neonate for monitoring of therapy.

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing Company.

Optimal pharmaceutical formulations can be determined by one skilled in the art depending upon, for example, the intended route of administration, delivery format and desired dosage as well as the size and/or body weight of the neonate to be treated. See, for example, REMINGTON'S PHARMACEUTICAL SCIENCES, Id. Such formulations may influence the physical state, stability, rate of in vivo release and rate of in vivo clearance of the antibodies of the invention.

Primary vehicles or carriers in a pharmaceutical formulation can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical formulations of the invention can be delivered parenterally, preferably by intravenous administration. When parenteral administration is contemplated, the therapeutic formulations for use in this invention may be in the form of a pyrogen-free, parenterally acceptable aqueous solution. Preparation involves the formulation, which may provide controlled or sustained release of the product which may then be delivered via a depot injection. Formulation with hyaluronic acid has the effect of promoting sustained duration in the circulation.

Formulations of the invention can be delivered through the digestive tract, such as orally. The preparation of such pharmaceutically acceptable compositions is within the skill of the art. Formulations disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption. Diluents, flavorings, low melting point waxes, vegetable oils, lubricants, suspending agents, tablet disintegrating agents, and binders may also be employed.

A formulation may involve an effective quantity of a microparticle containing formulation as disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Administration routes for formulations of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical formulations may be administered by bolus injection or continuously by infusion, or by implantation device. The pharmaceutical formulations also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The pharmaceutical compositions of the invention are safe and effective for use in the treatment or prevention (reducing the likelihood) of NOWS after diagnosis according to the present invention. Although the dosage of the composition of the invention may vary depending on the type of active substance administered, the route of administration, as well as the nature (size, weight, etc.) of the subject to be treated, the composition is administered in an amount effective for allowing the pharmacologically active substance to be effective. For example, the composition is preferably administered such that the active ingredient can be given to a human adult in a dose of about 0.001 to about 10-15 mg or more, about 0.01 mg to about 10 mg, about 0.05 mg to about 8 mg, about 0.1 mg to about 3.5 mg, about 0.5 mg to about 3.0 mg, about 1 to about 2.5 mg.

The amount of an opioid agent that may be combined with the carrier materials to produce a single dosage form will vary depending upon the host treated and the particular mode of administration. Preferably, the compositions should be formulated so that a therapeutically effective dosage of between about 0.01 and 10 mg/kg, about 0.05 to about 7.5 mg/kg of the patient/day, preferably between 0.1 mg and 5.0 mg/kg or about 0.5 mg to about 7.5 mg/kg of the patient/day of the opioid agent and optional agent can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

The form of the pharmaceutical composition of the invention such as a powder, solution, suspension etc. may be suitably selected according to the type of substance to be administered.

As an administration route, direct intravenous administration is often preferable because it allows collection of blood from the subject or patient for further analysis and/or monitoring of therapy. Since the pharmaceutical composition of the invention allows direct local administration into the vascular system, the active substance contained therein produces immediate effects. Furthermore, the composition is formulated as an immediate release product so that NOWS therapy can begin soon after administration.

The invention, having been described above, is further illustrated in the following non-limiting examples.

EXAMPLES

Example 1

1.1 $_{cir}$miRNAs Discriminate Between NOWS and Non-NOWS Infants

Figure 4:
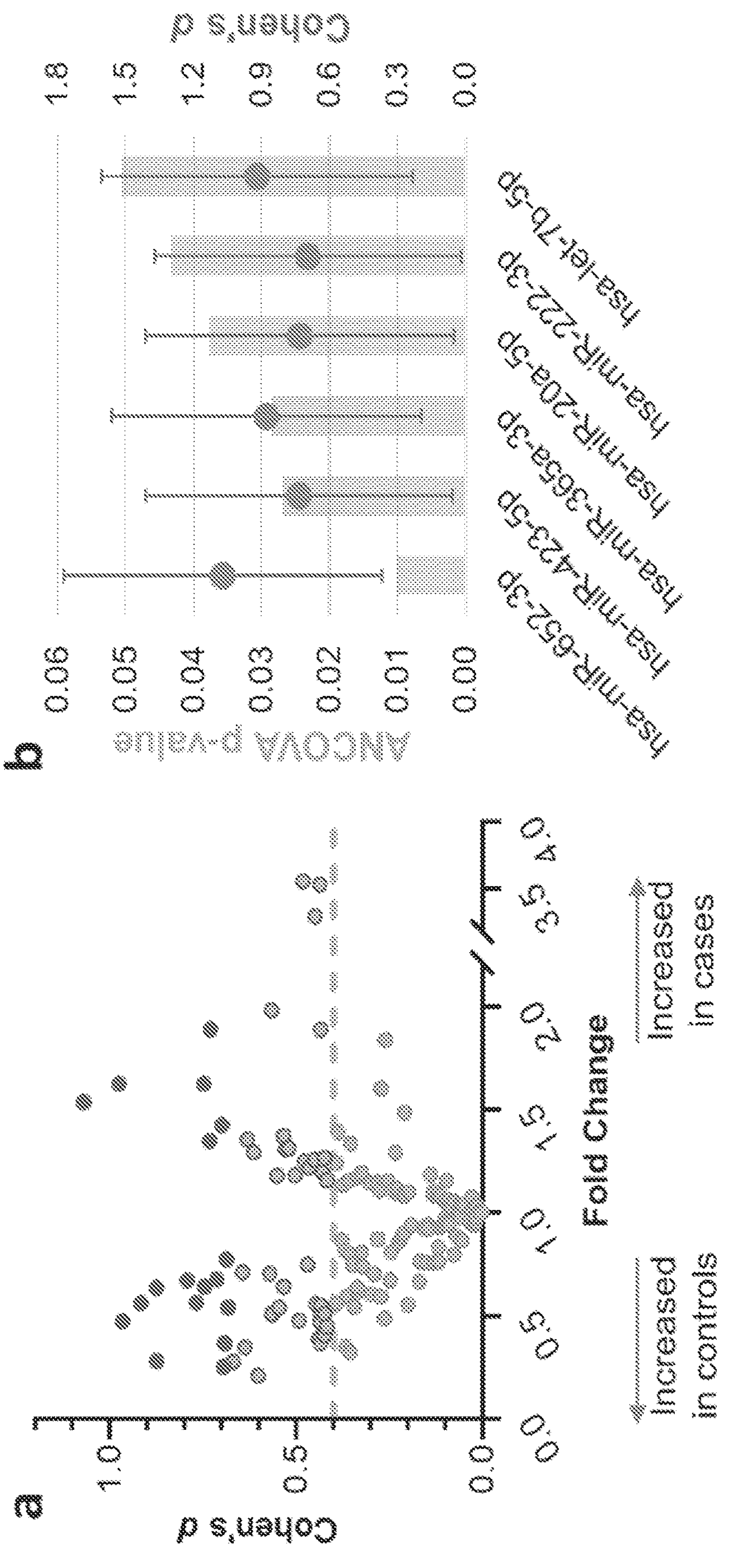
FIG. 4 shows neonatal $_{cir}$miRNAs which differentiate opioid-exposed neonates who develop withdrawal symptoms from exposed neonates who are not diagnosed with withdrawal symptoms. (a) A number of $_{cir}$miRNAs are altered to a clinically relevant effect size (dashed line) in neonates who develop NOWS (cases) compared to neonates who do not undergo withdrawal (controls). A subset of these are significantly altered with a non-zero 95% confidence interval (circles above the dashed line). (b) 6 $_{cir}$miRNAs were significantly altered when gestational age was included as a covariate (light gray vertical rectangles) and significantly altered with moderate-to-large effect sizes (gray circles). Error bars denote 95% confidence intervals.
Figure 5:
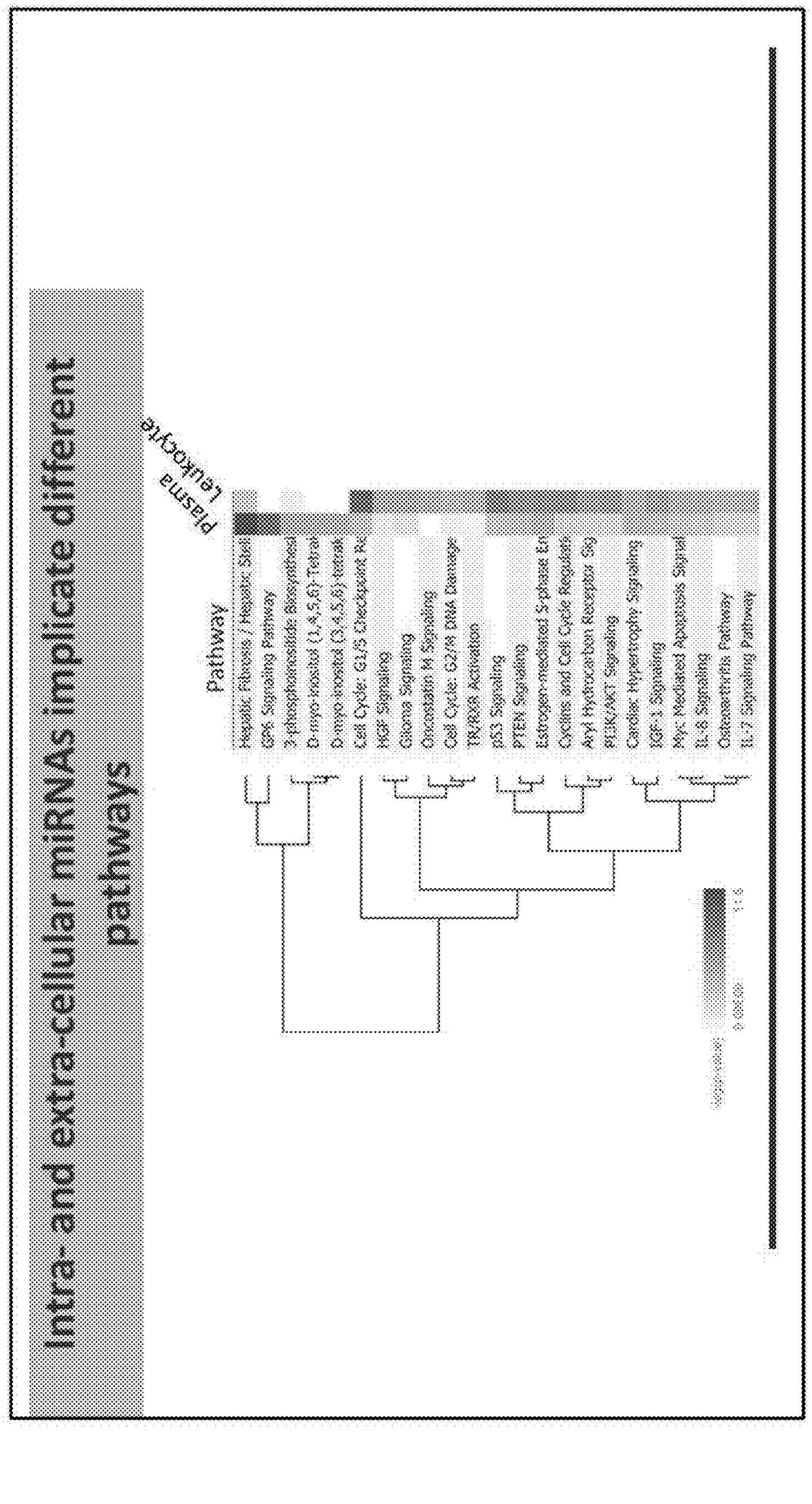
FIG. 5 shows ingenuity pathway analysis allowed for the assessment of possible miRNA target pathways for the preliminarily significant miRNAs. Target mRNAs were experimentally validated or highly predicted targets for the subset of miRNAs which were significantly altered between groups in this preliminary analysis (non-zero 95% confidence interval). Pathways were determined by the enrichment of target mRNAs within the pathways. Hierarchical clustering shows that hepatic, inflammation (GP6), and metabolic pathways are implicated by the plasma miRNAs while the leukocyte miRNAs target cell cycle growth pathways and intracellular signaling cascades.
Figure 6:
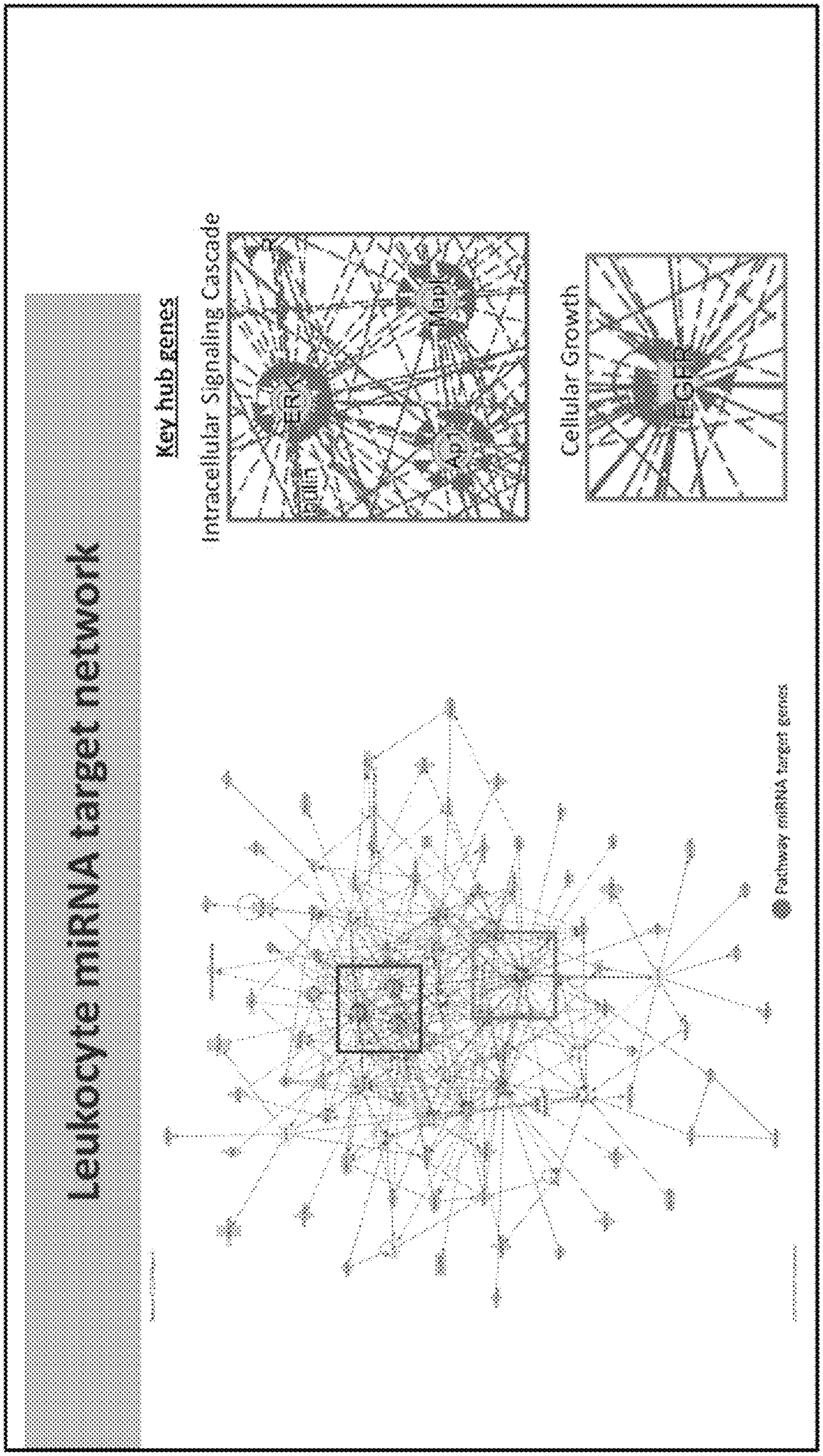
FIG. 6 shows an example leukocyte target mRNA network with the direct miRNA target mRNAs shown in grey. Node mRNAs included ERK/MapK pathway members and cytokine and growth factor responsive transcription factor AP-1.
Figure 7:
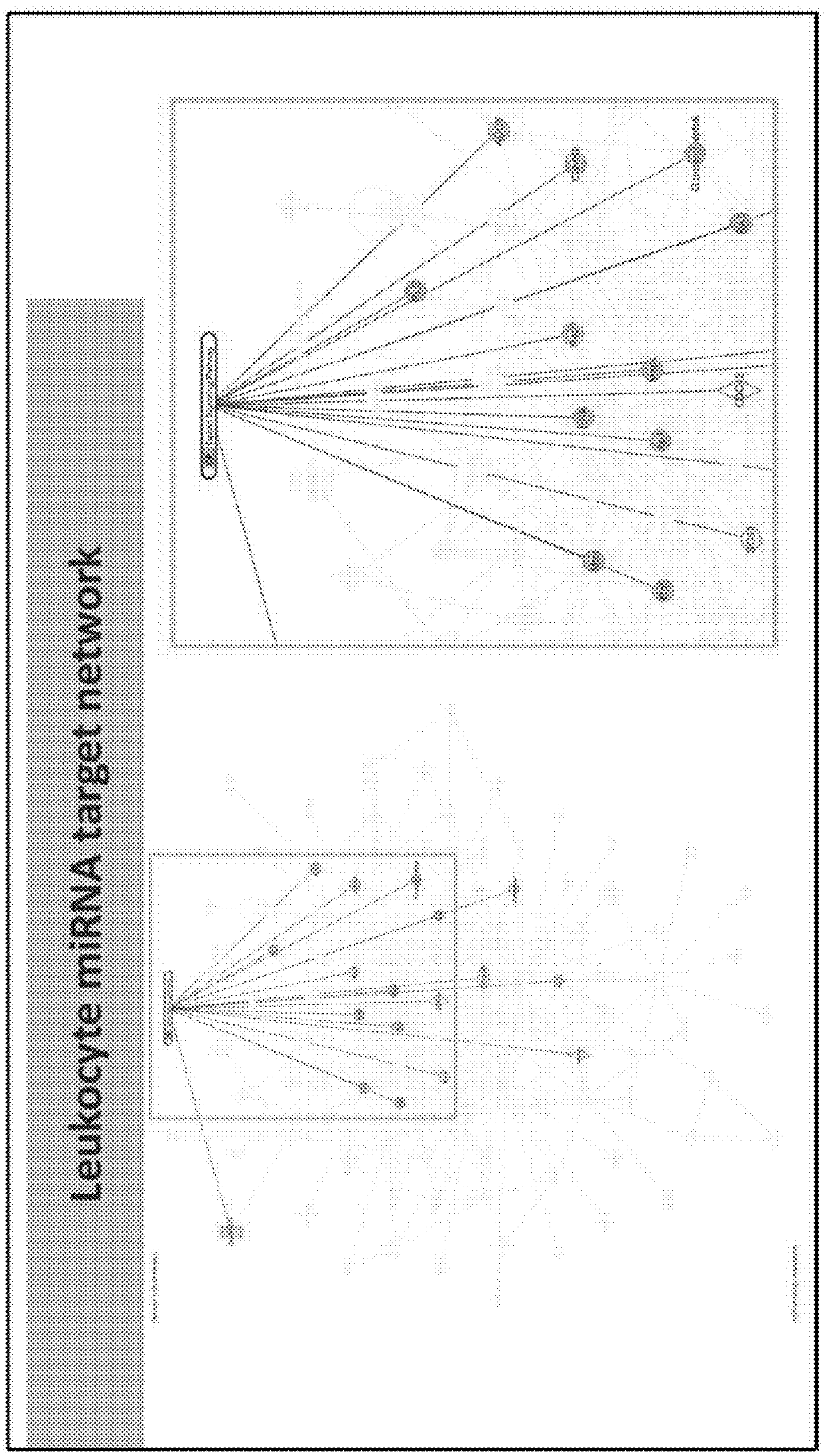
FIG. 7 shows that members of this leukocyte network show enrichment for canonical signaling pathways which would be expected to be different between infants-treated-for-NOWS and infants-not-treated-for-NOWS, including potential difference in expression of proteins within the opioid signaling pathway.
Figure 8:
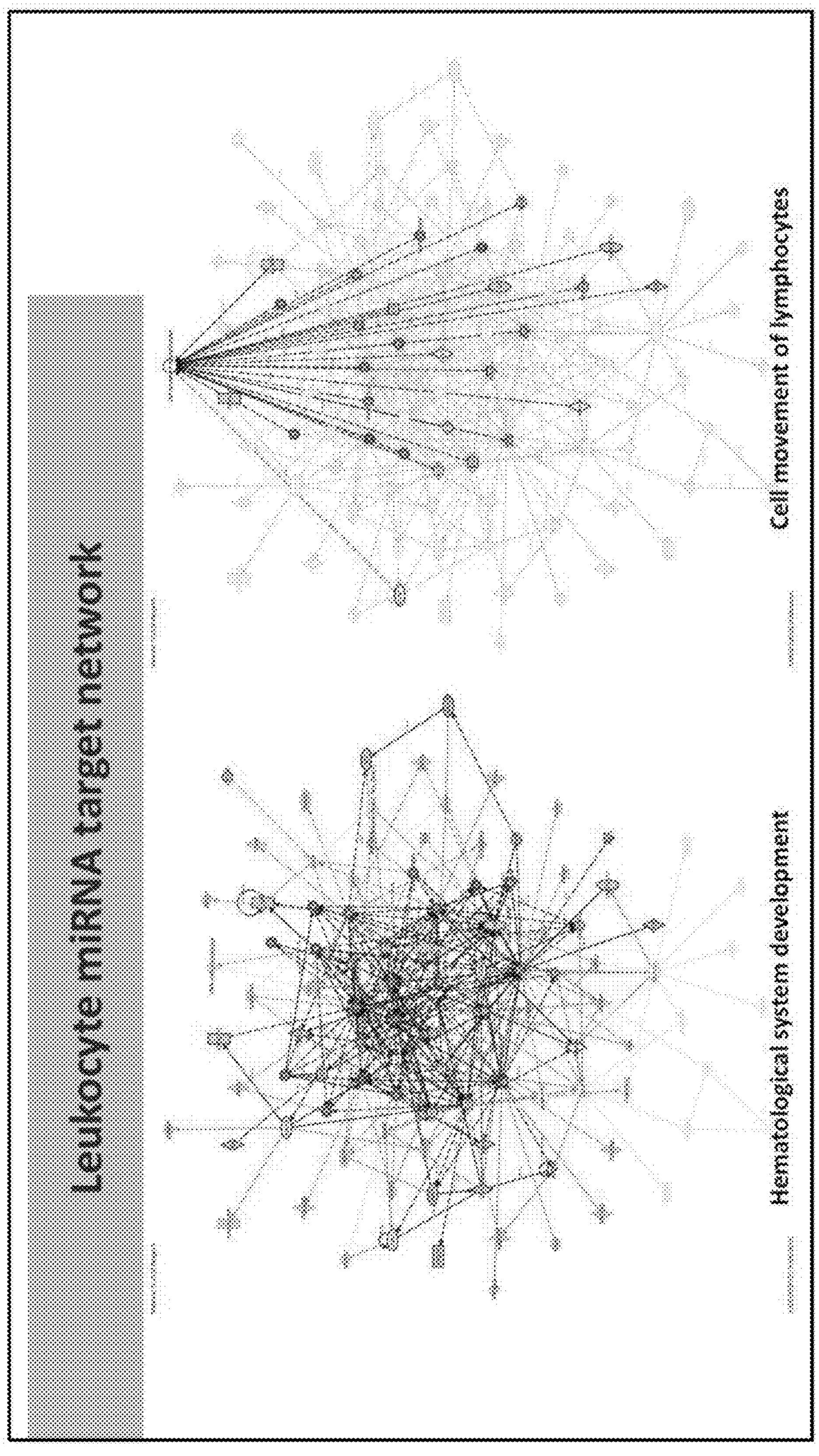
FIG. 8 shows that mRNAs within this leukocyte network have been associated with hematological system development pathways, including the cellular movement and development of lymphocytes.
Figure 9:
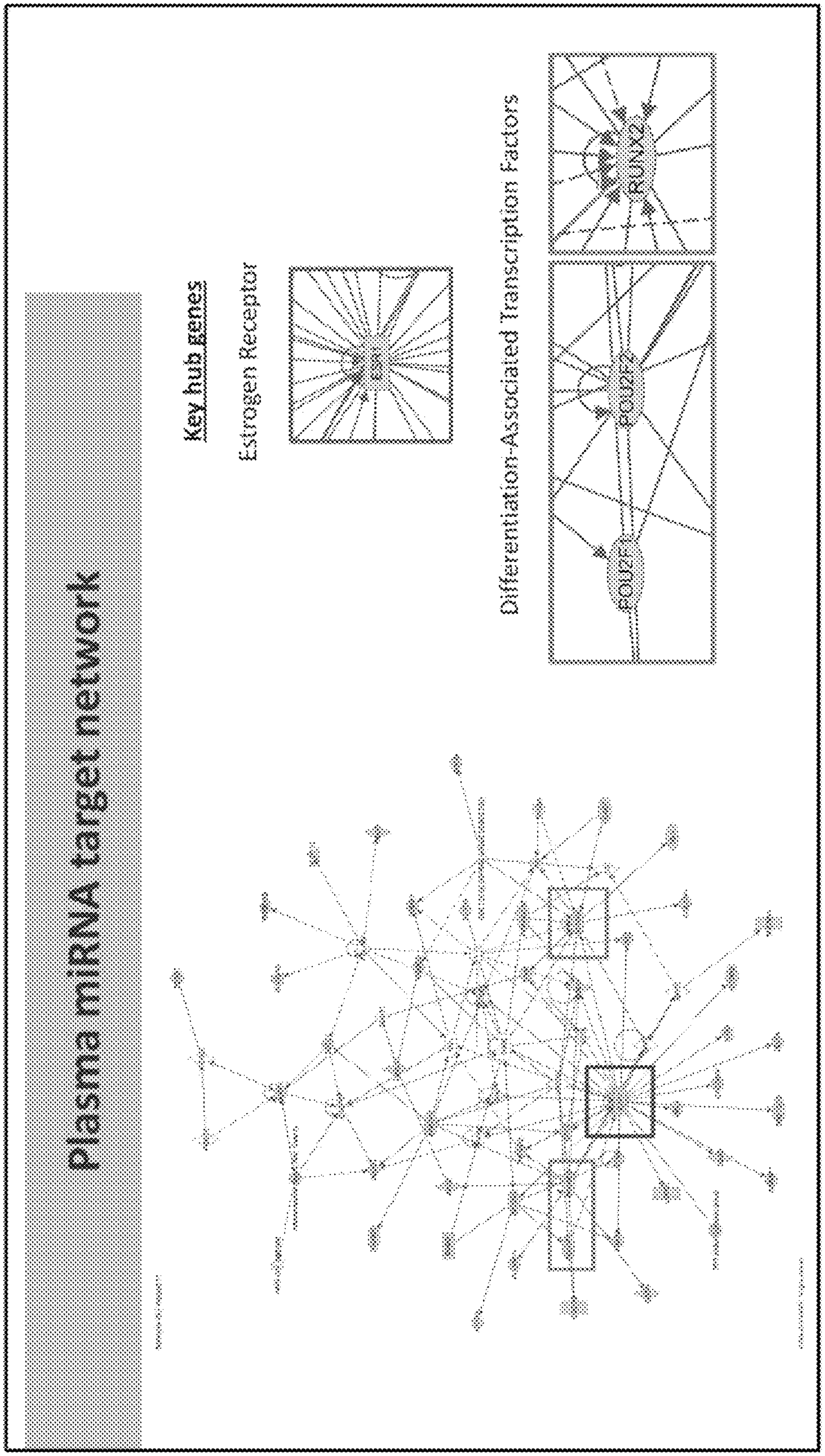
FIG. 9 shows an example plasma miRNA target network includes the ESR1/ERα receptor as well as differentiation associated transcription factors POU2F1/OCT1, POU2F2/OCT2 and RUNX2.
Figure 10:
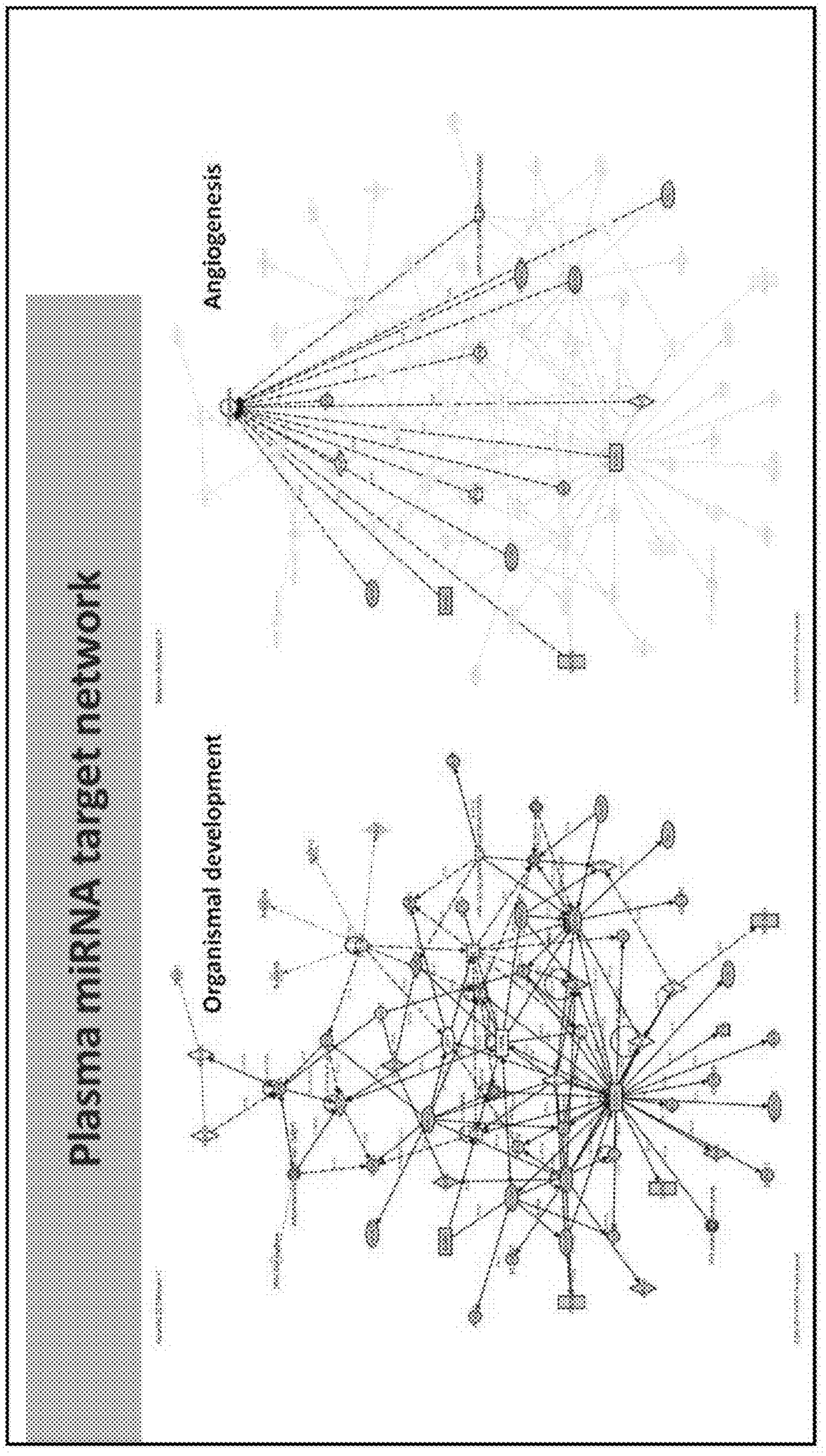
FIG. 10 shows the presented plasma miRNA target network is largely constructed of miRNAs implicated in organismal development pathways including angiogenesis.
Figure 11:
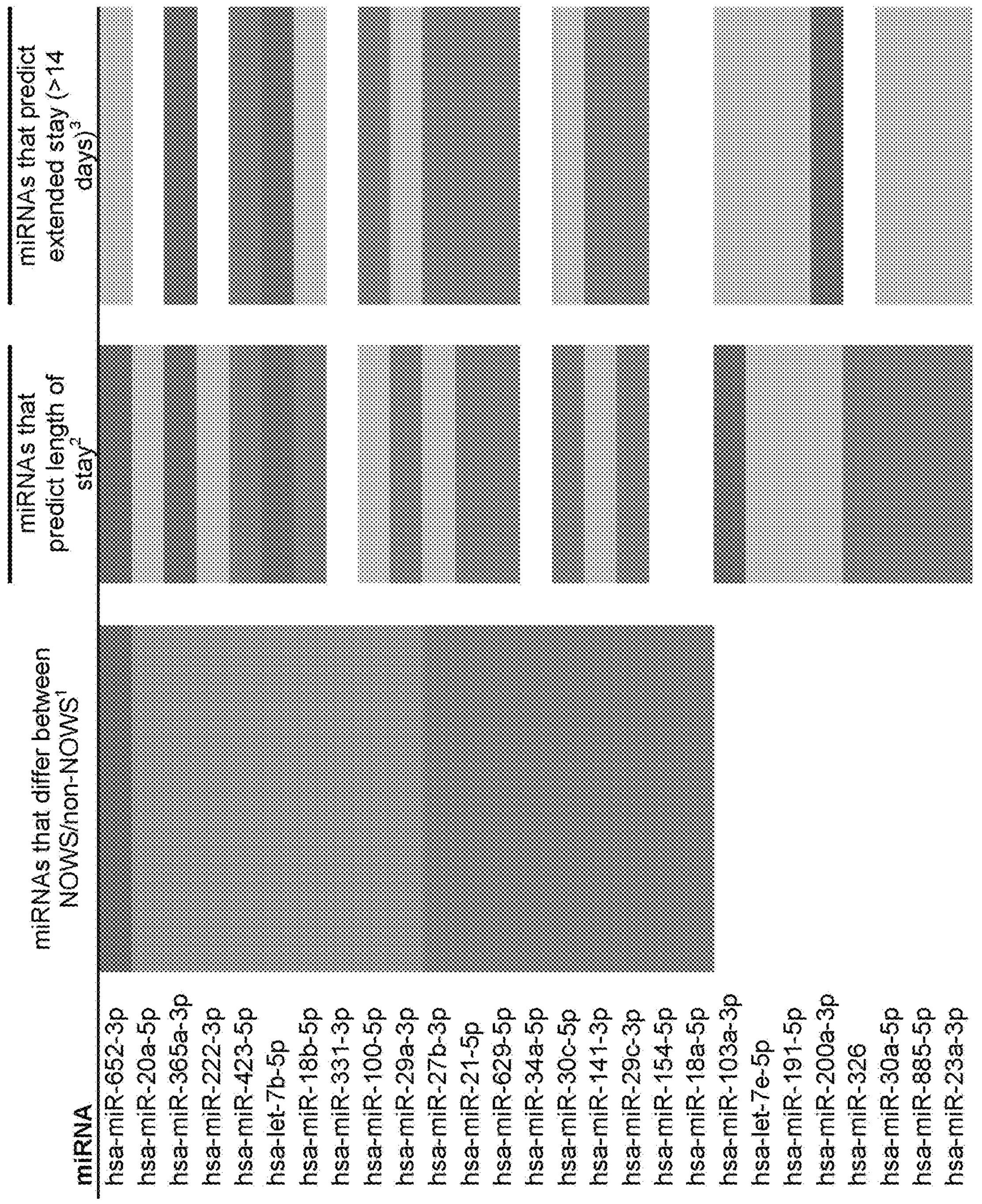
FIG. 11 shows a number of potential miRNA biomarkers of Neonatal Opioid Withdrawal Syndrome (NOWS). miRNA expression (dependent variable) in cases (prenatal opioid exposure, treated for NOWS) compared to controls (prenatal opioid exposed, not treated for NOWS; ANOVA). Independent variable, whether the neonate received pharmacological treatment for NOWS, was adjusted for gestational age at birth. [2]miRNA expression (adjusted for gestational age at birth, independent variable) compared to length of hospital stay for neonates (dependent variable, ANOVA). [3]miRNA expression (adjusted for gestational age at birth, independent variable) compared to occurrence of extended length of stay (>14 days, logistic regression). P-values and significance are coded in varying shades of gray with the darkest gray area approaching a significant effect size.
Figure 11:
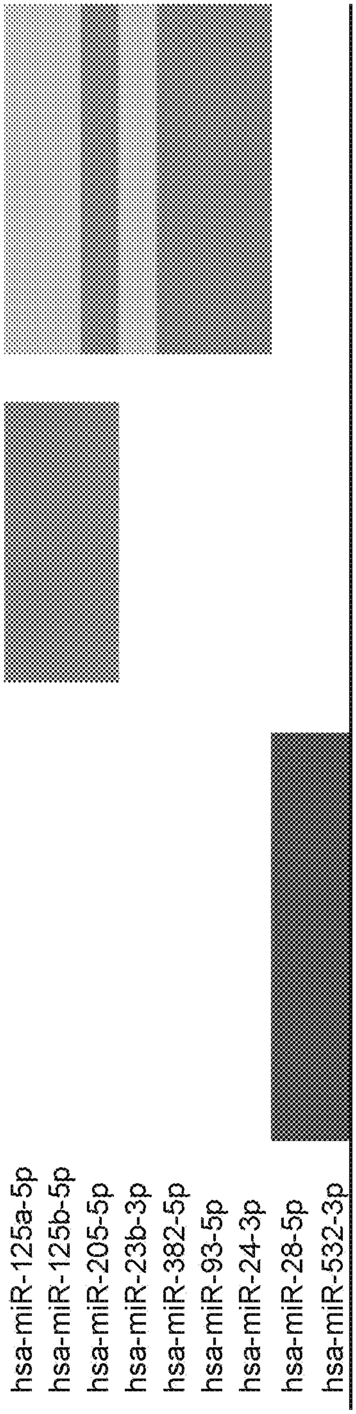
Figure 12:
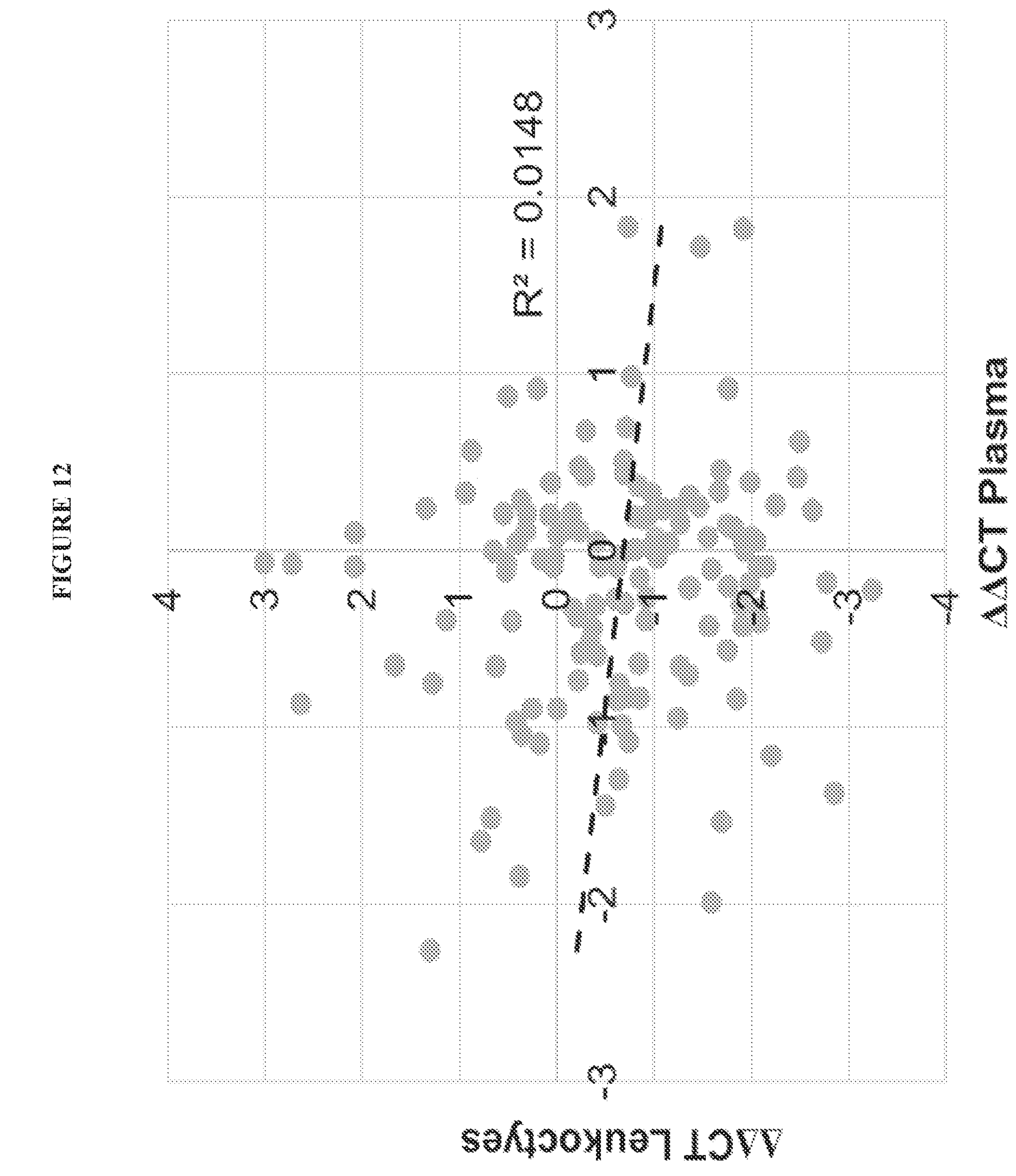
FIG. 12 shows neonatal plasma miRNAs are not primarily derived from leukocytes. The expression of plasma and leukocyte miRNAs in cord blood are not directly related, shown by a linear regression on miRNA expression which is not significantly different from zero (p=0.164).

The inventors have assessed $_{cir}$miRNAs from cord blood of neonates prenatally exposed to medically assisted therapy (MAT) for opioid use disorders. These samples were collected as part of the Ethanol, Neurodevelopment, Infant and Child Health (ENRICH) cohort at the University of New Mexico. Plasma $_{cir}$miRNAs were assessed using quantitative real-time PCR (qPCR) (Qiagen miRNAeasy Mini RNA isolation kit, miRCURY LNA miRNA pipeline, and Serum/Plasma Focus PCR panels). The $_{cir}$miRNA profile was altered in opioid-exposed neonates who were treated for neonatal opioid withdrawal syndrome (NOWS; cases) compared to those neonates who were not diagnosed with withdrawal symptoms (controls) (See FIG. 4*a*). This $_{cir}$miRNA signature was robust, with 38% of the expressed miRNAs altered at a clinically relevant effect size of Cohen's d>0.4 (Hattie, 2009a) and 12% were significantly altered (95% confidence interval was non-zero spanning). This plasma miRNA profile was unique and not directly attributable to leukocyte intracellular miRNA expression, as there was no relationship between plasma and leukocyte miRNA expression (See FIG. 12). While NOWS infants had a significantly lower gestational age at delivery (cases: 37.3±1.0 wk (N=17); controls: 38.8±1.4 wk (N=37); p=0.0002), a subset of $_{cir}$miRNAs were significantly altered by effect size with a non-zero confidence interval and by ANCOVA, with gestational age a covariate (FIG. 4B). These $_{cir}$miRNAs are further assessed as biomarkers of infant outcome.

Example 2

46 umbilical cord-derived plasma samples were analyzed for 179 miRNAs. The sample included 13 from infants with severe NOWS requiring pharmacological treatment and 33 from infants born to women with opioid use disorder (OUD) who had mild NOWS not requiring pharmacological treatment. Table 1, FIG. 13 presents the area under the curve (AUC), representing sensitivity/specificity among all cutoff points, for the batteries of 1-6 miRNAs, as well as parameter estimate (β), standard error (se), and corresponding p-value from logistic regression. A combination of 3 miRNAs (hsa-miR-652-3p, hsa-miR-365a-3p, and hsa-let-7b-5p) achieved AUC=0.869 (95% CI: 0.76; 0.98). Addition of hsa-miR-423-5p, hsa-miR-20a-5p, and hsa-miR-222-3p improved AUC to 0.881 (95% CI: 0.77; 0.99). Addition of gestational age further improved AUC to 0.911.

Figure 14:
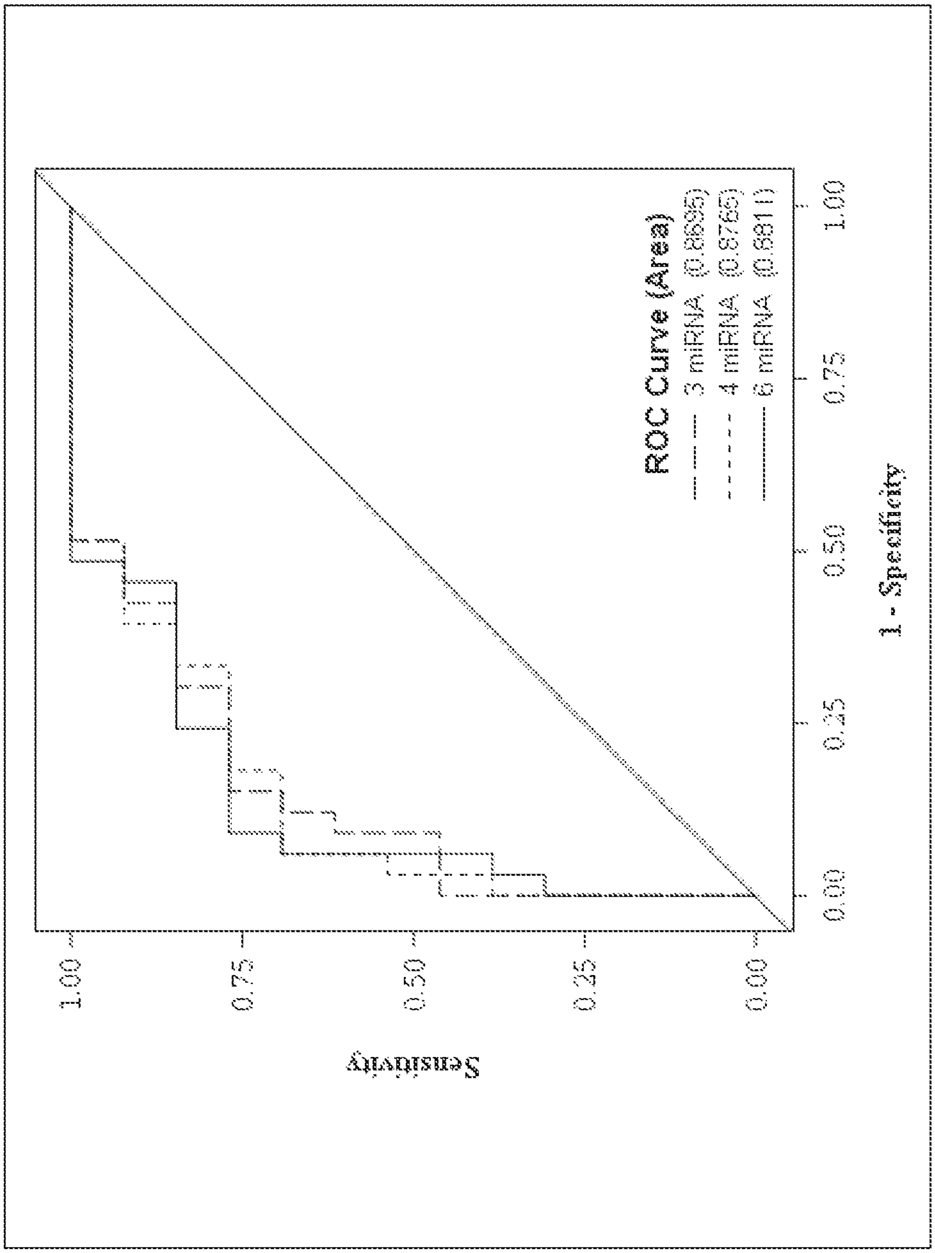
FIG. 14 shows Area under the Curve for Accuracy of Top miRNAs to differentiate Cases and Controls (N=46). This figure presents AUC for the combination of 3, 4, and 6 miRNAs graphically. The AUC for the combination of 6 miRNAs is 88.1%. This demonstrates excellent ability to differentiate infants Treated-for-NOWS from Not-Treated-for NOWS. Four miRNAs which consistently emerged as the most predictive in the unadjusted and multivariable (adjusted for gestational age) models included: miR--652-3p, miR-423-5p, miR-365a-3p, and miR-7b-5p.

FIG. 14 presents AUC for the combination of 3, 4, and 6 miRNAs graphically. The AUC for the combination of 6 miRNAs is 88.1%. This demonstrates excellent ability to differentiate infants Treated-for-NOWS from Not-Treated-for NOWS. Four miRNAs which consistently emerged as the most predictive in the unadjusted and multivariable (adjusted for gestational age) models included: miR-652-3p, miR-423-5p miR-365a-3p, and miR-7b-5p.

Figure 15:
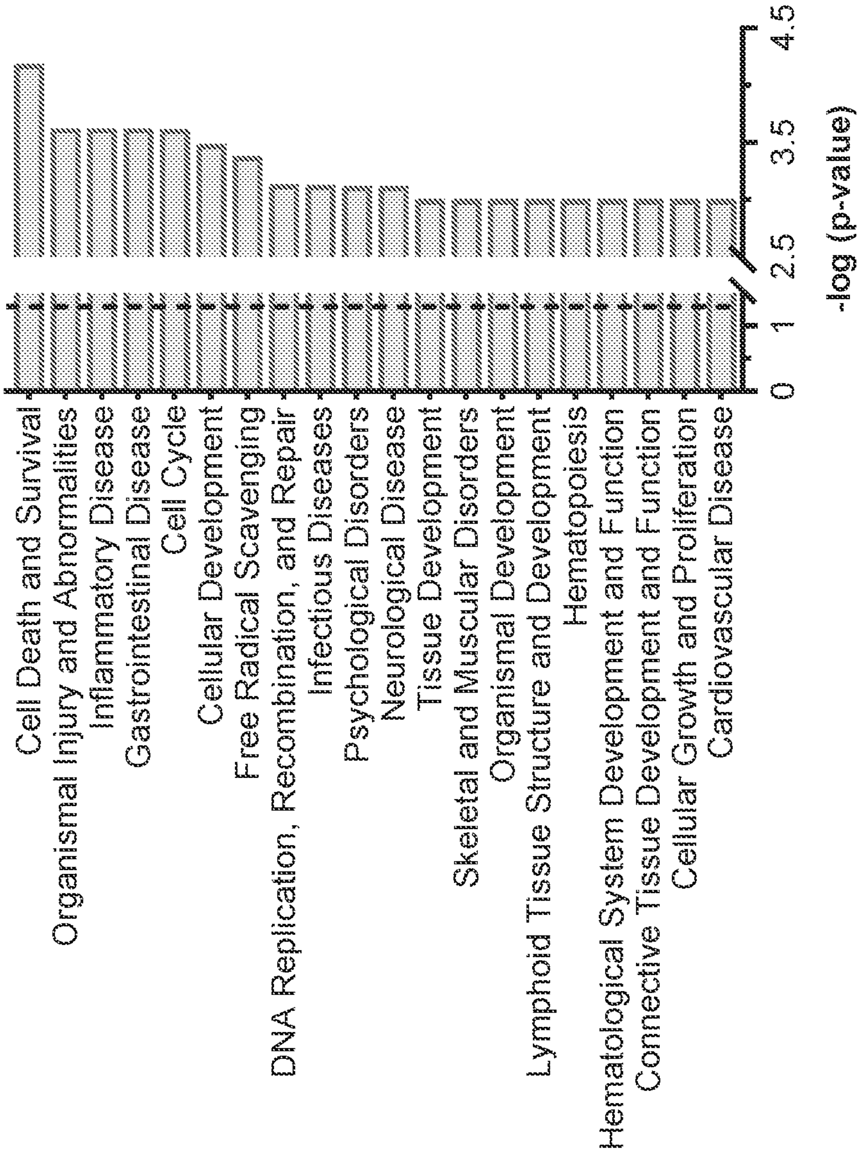
FIG. 15 shows an ingenuity pathway analysis of mRNA targets of top miRNAs. This figure presents the pathway targeting for the top 4 miRNA candidates. These miRNAs target developmental pathways and are implicated in injury and disease pathways which would be likely to be implicated in the etiology of NOWS.

FIG. 15 presents the pathway targeting for the top 4 miRNA candidates. These miRNAs target developmental pathways and are implicated in injury and disease pathways which would be likely to be implicated in the etiology of NOWS.

Example 3

In the inventor's preliminary analysis, they have identified miRNAs which were altered in the NOWS neonates compared to the non-NOWS neonates, therefore are indicative of NOWS development prior to symptom onset (Table 2, FIG. 16). They have also identified miRNAs that are associated with length of hospital stay (in days), including extended length of hospital stay (>14 days) which are indicative of NOWS severity.

Figure 17:
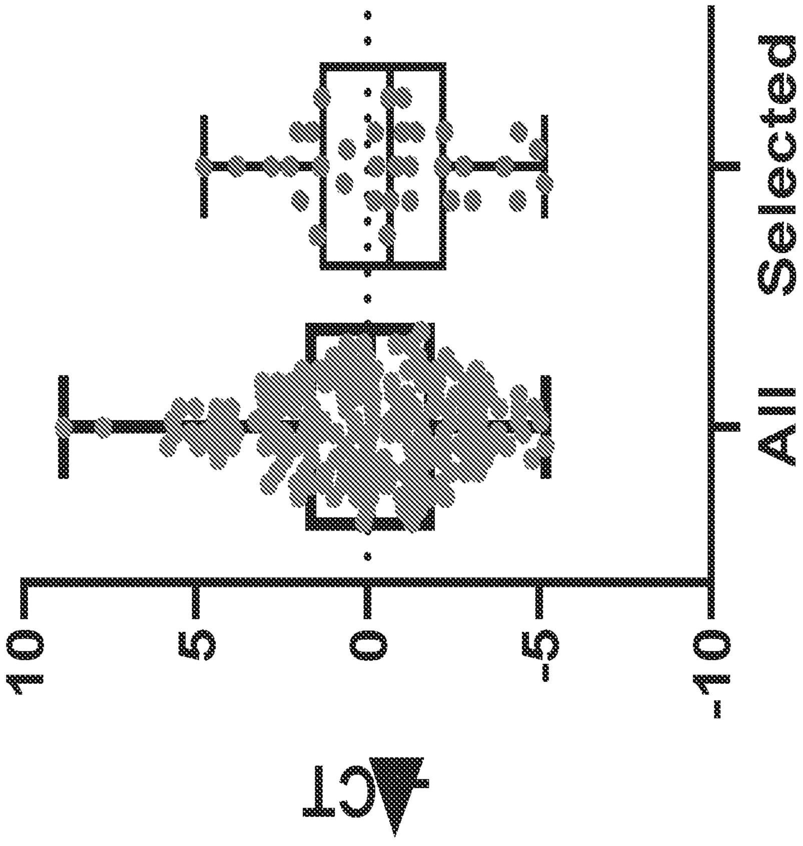
FIG. 17 shows box plots of relative expression of all miRNAs assessed (All, black) and identified clinically relevant miRNAs (see also FIG. 16, Table 2).

These miRNAs were isolated from umbilical cord blood plasma and assessed using quantitative real-time PCR (qPCR). Expression of these miRNAs was assessed by comparing the cycle of detection of the miRNA of interest (cycle threshold, $CT_{miRNA}$) with the global mean of CTs for all miRNAs assessed for a sample ($CT_{global}$), which is thought to be invariant between samples and controls for differences in miRNA expression between samples, to derive the change in CT (ΔCT, $CT_{miRNA}$-$CT_{global}$). We selected the clinically relevant candidate miRNAs (FIG. 16, Table 2, FIG. 17, blue) from a panel of miRNAs (FIG. 17, black). The clinically relevant 'selected' miRNAs were all expressed within the range of detection for the entire panel, 55% of which were within two cycles of $CT_{global}$, (~32 cycles on average). Clinically relevant miRNA expression will be determined in comparison to a group of miRNAs which are invariant in expression across samples, thereby replacing the $CT_{global}$ value in the ΔCT equation. Quantification of these miRNAs can be performed on alternate, but currently less clinically available, instrumentation platforms, to obtain absolute miRNA concentrations.

Figure 18:
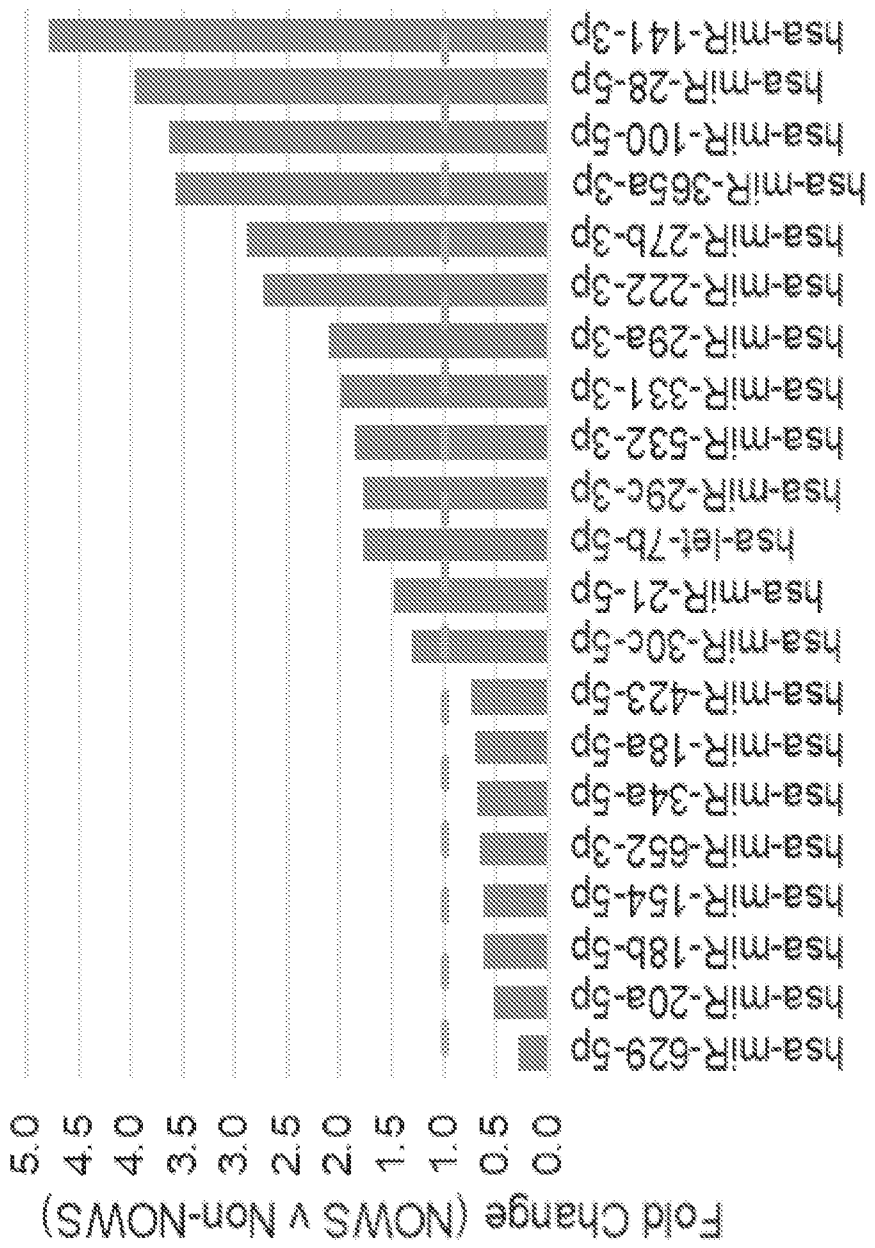
FIG. 18 shows the differential expression of miRNAs indicative of NOWS development.

The inventors compared relative expression of miRNAs infants with severe NOWS and those with mild/no NOWS and identified a subset of miRNAs which were significantly different between the groups in the preliminary analysis, as well as miRNAs which trended towards significance. Of these miRNAs, 38% were decreased and 62% were increased in neonates with severe NOWS compared to mild/no NOWS neonates (FIG. 18). These miRNAs were differentially expressed by at least 1.3-fold and some greater than a 3-fold difference.

From the refined miRNAs, the inventors design a panel that will identify neonates with severe NOWS to allow for increased monitoring for withdrawal symptoms and rapid administration of opioids to mitigate withdrawal, as well as potential combination of pharmacologic and non-pharmacologic (i.e., the Eat, Sleep, Console) modalities. miRNAs which are indicative of length of stay will provide an indicator of NOWS severity, allow for the prioritization of hospital resources to differentiate low-risk infants who can be discharged earlier and high-risk infants requiring substantial hospital resources, and have potential as indicators of treatment efficacy.

Example 4

It is known that prenatal opioid exposure (POE) is commonly associated with neonatal opioid withdrawal syndrome (NOWS), but there is currently no maternal or infant factors that can accurately predict which neonates will develop symptoms of physiologic and/or behavioral dysregulation and their severity. Risk stratification may allow for adjustment of the required period of hospital observation (for low-risk infants) and earlier initiation of treatment (for high-risk infants). The aim of this example was to determine if extracellular microRNAs present in umbilical cord plasma of infants with POE at birth could predict subsequent severity of NOWS.

Participants (N=58) in this study consisted of pregnant women receiving medications, buprenorphine and methadone, for opioid use disorder and their infants. Two primary measures of NOWS severity were utilized: the need for pharmacological treatment and length of hospital stay. Cord blood miRNAs were assessed using semi-quantitative, low density qRT-PCR arrays. The expression of five miRNAs (miR-421, miR-146-5p, miR-629-5p, miR-223-3p and miR-30c-5p) predicted the need for pharmacological treatment (sensitivity: 94.1%, specificity: 97.6%) and four miRNAs (let-7b-5p, miR-30c-5p, miR-629-5p, and miR-590-5p) predicted a prolonged hospitalization of ≥14 days (sensitivity: 87.5%, specificity: 97.6%). These findings indicate that infant cord blood extracellular miRNAs can proactively identify opioid-exposed neonates at high-risk for developing severe NOWS.

The primary objective of the current example was to determine if extracellular plasma miRNAs, derived from the umbilical cord at birth, could predict the severity of NOWS, indicated the need for pharmacologic treatment with opioids and length of hospital stay. We hypothesized, given our previous research showing that circulating miRNAs could predict infant outcomes following ethanol exposure, that neonatal circulating miRNAs would have predictive value for both metrics of NOWS severity.

Methods

Study Design and Population:

This example used a study population derived from the 'Ethanol, Neurodevelopment, Infant and Child Health' (ENRICH) prospective cohort study. The primary objective of the ENRICH study was to identify early indices of functional brain damage associated with prenatal alcohol exposures (Bakhireva et al., 2019; Bakhireva et al., 2015; Beauchamp et al., 2020). In addition to unexposed controls, patients receiving MOUD were recruited as another comparison group due to similarities in pre- and post-natal environment between substance-using populations. The cohort was formed by recruiting pregnant women during one of the first prenatal care visits. Children born to cohort participants were followed for up to 20 months of age. ENRICH study included 4 prospective visits, and data obtained from Visit 1 (prenatal) and Visit 2 (delivery/birth) were used in this analysis. The general eligibility criteria for the ENRICH study were: 1) ≥18 years old; 2) singleton pregnancy confirmed by ultrasound; 3) no fetal diagnosis of a major structural anomaly; 4) no more than minimal use of cocaine, crack-cocaine, MDMA (ecstasy), or methamphetamine use (per repeated prospective self-reports and repeated urine drug screen (UDS) tests). Minimal use includes no more than 1 urine drug test or incidence of self-report during the first trimester and abstention from use of these substances during the second and third trimesters (Beauchamp et al., 2020).

For this analysis, the following additional eligibility criteria were employed: 1) participants recruited into MOUD group; 2) no self-reported alcohol use in the third trimester and no more than one positive ethanol biomarker in a comprehensive panel (described below); 3) gestational age at delivery ≥34 weeks; 4) available umbilical cord blood sample.

Characterization of Maternal MOUD and Other Prenatal Factors:

The MOUD group was recruited from the University of New Mexico Milagro Clinic, an interdisciplinary clinic specializing in treating pregnant women with substance use disorders. The type of MOUD (methadone vs. buprenorphine) and dose before delivery were abstracted from electronic medical records (EMR). Co-exposure with illicit drugs was assessed throughout pregnancy (timing and frequency) by prospective repeated interviews, based on the 2011 National Survey on Drug use and Health (National Survey on Drug Use and Health). Self-reported information was verified by study-specific Urine Testing Drug Panel-7 (UDS-7; US Drug Testing Lab, Des Plaines, IL) conducted at Visit 1 and Visit 2. The UDS-7 panel measured amphetamines, barbiturates, benzodiazepines, cocaine, opiates, PCP, and cannabinoids/THC metabolites. Alcohol use was captured by three Timeline Follow-back (TLFB) interviews which captured use a month around conception, 30 days before enrollment, and 30 days before delivery. Quantity and frequency of reported alcohol at each day were converted into the ounces of absolute alcohol per day (AA/day, (Jacobson et al., 2002)) and averaged across TLFB calendars. In addition, a panel of ethanol biomarkers (gamma-glutamyl transpeptidase [GGT], carbohydrate deficient transferrin [% dCDT], phosphatidylethanol [PEth], urine ethyl glucuronide and ethyl sulfate [uEtG/uEtS]) was evaluated in maternal samples at baseline and delivery visits as well as PEth measured in dry blood spots of a newborn (Bakhireva et al., 2012; Bakhireva et al., 2014; Bakhireva and Savage, 2011).

NOWS Severity Measures, Infant and Postnatal Environment Measures:

The primary outcome of interest was to determine miRNAs that predict: 1) which opioid-exposed neonates will be Pharmacologically-Treated, compared to neonates Not-Pharmacologically-Treated, and 2) which opioid-exposed neonates will have an extended length of hospital stay, defined as a hospital stay of ≥14 days. These measures are widely used in clinical studies for assessment of NOWS severity (Al-Hashimi et al., 2013; Bagley et al., 2014; Gopman, 2014). According to the UNMH guidelines, pharmacological treatment of NOWS is initiated if an infant scored ≥8 on the Finnegan Neonatal Abstinence Scoring Tool (Finnegan et al., 1975) on three consecutive assessments, if the mean of three scores is ≥8, or if two consecutive scores are ≥12 (Leeman et al., 2011). Newborns are scored at admission (~2 hours of age). All infants with confirmed or suspected prenatal opioid exposure remain inpatient at University of New Mexico Hospital for a minimum of 96 hours.

Circulating miRNA Analyses:

Umbilical Cord Blood Collection and RNA Isolation

Immediately following delivery, blood samples were collected from umbilical cord in EDTA-coated tubes. Plasma was separated by centrifugation at 2000 g for 10 minutes, collected in 200 μL aliquots, placed at −80° C., shipped to Texas A&M University on dry ice, and stored at −80° C. until processing. Total RNA was isolated from 125-200 μL of plasma using the miRNeasy mini kit (Qiagen Sciences, Germantown, MD) with the addition of 1.2 μg carrier MS2 phage RNA (Roche Diagnostics, Mannheim, Germany), according to manufacturer's protocols. RNA was eluted using 20 μL nuclease-free water and stored at −80° C. until cDNA synthesis.

cDNA Synthesis and qPCR cDNA was synthesized from 6.25 ng RNA, diluted to 5 ng/μL using nuclease free water, in a 10 μL cDNA reaction mixture using the miRCURY LNA RT Kit (Qiagen Sciences, Germantown, MD). At the time of cDNA synthesis, spike-in miRNAs cel-miR-39-3p and UniSp6 (RNA Spike-In Kit, for RT, Qiagen Sciences, Germantown, MD) were added to the reaction mixture per the manufacturer's directions to allow for the detection of potential RT and PCR inhibitors. cDNA was diluted 110× and combined with an equal amount of 2× miRCURY SYBR Green Master Mix (Qiagen Sciences, Germantown, MD). Two independent samples were loaded onto the 384-well miRCURY LNA miRNA Human Serum/Plasma Focus miRNA PCR Panels (YAHS-106Y, Qiagen Sciences, Germantown, MD) and qPCR was performed on the 7900HT Fast Real-Time PCR System (Applied Biosystems, Foster City. CA). One additional proof-of-principle sample had been previously assessed using miRCURY LNA Human miRNome panels v3. miRNA expression values were extracted 1) for primers which were unchanged across panel versions and 2) primers that were altered across versions but had comparable amplification to the Focus panel (FIG. S1). CT and target amplification were assessed using SDS 2.4 software (Applied Biosystems/Thermo Fisher Scientific Waltham, MA).

Assessment of Erythrocyte Contamination of Plasma RNA

Plasma samples were assayed to assess potential erythrocyte RNA contamination as previously described (Balaraman et al., 2016; Mahnke et al., 2021b; Salem et al., 2020). Briefly, spectrophotometric analysis of plasma was used to detect the presence of free hemoglobin, with absorbance at 414 nm>0.3 as an indicator of possible hemolysis. Following RNA isolation, expression of erythrocyte-enriched transporter SLC4A1/BAND3 was assessed using the qScript cDNA Synthesis Kit (Quantabio, Beverly, MA) and PerfeCTa SYBR Green FastMix (Quantabio, Beverly, MA), and enrichment of erythrocyte miRNA was determined by comparing the expression of erythrocyte-enriched miR-451 to the expression of miR-23a which is stably-expressed in plasma ($\Delta CT_{hemolysis}=CT_{miR\text{-}23a}-CT_{miR\text{-}451}$) (Blondal et al., 2013). A $\Delta CT_{hemolysis}$ of >7 has been found to be a positive indicator of hemolysis (Blondal et al., 2013). We have previously seen in samples obtained from infants that absorbance alone is not reliable hemolysis marker (Mahnke et al., 2021b). likely due to the conversion of fetal to adult hemoglobin. Therefore, hemolysis was determined by both absorbance >0.3 and enrichment of erythrocyte miRNA ( ). Three samples met this exclusion criteria and were excluded from analysis.

Data Analysis

Data processing and modifications: CTs were assessed for each miRNA. CT values were normalized to the sample global mean of expression for all detected miRNAs (ΔCT) for each sample. We further examined miRNAs which were expressed in >80% of samples within a group. miRNAs with undetected CTs were considered expressed below the detectable limit and, therefore, were assigned at CT value 1 unit above the highest CT for that miRNA, as assigning these reactions values has been shown to reduce bias (McCall et al., 2014). Out of 179 assessed miRNAs, 171 miRNAs were expressed in >80% of the samples and had consistent amplification across panels and were further analyzed.

Statistical Approaches:

Univariate comparisons were conducted using, as appropriate, t-test or Wilcoxon rank-sum test for continuous variables and Chi-square test or Fisher's exact test for categorical variables. Comparisons between infants Pharmacologically-Treated and infants Not-Pharmacologically-Treated were conducted for maternal and infant sociodemographic and clinical factors, maternal substance use, and miRNA expression. In addition, miRNA comparisons between these two study groups were also conducted using ANCOVA models adjusted for gestational age (as a continuous variable). Effect sizes (Cohen's d (Cohen, 1988)) were calculated to compare miRNA expression between outcome groups. A moderate effect size of d>0.40 is indicative of clinically relevant alterations in expression (Hattie, 2009b: Rosenthal, 1994).

Predictive models were developed for the following outcomes: 1) severe NOWS requiring pharmacologic treatment, and 2) length of stay (LOS) of 14 days or more. Outcomes were first regressed on individual miRNA adjusted for gestational age using logistic regression. Predictive models were constructed by including multiple miRNAs with d>0.40 and a p-value<0.10 for gestational age-adjusted differences between infant groups. Forward step-wise logistic regression was used, with a criterion for entering the model of p-value<0.20 and final models included miRNAs with p-values<0.10. Firth's penalized likelihood approach was used to control for potential regression model convergence issues related to the small sample size (Firth, 1993; Heinze and Schemper, 2002). Additionally, since the same observations used to fit the model were being used to estimate the performance of the model, a second bias reduction method was also applied which estimated the predicted probability for a given observation by approximating the exclusion of that given observation when estimating regression parameter estimates (SAS Institute Inc., 2014). A probability ≥0.51 was used to determine predicted outcomes. Sensitivity. specificity, positive predicted value (PPV). and negative predictive value (NPV) and associated 95% confidence intervals (95% CI) were calculated. Receiver operating characteristic (ROC) curves were constructed and area under the ROC curve (AUC) was estimated for Firth-adjusted models. Sensitivity analyses included stratification by type of maternal third trimester MOUD exposure. A p-value less than 0.05 was considered to be statistically significant. All statistical analysis were conducted using R (R Core Team, 2020) and SAS 9.4 (Cary, NC).

Results:

Participant Characteristics

Participant demographic characteristics are summarized in 3, FIG. 19. Mean maternal age at recruitment was 28.7±5.8 years and participants were recruited, on average, during the second trimester (mean gestational age at recruitment: 21.5±7.2 weeks). Alongside buprenorphine and methadone MOUD, concurrent use of other opioids, i.e., heroin (36.2%) or misuse of opioid analgesics (37.9%) was prevalent but similar in both groups and no group differences in use of alcohol, tobacco, marijuana, benzodiazepines or other substances were observed. The sample was racially and ethnically diverse (74.1% Latinx and 6.9% Native Americans). Approximately a third of the women (34.5%) reported less than high school education level. A substantially higher proportion of Pharmacologically-Treated infants (64.7%) were prenatally exposed to methadone compared to Not-Pharmacologically-Treated (24.4%: p<0.01). There were no differences in maternal characteristics between the study groups except for a higher prevalence of Hepatitis C in Pharmacologically-Treated group (35.3%) compared to Not-Pharmacologically-Treated (22.0%) group (p=0.03).

Perinatal and infant characteristics are summarized in Table 4, FIG. 20. There were differences in the mean gestational age at delivery (36.9±1.0 vs. 38.8±1.4 weeks; p<0.0001) reflected in the higher incidence of preterm delivery in the Pharmacologically-Treated group compared to Not-Pharmacologically-Treated group (23.5% vs. 4.9%; p=0.06). LOS was significantly longer in the Pharmacologically-Treated (18.9±9.5 days) compared to Not-Pharmacologically-Treated group (6.0±3.9 days; p<0.01). Respiratory distress, a common sign indicating the need for pharmacologic treatment, was also significantly more prevalent in the Pharmacologically-Treated compared to Not-Pharmacologically-Treated group (47.1% vs 9.8%, p<0.01). No other differences in infant characteristics were observed.

Plasma and RNA Characteristics

Sample purity characteristics. There were no significant differences in hemolysis measures, including the presence of free hemoglobin and $\Delta CT_{hemolysis}$, when comparing Pharmacologically-Treated to Not-Pharmacologically-Treated or LOS≥14 days to LOS<14 days (all p's>0.10). There was also no significant correlation between sample absorbance at 414 nm and $\Delta CT_{hemolysis}$(r=0.22, p=0.094), therefore, samples were excluded from analysis only if it exceeded criterion on both measures (Mahnke et al.). There were no between-group differences in plasma total RNA concentration, qPCR amplification, or technical performance on focus panels (all p>0.10).

miRNA Expression by NOWS Severity Outcomes

Figure 23:
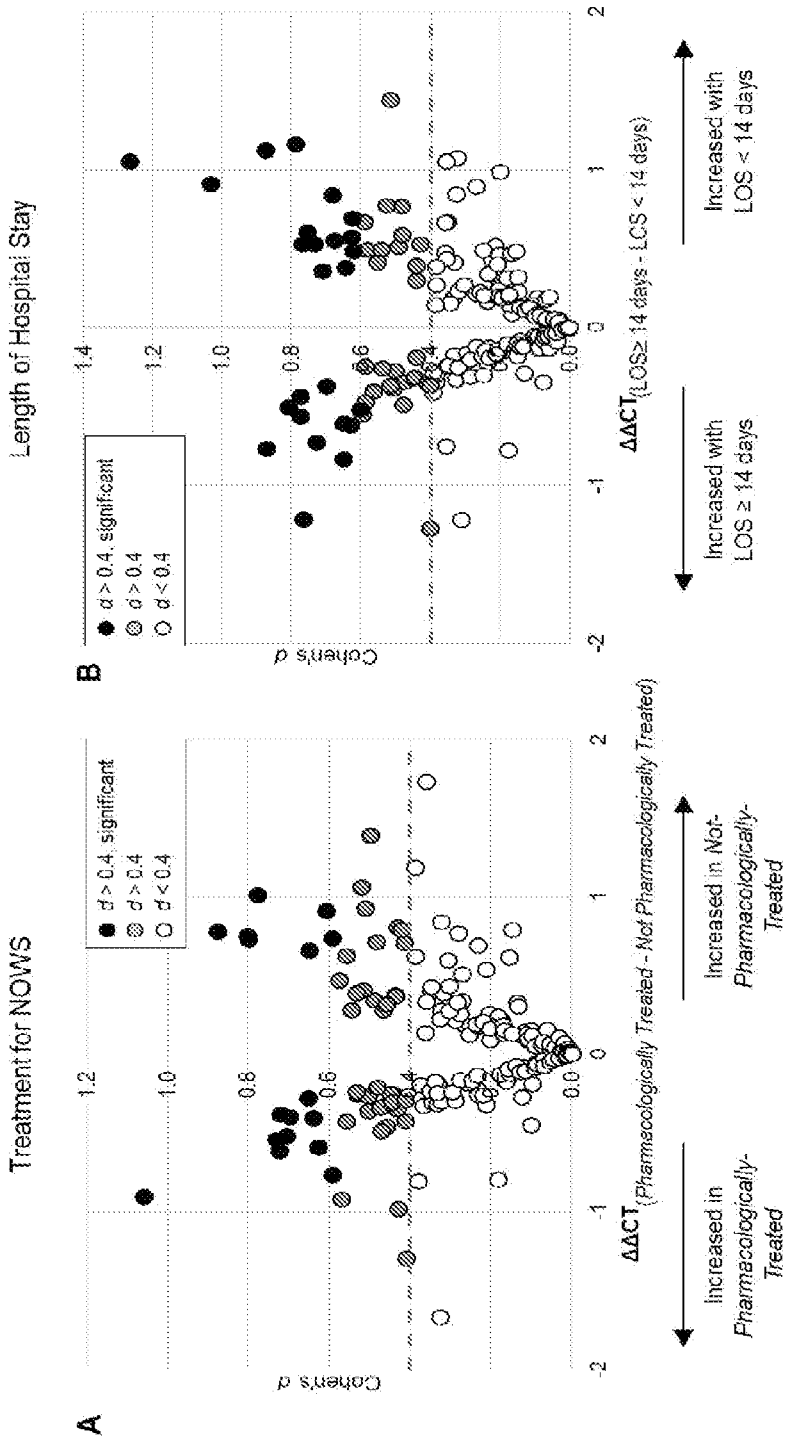
FIG. 23 shows altered miRNA expression and the effect size of expression change for pharmacologically-treated and extended hospital stay infants. Volcano plots of cord blood plasma extracellular miRNA expression (ΔΔCT) and effect size (Cohen's d) comparing miRNA expression in neonates Pharmacologically-Treated compared to Not-Pharmacologically-Treated (A) and in neonates with protracted length of stay (LOS≥14 days) compared to short to moderate hospital stays (LOS<14 days) (B). Grey filled points denote miRNAs altered with a clinically relevant effect size (d>0.4, dashed line). Black filled points denote miRNAs altered with a clinically relevant effect size that are significantly altered, with a 95% confidence interval that does not span zero.

At birth, neonates Pharmacologically-Treated, expressed a substantially different plasma extracellular miRNA expression profile compared neonates with POE who were Not-Pharmacologically-Treated (FIG. S3,). Of the 171 miRNAs assessed, 31.0% were altered with a clinically relevant effect size (Cohen's d≥0.40), and 9.9% were significantly altered with non-zero containing 95% confidence interval estimates (A). Of the miRNAs altered with a clinically relevant effect size, 45.3% were more highly expressed in neonates Pharmacologically-Treated while 54.7% exhibited higher expression in neonates Not-Pharmacologically-Treated. When miRNA expression was compared in neonates with prolonged hospitalization (LOS≥14 days) to neonates with LOS<14 days (FIG. 23B), 31.6% of miRNAs were altered with a clinically-relevant effect size and 14.6% were significantly altered with non-zero containing 95% confidence interval estimates. Equal numbers of miRNAs were upregulated in neonates with LOS≥14 days and neonates with LOS<14 days.

Predictive Models

When miRNAs were considered individually in gestational age-adjusted logistic regression models, there was considerable overlap between potentially predictive miRNA (p-values<0.20) for each of the two outcomes, treatment for NOWS and prolonged hospitalization. Preliminary logistic regressions were used to determine candidates for the predictive models. FIG. 21, Table 5 provides the miRNA expression values and results for preliminary logistic regressions where p<0.10. Ultimately, there were five 'finalist' miRNAs included in the predictive model for NOWS treatment and four miRNAs for LOS≥14 days (FIG. 4S,). Two miRNAs, hsa-miR-30c-5p and hsa-miR-629-5p, were predictive of treatment for NOWS and prolonged hospitalization.

Performance of Treatment-for-NOWS Predictive Model

The expression of five miRNAs, miR-421, miR-146-5p, miR-629-5p, miR-223-3p and miR-30c-5p, was found to be predictive of NOWS treatment. FIG. 22, provides the results of forward step-wise logistic regression analysis evaluating the predictive ability of the expression of these miRNAs on treatment for NOWS after adjusting for gestational age, and for type of MOUD. The contribution of each individual miRNA in the development of the LOS predictive model is shown in FIG. S4, Supplemental Table S4. The algorithm accuracy for the main analysis was 96.6%, and the AUC was 0.99. Sensitivity and specificity were both high, 94.1% (95% CI 71.3, 99.9) and 97.6% (95% CI 87.1, 99.9), respectively. Metrics were lower in the additional bias-adjusted analysis, which approximates the impact of excluding observations on model performance, but within the 95% CIs of the non-adjusted logistic regression model. Of the five miRNAs predictive for the need for pharmacological treatment, miR-421 and miR-629-5p were significantly (p<0.05) increased and miR-146-5p and miR-223-5p were significantly decreased in Pharmacologically-Treated neonates compared to the Not-Pharmacologically-Treated group.

Figure 24:
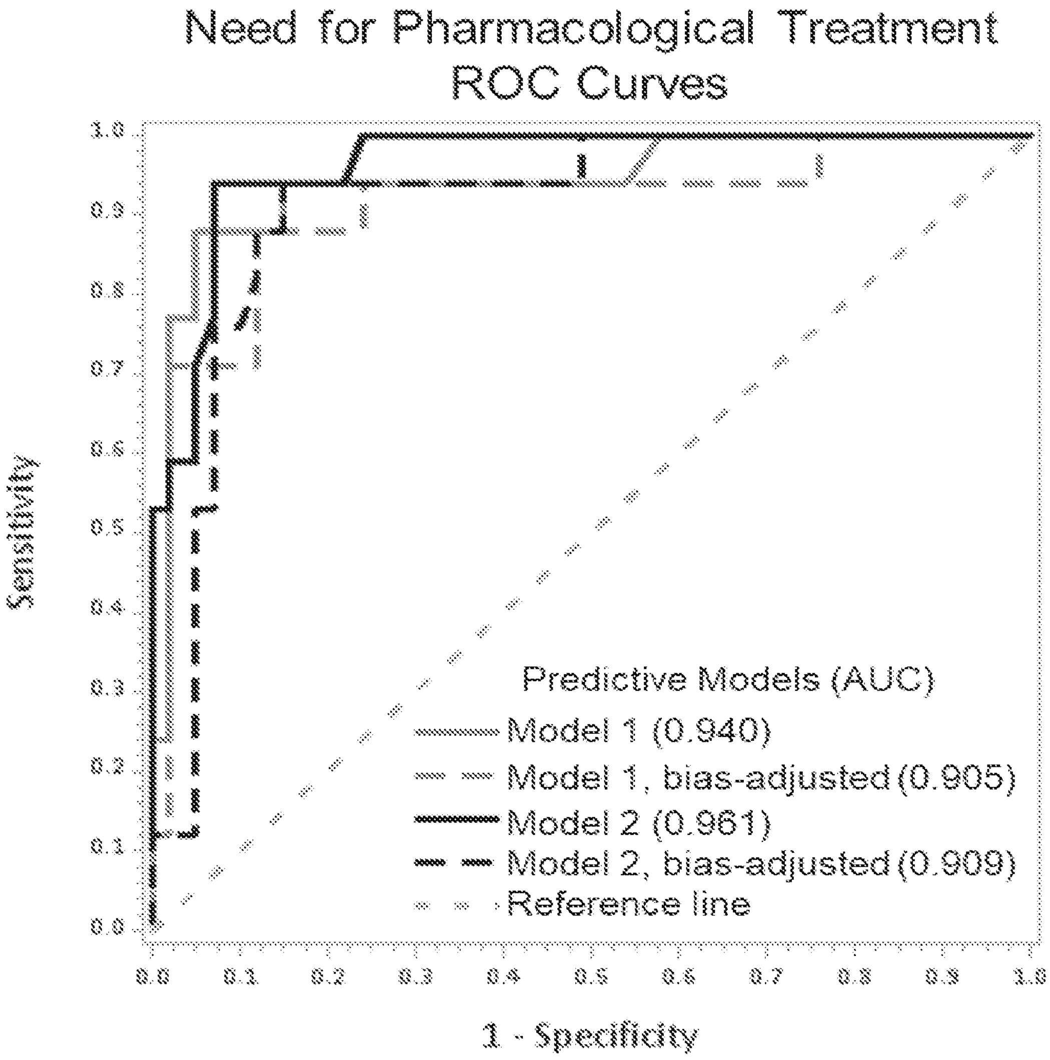
FIG. 24 shows receiver operating characteristic (ROC) curves for five miRNAs differentiating Treated-for NOWS and Non-Treated-for-NOWS infants. ROC curves were determined for model performance without (A) and with (B) adjustment for type of maternal MOUD. Model includes miRNAs miR-421, miR-146-5p, miR-629-5p, miR-223-3p and miR-30c-Sp. AUC: area under the ROC curve estimates; Firth: logistic regression model with estimates adjusted for small sample size using Firth's penalized likelihood approach; Firth, bias-adjusted: estimates the predicted probability for a given observation by approximating the exclusion of that given observation when estimating regression parameter estimates. ROC curves for performance of Model 1, containing miR-let-7d-5p, miR-128-3p, miR-30c-5p, miR-421, and miR-584-5p and Model 2, containing the same miRNAs and gestational age.
Figure 25:
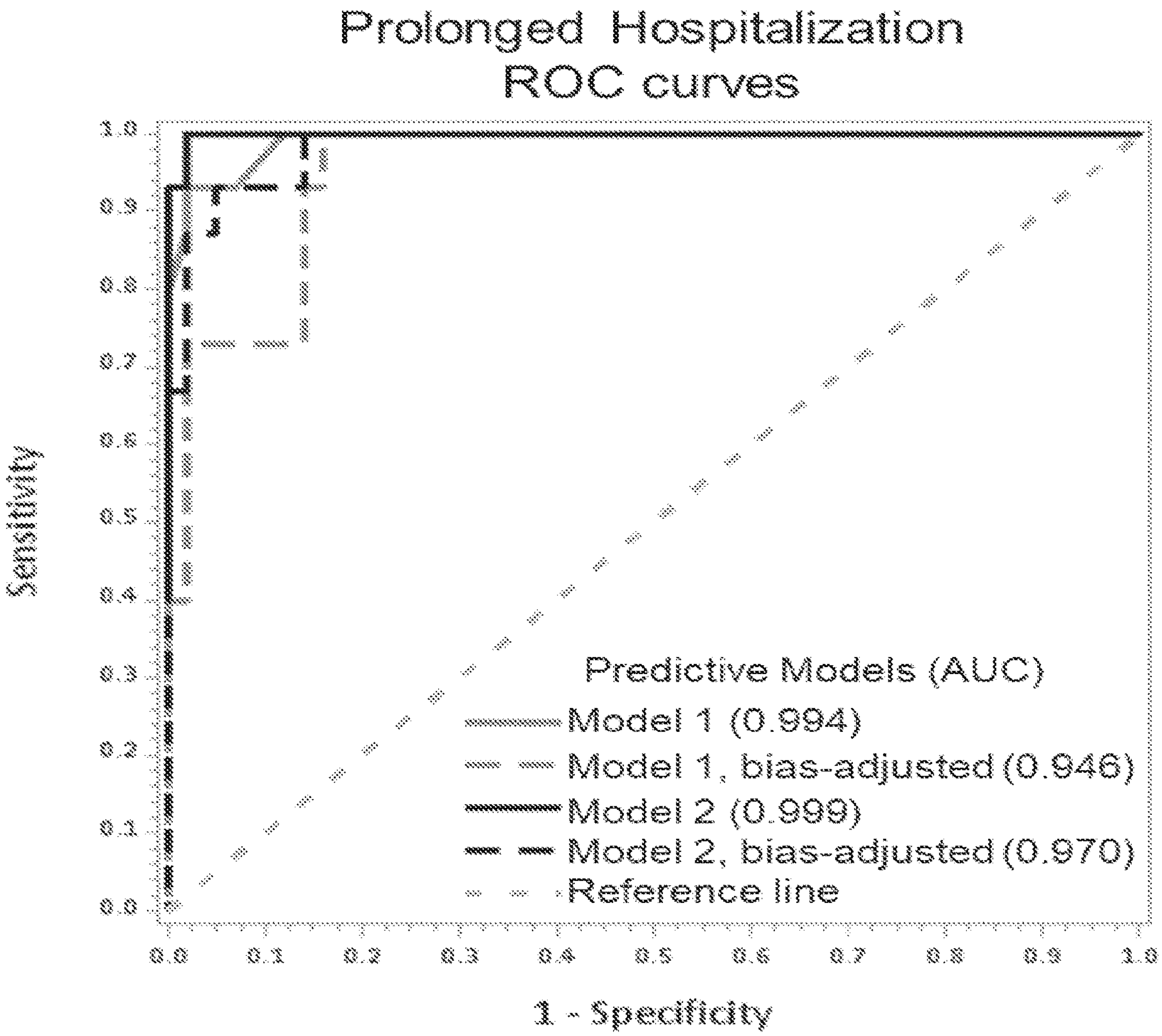
FIG. 25 shows receiver operating characteristic (ROC) curves for four miRNAs differentiating infants with prolonged hospitalization (>14 days) from those hospitalized for <14 days. ROC curves were determined without (A) and with (B) adjustment for type of maternal MOUD. Model includes miRNAs let-7b-5p, miR-30c-5p, miR-590-5p, and miR-629-5p. AUC: area under the ROC curve estimates; Firth: logistic regression model with estimates adjusted for small sample size using Firth's penalized likelihood approach; Firth, bias adjusted: estimates the predicted probability for a given observation by approximating the exclusion of that given observation when estimating regression parameter estimates. ROC curves for performance of Model 1, containing let-7b-5p, miR-10b-5p, miR-128-3p, miR-30c-5p, and miR-421, and Model 2, containing the same miRNAs and gestational age. For Model 2, miR-10b-5p was dropped from the model due to lack of convergence.

In stratified analyses, miRNA expression was compared among the study groups after stratification by the type of maternal MOUD. In that analysis, miR-421 had significantly higher expression in Pharmacologically-Treated neonates, compared to Not-Pharmacologically-Treated neonates, for both prenatal buprenorphine exposure and methadone exposure. In the subset with prenatal methadone exposure, there were differences in miR-146b-5p and miR-629-5p between Pharmacologically-Treated and Not-Pharmacologically-Treated groups, whereas those differences were not observed in the subset with prenatal buprenorphine exposure. In contrast, significant differences in miR-223-5p between the study groups were observed only in the subset of infants with prenatal buprenorphine exposure. ROC curves for the predictive model from the main analysis (Firth model), bias-adjusted analysis, models that include the type of maternal MOUD are shown in FIG. 24 These curves show high sensitivity and specificity for these miRNAs to predict extended hospital stay in all statistical models.

Performance of Extended Length of Hospital Stay Model

While neonates in both groups experienced an extended hospital length of stay, a majority, i.e., 76.5% of neonates with Pharmacologically-Treated had a LOS≥14 days whereas only 7.3% of neonates Not-Pharmacologically-Treated had a LOS≥14 days (FIG. 20, Table 4). The expression of four miRNAs, let-7b-5p, miR-30c-5p, miR-629-5p, and miR-590-5p, was found to be predictive of LOS≥14 days. FIG. 20, Table 4 provides results of forward step-wise logistic regression analysis evaluating predictive ability of the expression of these miRNAs on prolonged hospitalization after adjusting for gestational age and additionally MOUD. The contribution of each individual miRNA in the development of the LOS predictive model is shown in FIG. S4, Supplemental Table S4. The algorithm accuracy for the main analysis was 94.8%, and the AUC was 0.98. Sensitivity and specificity were both high, 87.5% (95% CI 61.6, 98.4) and 97.6% (95% CI 87.4, 99.9), respectively. Metrics were lower in the additional bias-adjusted analysis, but within the 95% CIs of the non-adjusted logistic regression model (FIG. 21, Table 5). Of the four miRNAs predictive of extended length of hospital stay, let-76-5p and miR-30c-5p were significantly (p<0.05) decreased and miR-629-5p was significantly increased in neonates with LOS≥14 days. In stratified analysis of neonatal miRNA expression by maternal MOUD exposure, miRNAs let-7b-5p, miR-30c-5p, and miR-590-5p had significantly lower expression in methadone-exposed neonates with LOS≥14 days compared to methadone-exposed neonates with LOS<14 days. ROC curves for the predictive model from the main analysis (Firth model) and additional bias-adjusted analysis and results for models that include type of maternal MOUD exposure are shown in 25. These curves show high sensitivity and specificity for these miRNAs to predict extended hospital stay in both the main analysis and the bias-adjusted analysis.

Discussion

Summary of the Key Findings

There is an unmet need for biomarkers to proactively identify prenatal opioid exposed neonates who are the most at risk for developing NOWS, particularly those with worse outcomes. We found that the expression of extracellular miRNAs in umbilical cord blood at the time of birth is different in infants who would go on to be treated for NOWS, prior to the onset of withdrawal symptoms. We also found that the extracellular cord blood miRNAs are also altered in infants that go on to have a hospital stay of 14 days or longer. We further found that five miRNAs could predict, with high sensitivity and specificity (both >94%), neonates that would be treated for NOWS, and that four miRNAs could predict neonates with a hospital stay ≥14 days (sensitivity and specificity >87%).

- Comparison with existing literature
  - miRNA biomarker/epigenetic biomarker literature
    - As the inventors have previously reported in infancy (Mahnke et al., 2021b), hemolytic values are not related. This is in contrast to their relationship in plasma in adults (Shah et al., 2016) and indicates the presence of free hemoglobin that is not due to hemolysis, and instead may be a reflection of conversions from fetal to adult hemoglobin.
    - Increased DNA promoter methylation in the promoter region of the mu opioid receptor (OPRM1) gene is associated with increased medication need for NOWS treatment (Wachman et al., 2014).
    - In a rodent model, POE altered extracellular miRNA content in the developing brain (Shahjin et al., 2019). and these altered miRNAs were shown to impair neural development The predictive models constructed here consist of multiple miRNAs. It has been previously found that circulating miRNAs act in groups. For example, using confirmatory factor analysis we found that groups of miRNAs well explained the variance in miRNA in between infants prenatally exposed to alcohol and control neonates, and that these groups of miRNAs can mediate effects of prenatal alcohol, including growth, these miRNAs groups are enriched for targeting mRNAs of different growth and developmental pathways, and as a group these miRNAs partially mediate alcohol-exposure induced growth and neurodevelopmental deficits (Mahnke et al., 2021b). Moreover, we previously identified a group of miRNAs in pregnant women that, in mid-pregnancy, were predictive of child outcome following prenatal alcohol exposure (Balaraman et al., 2016). These predictive miRNAs as a group inhibited growth in human placental cell lines, an emergent phenotype that was not due to the summation of the individual effects of each miRNA (Tseng et al., 2019). Additionally, we found that these miRNAs collectively, when administered to pregnant mouse dams, impaired fetal and placental growth in the absence of alcohol. These data suggest miRNAs are powerful mediators of the effects of prenatal drug exposure and that the miRNAs that were predictive of treatment-for-NOWS and LOS≥14 days may act, in concert, to mediate the effects of prenatal opioid exposure.

Discussion about differences in miRNAs identified for treated/non-treated for NOWS vs LOS Intriguingly, of the miRNAs that were altered in these neonates, only 37.9% were changed in both Treated-for-NOWS and LOS≥14 days, indicating that miRNAs which predict the likelihood of an extended hospital stay reflect, in part, different biological changes than those miRNAs that indicate vulnerability to developing NOWS.

Insights about mechanisms MiRNAs exert translation control in cells and tissues by binding to the 3'-untranslated region (UTR) of target mRNAs and repressing translation. A number of miRNAs have also been documented to regulate opioid signaling by targeting the 3'-UTR of the μ opioid receptor (OPRM1) mRNA and, moreover, the expression of these miRNAs can be reciprocally altered by opioid receptor signaling (Barbierato et al., 2015; Hwang et al., 2012). Although the majority of candidate miRNAs identified here were not directly opioid signaling-associated, 16.7% of candidate miRNAs in our study were members of the let-7 miRNA family, which has been shown by in silico analysis (Barbierato et al., 2015; Hwang et al., 2012) and in cell culture (He et al., 2010) to target OPRM1. For example, morphine tolerance occurs due to a reduction in μ-opioid receptor protein expression, which was found to be mediated, in part, by increased let-7 expression in human cell lines and a mouse model of chronic morphine administration (He et al., 2010). We found that four of the five let-7 family members in the miRNA candidates were decreased either in the treated-for-NOWS or LOS≥14 days neonates, and in particular, decreased let-7b-5p expression was predictive of LOS≥14 days. These data suggest that let-7 sensitization of the opioid receptor may be altered in neonates vulnerable to more severe NOWS. Interestingly, previous work has shown that DNA hypermethylation upstream of the OPRM1 coding region, which likely decreases OPRM1 transcription, is associated with more severe NOWS that requires additional medication (Wachman et al., 2014). Therefore, the decreased let-7b-5p in circulation may be reflective of adaptive mechanisms to increase opioid receptor sensitivity or may reflect a biphasic opioid receptor response to prenatal opioid exposure in neonates that are treated for NOWS. More research is needed to understand how these two epigenetic regulatory mechanisms may interplay to affect u opioid receptor expression and the contribution to worse outcomes following prenatal opioid exposure.

Perinatal opioid exposure has been shown to increase inflammatory cytokines and potentiate response to subsequent immune challenges in a rat model (Jantzie et al., 2020). The miRNAs in circulation we identified as predictive of LOS≥14 days have been previously implicated in modulating inflammatory tone and may contribute to this pro-inflammatory state previously seen with opioid exposure. For example, miR-30c-5p, was decreased in both the treated-for-NOWS and in LOS≥14 days predictive models. In an a study of circulating miRNAs and atherosclerosis, decreased miR-30c-5p in plasma was associated with development of carotid plaques, and in vitro, decreased miR-30c-5p expression in monocyte-derived macrophages increased release of pro-inflammatory cytokine, IL-1β (Ceolotto et al., 2017). In our work examining infant circulating miRNA expression following prenatal alcohol exposure, we found that miR-30c-5p was elevated by prenatal alcohol exposure and factor analysis showed that miR-30c-5p clustered with miRNAs that together are enriched targeting mRNAs associated with the immune system and inflammation (Mahnke et al., 2021b). Moreover, this group of immune and inflammation-related miRNAs partially mediated the effects of prenatal alcohol exposure on infant length and neurodevelopment, suggesting that alterations to inflammation and immune response miRNAs in infancy can impact infant growth and development. Additional miRNAs from the LOS≥14 days predictive model are also implicated in inflammation. miR-590-5p, which was decreased by LOS≥14 days, when inhibited in vitro increased pro-inflammatory TNFα and decreased anti-inflammatory IL-10 release from adult human-derived monocytes (Long et al., 2016), and when overexpressed in human umbilical vein endothelial cells decreased release of pro-inflammatory cytokines (Dai et al., 2016). Decreased plasma levels of let-7b-5p, as was found with LOS≥14 days, was associated with increased levels of TNFα in patients with endometriosis and inhibition of let-7b-5p expression in a macrophage cell line stimulated the release of additional cytokines, including proinflammatory IL-1β (Nematian et al., 2018). These data suggest that alterations to inflammatory tone are reflected by the miRNAs in the LOS≥14 days model and that these miRNAs may also contribute or mediate some changes to inflammation following prenatal opioid exposure.

Opioids and mu opioid receptor signaling have been shown to promote cell proliferation and migration, particularly through the epithelial-mesenchymal transition (EMT) pathway, in endothelial and cancer cells (Dai et al., 2010; Lennon et al., 2014). Appropriate timing of EMT is pivotal in development (Acloque et al., 2009), and the profile of miRNAs predictive of treatment for NOWS indicate that these pathways may be disrupted in neonates treated for NOWS. Both miR-146b-5p and miR-30c-5p were decreased in Treated-for-NOWS neonates and both have been shown to affect the EMT pathway in cancer cell lines. Overexpression of either miR-30c-5p or miR-146b-5p was shown to inhibit EMT (Cao et al., 2017; Li et al., 2020) and inhibition of miR-146b-5p promoted EMT (Yang et al., 2018). miR-421 was increased in Treated-for-NOWS neonates and has been shown to both promote EMT, by directly targeting E-cadherin (Ji et al., 2020), and block EMT, through actions on the EMT regulator SOX4 (Li et al., 2019). The altered expression of the miRNAs in the predictive of treatment for NOWS model suggest that plasma miRNAs are shifted to promote EMT, or decrease the reciprocal developmental pathway, mesenchymal-epithelial transition (MET). While the impact of dysregulated EMT/MET balance during the neonatal period is not known, loss of mesenchymal cell maintenance in adult mouse tissues, through loss of developmental EMT/MET balance regulator Wt1, disrupts homeostasis and induces hypertrophy in a number of organs (Chau et al., 2011), and in development, multiple rounds of EMT and MET are needed for embryonic development and organogenesis (Lim and Thiery, 2012). Changes neonatal EMT/MET, either due to or reflected by miRNAs that were predictive of NOWS, may have impacts for a number of NOWS symptoms including those related to dysmaturation of the autonomic nervous system (Mulkey and Plessis, 2018).

Example 5—Further Analysis 51 miRNAs were identified as being relevant to the analysis of miRNAs to establish NOWS and a recommendation for treatment in a neonatal patient or subject pursuant to the present invention. FIG. 26 shows a complete list of the 51 miRNAs which were identified and can be used to diagnose NOWS in a neonate and the advisability/requirement of pharmacological treatment and/or long-term hospital stay (at least 14 days). FIG. 26 also identifies the sequence of each miRNA, the MIMAT number for each sequence, the relevance of the miRNA to the diagnosis of NOWS and therapy (both pharmacological treatment and/or long term hospitalization) as indicated and whether the relevance of the individual miRNA to the diagnosis and/or monitoring of therapy is expressed as an overexpression (up-regulation, in bold print) or underexpression (down-regulation, in italicized print) of the miRNA which would support the diagnosis of NOWS and treatment recommendation. Thus, if one were to analyze for miR-128-3p (SEQ ID NO:3), the overexpression or up-regulation of that miRNA in a neonate blood sample, preferably a plasma sample obtained from umbilical cord or placental blood would be predictive of NOWS. The same would be true for the other miRNAs which are listed in bold accordingly in FIG. 26. Likewise, if one were to analyze for miR-30c-5p (SEQ ID NO:14), the underexpression or down-regulation of that miRNA in a neonatal blood sample would be predictive of NOWS, as would similar miRNAs listed in italics in FIG. 26.

Using the selection criteria, the 51 potential miRNA presented in FIG. 26 were identified for at least one of the two outcomes, pharmaceutical treatment (n=35) or LOS≥14 days (n=41). Final miRNA signature (identified using a stepwise logistic regression model) resulted in 5 miRNAs for each of NOWS outcomes (3 miRNAs were common across both outcomes)—Tier A. The '2$^{nd}$ tier' (Tier B) models identified additional 6 miRNA for each NOWS outcome and the 3$^{rd}$ Tier (Tier C) identified additional miRNAs, as presented in FIG. 27, Table 7 shows analyses for the identification of miRNAs from the list of 51 relevant miRNAs tiered for relevance for the diagnosis of NOWS in a neonate. Ultimately, the Tier C final predictive models included 4 miRNA for pharmaceutical treatment and 6 miRNA for LOS≥14 days.

In a predictive model for receipt of pharmacologic treatment including predicted probabilities from the 3 Tier group models (A, B, and C), Tier Group C was not significant (p=0.80). In a model that included miRNAs from Tier Group A and B, the resultant AUC was 0.963 (bias-adjusted AUC=0.920), p<0.05. In a predictive model for LOS≥14 days, Tier Group B was not significant (p=0.76). In a model that included miRNAs from Tier Group A and C, the resultant AUC 0.998 (bias-adjusted AUC=0.98), p<0.10. FIG. 28, Table 8 shows the validity indices associated with miRNA clusters for all tier Models based upon the performance of tiered miRNA clusters, in combination, for predicting NOWS outcomes. Table 8 shows performance for all three tiers and as well as after dropping non-significant tiers (do not significantly improve model performance beyond the tiers already in the model). Included in the prediction model are the predicted probability estimates associated with each of the Tier groups. The parameter estimates represent the increase (decrease) associated with the probability of the outcome (pharmacologic treatment or LOS≥14 days) for each unit increase in estimated probability for the Tier (For example, for the Tier A, B, C pharmacologic treatment model, an increase of 1% in estimated probability from Tier A increases the probability of pharmacologic treatment by 4.69.)

REFERENCES

Acloque, H., Adams, M.S., Fishwick, K., Bronner-Fraser, M., and Nieto, M.A. (2009). Epithelial-mesenchymal transitions: the importance of changing cell state in development and disease. J Clin Invest 119, 1438-1449. 10.1172/JCI38019.

Al-Hashimi, M., Scott, S.W.M., Thompson, J.P., and Lambert, D.G. (2013). Opioids and immune modulation: more questions than answers. British journal of anaesthesia 111, 80-88. 10.1093/bja/act153.

Ambros, V. (2004). The functions of animal microRNAs. Nature 431, 350-355. 10.1038/nature02871.

American College of Obstetricians and Gynecologists (2017). Opioid Use and Opioid Use Disorder in Pregnancy. Committee Opinion No. 711. Obstetrics & Gynecology 130, e81-e94. 10.1097/aog.0000000000002235.

Bagley, S., Wachman, E.M., Holland, E., and Brogly, S.B. (2014). Review of the assessment and management of neonatal abstinence syndrome. Addiction Science & Clinical Practice 9, 19-19. 10.1186/1940-0640-9-19.

Bakhireva, L.N., Cano, S., Rayburn, W.F., Savich, R.D., Leeman, L., Anton, R.F., and Savage, D.D. (2012). Advanced gestational age increases scrum carbohydrate-deficient transferrin levels in abstinent pregnant women. Alcohol and alcoholism (Oxford, Oxfordshire) 47, 683-687. 10.1093/alcalc/ags087.

Bakhireva, L.N., Holbrook, B.D., Shrestha, S., Leyva, Y., Ashley, M., Cano, S., Lowe, J., Stephen, J.M., and Leeman, L. (2019). Association between prenatal opioid exposure, neonatal opioid withdrawal syndrome, and neurodevelopmental and behavioral outcomes at 5-8 months of age. Early Hum Dev 128, 69-76. 10.1016/j.earlhumdev.2018.10.010.

Bakhireva, L.N., Leeman, L., Savich, R.D., Cano, S., Gutierrez, H., Savage, D.D., and Rayburn, W.F. (2014). The validity of phosphatidylethanol in dried blood spots of newborns for the identification of prenatal alcohol exposure. Alcoholism, clinical and experimental research 38, 1078-1085. 10.1111/acer.12349.

Bakhireva, L.N., Lowe, J.R., Gutierrez, H.L., and Stephen, J.M. (2015). Ethanol, Neurodevelopment, Infant and Child Health (ENRICH) prospective cohort: Study design considerations. Adv Pediatr Res 2. 10.12715/apr.2015.2.10.

Bakhireva, L.N., and Savage, D.D. (2011). Focus on: biomarkers of fetal alcohol exposure and fetal alcohol effects. Alcohol research & health: the journal of the National Institute on Alcohol Abuse and Alcoholism 34, 56-63.

Balaraman, S., Schafer, J.J., Tseng, A.M., Wertelecki, W., Yevtushok, L., Zymak-Zakutnya, N., Chambers, C.D., and Miranda, R.C. (2016). Plasma miRNA profiles in pregnant women predict infant outcomes following prenatal alcohol exposure. PLOS One 11, e0165081. 10.1371/journal.pone.0165081.

Baldacchino, A., Arbuckle, K., Petrie, D.J., and McCowan, C. (2015). Erratum: neurobehavioral consequences of chronic intrauterine opioid exposure in infants and preschool children: a systematic review and meta-analysis. BMC Psychiatry 15, 134. 10.1186/s12888-015-0438-5.

Bär, C., Thum, T., and de Gonzalo-Calvo, D. (2019). Circulating miRNAs as mediators in cell-to-cell communication. Epigenomics 11, 111-113. 10.2217/epi-2018-0183.

Barbierato, M., Zusso, M., Skaper, S.D., and Giusti, P. (2015). MicroRNAs: emerging role in the endogenous mu opioid system. CNS Neurol Disord Drug Targets 14, 239-250. 10.2174/1871527314666150116123932.

Bartel, D.P. (2004). MicroRNAs: genomics, biogenesis, mechanism, and function. Cell 116, 281-297. 10.1016/s0092-8674(04)00045-5.

Beauchamp, K.G., Lowe, J., Schrader, R.M., Shrestha, S., Aragon, C., Moss, N., Stephen, J.M., and Bakhireva, L.N. (2020). Self-regulation and emotional reactivity in infants with prenatal exposure to opioids and alcohol. Early Hum Dev 148, 105119. 10.1016/j.earlhumdev.2020.105119.

Blondal, T., Jensby Nielsen, S., Baker, A., Andreasen, D., Mouritzen, P., Wrang Teilum, M., and Dahlsveen, I.K. (2013). Assessing sample and miRNA profile quality in serum and plasma or other biofluids. Methods 59, S1-6. 10.1016/j.ymeth.2012.09.015.

Cao, J.M., Li, G.Z., Han, M., Xu, H.L., and Huang, K.M. (2017). MiR-30c-5p suppresses migration, invasion and epithelial to mesenchymal transition of gastric cancer via targeting MTA1. Biomed Pharmacother 93, 554-560. 10.1016/j.biopha.2017.06.084.

Ceolotto, G., Giannella, A., Albiero, M., Kuppusamy, M., Radu, C., Simioni, P., Garlaschelli, K., Baragetti, A., Catapano, A.L., Iori, E., et al. (2017). miR-30c-5p regulates macrophage-mediated inflammation and pro-atherosclerosis pathways. Cardiovasc Res 113, 1627-1638. 10.1093/cvr/cvx157.

Chau, Y.Y., Brownstein, D., Mjoseng, H., Lee, W.C., Buza-Vidas, N., Nerlov, C., Jacobsen, S.E., Perry, P., Berry, R., Thornburn, A., et al. (2011). Acute multiple organ failure in adult mice deleted for the developmental regulator Wt1. PLOS Genet 7, e1002404. 10.1371/journal.pgen.1002404.

Chavan, N.R., Ashford, K.B., Wiggins, A.T., Lofwall, M.R., and Critchfield, A.S. (2017). Buprenorphine for Medication-Assisted Treatment of Opioid Use Disorder in Pregnancy: Relationship to Neonatal Opioid Withdrawal Syndrome. AJP Rep 7, e215-e222. 10.1055/s-0037-1608783.

Cohen, J. (1988). Statistical Power Analysis For the Behavioral Sciences, 2nd ed Edition (L. Erlbaum Associates).

Dai. X., Song. H.J., Cui, S.G., Wang, T., Liu, Q., and Wang, R. (2010). The stimulative effects of endogenous opioids on endothelial cell proliferation, migration and angiogenesis in vitro. Eur J Pharmacol 628, 42-50. 10.1016/j.ejphar.2009.11.035.

Dai, Y., Zhang, Z., Cao, Y., Mehta, J.L., and Li, J. (2016). MiR-590-5p Inhibits Oxidized-LDL Induced Angiogenesis by Targeting LOX-1. Sci Rep 6, 22607. 10.1038/srep22607.

Doberczak, T.M., Kandall, S.R., and Wilets, I. (1991). Neonatal opiate abstinence syndrome in term and preterm infants. J Pediatr 118, 933-937. 10.1016/s0022-3476(05)82214-0.

Finnegan, L.P., Connaughton, J.F., Kron, R.E., and Emich, J.P. (1975). Neonatal abstinence syndrome: assessment and management. Addictive diseases 2, 141-158.

Firth, D. (1993). Bias Reduction of Maximum Likelihood Estimates. Biometrika 80, 27-38. 10.2307/2336755.

Ganguli, A., Mostafa, A., Berger, J., Aydin, M.Y., Sun. F., Ramirez, S.A.S., Valera, E., Cunningham, B.T., King, W.P., and Bashir, R. (2020). Rapid isothermal amplification and portable detection system for SARS-COV-2. Proc Natl Acad Sci USA 117, 22727-22735. 10.1073/pnas.2014739117.

Gardiner, A.S., Gutierrez, H.L., Luo. L., Davies, S., Savage, D.D., Bakhireva, L.N., and Perrone-Bizzozero, N.I. (2016). Alcohol use during pregnancy is associated with specific alterations in microRNA levels in maternal serum. Alc Clin Exp Res In press.

Gill, P., and Ghaemi, A. (2008). Nucleic acid isothermal amplification technologies: a review. Nucleosides Nucleotides Nucleic Acids 27, 224-243. 10.1080/15257770701845204.

Gopman, S. (2014). Prenatal and Postpartum Care of Women with Substance Use Disorders. Obstetrics and Gynecology Clinics of North America 41, 213-228. 10.1016/j.ogc.2014.02.004.

Grossman, M.R., Berkwitt, A.K., Osborn, R.R., Xu, Y., Esserman, D.A., Shapiro, E.D., and Bizzarro, M.J. (2017). An Initiative to Improve the Quality of Care of Infants With Neonatal Abstinence Syndrome. Pediatrics 139. 10.1542/peds.2016-3360.

Haight, S.C., Ko, J.Y., Tong, V.T., Bohm, M.K., and Callaghan, W.M. (2018). Opioid Use Disorder Documented at Delivery Hospitalization—United States, 1999-2014. MMWR Morb Mortal Wkly Rep 67, 845-849. 10.15585/mmwr.mm6731a1.

Hattie, J. (2009a). Visible learning: a synthesis of over 800 meta-analyses relating to achievement (Routledge).

Hattie, J. (2009b). Visible Learning: a Synthesis of over 800 Meta-analyses Relating to Achievement (Routledge).

He, Y., Yang. C., Kirkmire, C.M., and Wang, Z.J. (2010). Regulation of opioid tolerance by let-7 family microRNA targeting the mu opioid receptor. J Neurosci 30, 10251-10258. 10.1523/JNEUROSCI.2419-10.2010.

Healthcare Cost and Utilization Project (2021). HCUP Fast Stats—Neonatal Abstinence Syndrome (NAS) Among Newborn Hospitalizations. website:hcup-us.abrq.gov/faststats/nas/nasquery.jsp?setting1=IP&location=US.

Heinze. G., and Schemper, M. (2002). A solution to the problem of separation in logistic regression. Stat Med 21, 2409-2419. 10.1002/sim.1047.

Herzlinger, R.A., Kandall, S.R., and Vaughan, H.G., Jr. (1977). Neonatal seizures associated with narcotic withdrawal. J Pediatr 91, 638-641. 10.1016/s0022-3476(77)80523-4.

Hudak, M.L., and Tan, R.C. (2012). Neonatal drug withdrawal. Pediatrics 129, 2011-3212.

Hwang, C.K., Wagley, Y., Law, P.Y., Wei, L.N., and Loh, H.H. (2012). MicroRNAs in opioid pharmacology. J Neuroimmune Pharmacol 7, 808-819. 10.1007/s11481-011-9323-2.

Isemann. B.T., Stoeckle, E.C., Taleghani, A.A., and Mueller. E.W. (2017). Early Prediction Tool to Identify the Need for Pharmacotherapy in Infants at Risk of Neonatal Abstinence Syndrome. Pharmacotherapy 37, 840-848. 10.1002/phar.1948.

Jacobson, S.W., Chiodo, L.M., Sokol, R.J., and Jacobson, J.L. (2002). Validity of maternal report of prenatal alcohol, cocaine, and smoking in relation to neurobehavioral outcome. Pediatrics 109, 815-825. 10.1542/peds.109.5.815.

Jansson, L.M., and Patrick, S.W. (2019). Neonatal Abstinence Syndrome. Pediatr Clin North Am 66, 353-367. 10.1016/j.pcl.2018.12.006.

Jantzie, L.L., Maxwell. J.R., Newville, J.C., Yellowhair. T.R., Kitase, Y., Madurai, N., Ramachandra, S., Bakhireva, L.N., Northington, F.J., Gerner, G., et al. (2020). Prenatal opioid exposure: The next neonatal neuroinflammatory disease. Brain, Behavior, and Immunity 84, 45-58. https://doi.org/10.1016/j.bbi.2019.11.007.

Ji, Y., Feng, G., Hou, Y., Yu, Y., Wang, R., and Yuan, H. (2020). Long noncoding RNA MEG3 decreases the growth of head and neck squamous cell carcinoma by regulating the expression of miR-421 and E-cadherin, Cancer Med 9, 3954-3963. 10.1002/cam4.3002.

Jones, H.E., Seashore, C., Johnson, E., Horton, E., O'Grady, K.E., and Andringa, K. (2016). Measurement of neonatal abstinence syndrome: Evaluation of short forms. J Opioid Manag 12, 19-23. 10.5055/jom.2016.0308.

Kaltenbach, K., O'Grady, K.E., Heil, S.H., Salisbury, A.L., Coyle, M.G., Fischer, G., Martin, P.R., Stine, S., and Jones, H.E (2018). Prenatal exposure to methadone or buprenorphine: Early childhood developmental outcomes. Drug Alcohol Depend 185, 40-49. 10.1016/j.drugalcdep.2017.11.030.

Kandall, S.R., Albin, S., Gartner, L.M., Lee, K.S., Eidelman, A., and Lowinson, J. (1977). The narcotic-dependent mother: fetal and neonatal consequences. Early Hum Dev 1, 159-169. 10.1016/0378-3782(77)90017-2.

Koshkin, A.A., Singh, S.K., Nielsen, P., Rajwanshi, V.K., Kumar, R., Meldgaard, M., Olsen, C.E., and Wengel, J. (1998). LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron 54, 3607-3630. https://doi.org/10.1016/S0040-4020(98)00094-5.

Larson, J.J., Graham, D.L., Singer, L.T., Beckwith, A.M., Terplan, M., Davis, J.M., Martinez, J., and Bada, H.S. (2019). Cognitive and Behavioral Impact on Children Exposed to Opioids During Pregnancy. Pediatrics 144. 10.1542/peds.2019-0514.

Leeman, L.M., Brown, S.A., Albright, B., Skipper, B., Hsi, A., and Rayburn, W.F. (2011). Association between intrapartum fetal heart rate patterns and neonatal abstinence syndrome in methadone exposed neonates. The journal of maternal-fetal & neonatal medicine: the official journal of the European Association of Perinatal Medicine, the Federation of Asia and Oceania Perinatal Societies, the International Society of Perinatal Obstetricians 24, 955-959. 10.3109/14767058.2010.536863.

Lennon, F.E., Mirzapoiazova, T., Mambetsariev, B., Poroyko, V.A., Salgia, R., Moss, J., and Singleton, P.A. (2014). The Mu opioid receptor promotes opioid and growth factor-induced proliferation, migration and Epithelial Mesenchymal Transition (EMT) in human lung cancer. PLOS One 9, e91577. 10.1371/journal-.pone.0091577.

Lewis, T., Dinh, J., and Leeder, J.S. (2015). Genetic determinants of fetal opiate exposure and risk of neonatal abstinence syndrome: Knowledge deficits and prospects for future research. Clin Pharmacol Ther 98, 309-320. 10.1002/cpt.159.

Li, S., Hao, J., Hong, Y., Mai, J., and Huang, W. (2020). Long Non-Coding RNA NEAT1 Promotes the Proliferation, Migration, and Metastasis of Human Breast-Cancer Cells by Inhibiting miR-146b-5p Expression. Cancer Manag Res 12, 6091-6101. 10.2147/CMAR.S252295.

Li, Y., Han, X., Li, Q., Wang, C., Lou, Z., and Wang, X. (2019). Long noncoding RNA HOXD-AS1 induces epithelial-mesenchymal transition in breast cancer by acting as a competing endogenous RNA of miR-421. J Cell Biochem 120, 10633-10642. 10.1002/jcb.28353.

Lim, J., and Thiery, J.P. (2012). Epithelial-mesenchymal transitions: insights from development. Development 139, 3471-3486. 10.1242/dev.071209.

Long, X., Li, Y., Qiu, S., Liu, J., He, L., and Peng, Y. (2016). MiR-582-5p/miR-590-5p targeted CREB1/CREB5-NF-kappaB signaling and caused opioid-induced immunosuppression in human monocytes. Transl Psychiatry 6, e757. 10.1038/tp.2016.4.

Mahnke, A.H., Sideridis, G.D., Salem, N.A., Tseng, A.M., Carter, R.C., Dodge, N.C., Rathod, A.B., Molteno, C.D., Meintjes, E.M., Jacobson, S.W., et al. (2021a). Infant circulating MicroRNAs as biomarkers of effect in fetal alcohol spectrum disorders. Scientific reports 11, 1429. 10.1038/s41598-020-80734-y.

Mahnke, A.H., Sideridis, G.D., Salem, N.A., Tseng, A.M., Carter, R.C., Dodge, N.C., Rathod, A.B., Molteno, C.D., Meintjes, E.M., Jacobson, S.W., et al. (2021b). Infant circulating MicroRNAs as biomarkers of effect in fetal alcohol spectrum disorders. Scientific Reports 11, 1429. 10.1038/s41598-020-80734-y.

McCall, M.N., McMurray, H.R., Land, H., and Almudevar, A. (2014). On non-detects in qPCR data. Bioinformatics 30, 2310-2316. 10.1093/bioinformatics/btu239.

McGlone, L., and Mactier, H. (2015). Infants of opioid-dependent mothers: neurodevelopment at six months. Early Hum Dev 91, 19-21. 10.1016/j.earlhumdev.2014.10.006.

Monnelly, V.J., Anblagan, D., Quigley, A., Cabez, M.B., Cooper, E.S., Mactier, H., Semple, S.I., Bastin, M.E., and Boardman, J.P. (2018). Prenatal methadone exposure is associated with altered neonatal brain development. Neuroimage Clin 18, 9-14. 10.1016/j.nicl.2017.12.033.

Mulkey, S.B., and Plessis, A.D. (2018). The Critical Role of the Central Autonomic Nervous System in Fetal-Neonatal Transition. Semin Pediatr Neurol 28, 29-37. 10.1016/j.spen.2018.05.004.

National Academies of Sciences Engineering and Medicine (U.S.). Committee on Medication-Assisted Treatment for Opioid Use Disorder, Leshner, A.I., Mancher, M., National Academies of Sciences Engineering and Medicine (U.S.). Board on Health Sciences Policy., and National Academies of Sciences Engineering and Medicine (U.S.). Health and Medicine Division. (2019). Medications for opioid use disorder save lives (The National Academies Press).

National Survey on Drug Use and Health ICPSR 34481-v3. Ann Arbor (MI): US Department of Health and Human Services, Substance Abuse and Mental Health Services Administration. Center for Behavioral Health Statistics and Quality; 2011.

Nematian, S.E., Mamillapalli, R., Kadakia, T.S., Majidi Zolbin, M., Moustafa, S., and Taylor, H.S. (2018). Systemic Inflammation Induced by microRNAs: Endometriosis-Derived Alterations in Circulating microRNA 125b-5p and Let-7b-5p Regulate Macrophage Cytokine Production. J Clin Endocrinol Metab 103, 64-74. 10.1210/jc.2017-01199.

Newman, A.I., Mauer-Vakil, D., Coo, H., Newton, L., Wilkerson, E., Mcknight, S., and Brogly, S.B. (2020). Rooming-in for Infants at Risk for Neonatal Abstinence Syndrome: Outcomes 5 Years following Its Introduction as the Standard of Care at One Hospital. Am J Perinatol. 10.1055/s-0040-1719182.

O'Connor, A.B., Collett, A., Alto. W.A., and O'Brien, L.M. (2013). Breastfeeding rates and the relationship between breastfeeding and neonatal abstinence syndrome in women maintained on buprenorphine during pregnancy. J Midwifery Womens Health 58, 383-388. 10.1111/jmwh.12009.

O'Connor, A.B., O'Brien, L., Alto, W.A., and Wong, J. (2016). Does concurrent in utero exposure to buprenorphine and antidepressant medications influence the course of neonatal abstinence syndrome? J Matern Fetal Neonatal Med 29, 112-114. 10.3109/14767058.2014.987750.

Oei, J., and Lui, K. (2007). Management of the newborn infant affected by maternal opiates and other drugs of dependency. J Paediatr Child Health 43, 9-18. 10.1111/j.1440-1754.2007.00994.x.

Oji-Mmuo, C.N., Gardner, F.C., and Doheny, K.K. (2018). Heightened sympathetic arousal is demonstrated by skin conductance responsivity to auditory stimuli in a small cohort of neonates with opiate withdrawal. Brain Res Bull 138, 106-111. 10.1016/j.brainresbull.2017.06.007.

Patrick, S.W., Slaughter, J.C., Harrell, F.E., Jr., Martin, P.R., Hartmann, K., Dudley, J., Stratton, S., and Cooper, W.O. (2021). Development and Validation of a Model to Predict Neonatal Abstinence Syndrome. J Pediatr 229, 154-160 e156. 10.1016/j.jpeds.2020.10.030.

R Core Team (2020). R: a language and environment for statistical computing (R Foundation for Statistical Computing).

Rosenthal, R. (1994), Parametric Measures of Effect Size. In The handbook of research synthesis., (Russell Sage Foundation), pp. 231-244.

Salem, N.A., Mahnke, A.H., Wells, A.B., Tseng, A.M., Yevtushok, L., Zymak-Zakutnya, N., Wertlecki, W ., Chambers, C.D., Miranda, R.C., and Collaborative Initiative on Fetal Alcohol Spectrum, D. (2020). Association between fetal sex and maternal plasma microRNA responses to prenatal alcohol exposure: evidence from a birth outcome-stratified cohort. Biol Sex Differ 11, 51. 10.1186/s13293-020-00327-2.

SAS Institute Inc. (2014). Chapter 60 The LOGISTIC Procedure. SAS/STAT® 13.2 User's Guide. SAS Institute Inc.

Shah, J.S., Soon, P.S., and Marsh, D.J. (2016). Comparison of Methodologies to Detect Low Levels of Hemolysis in Serum for Accurate Assessment of Serum microRNAs. PLOS One 11, e0153200. 10.1371/journal.pone.0153200.

Shahjin, F., Guda, R.S., Schaal, V.L., Odegaard, K., Clark, A., Gowen, A., Xiao, P., Lisco, S.J., Pendyala, G., and Yelamanchili, S.V. (2019). Brain-Derived Extracellular Vesicle microRNA Signatures Associated with In Utero and Postnatal Oxycodone Exposure. Cells 9. 10.3390/cells9010021.

Staszewski, C.L., Garretto, D., Garry, E.T., Ly, V., Davis, J.A., and Herrera, K.M. (2020). Comparison of buprenorphine and methadone in the management of maternal opioid use disorder in full term pregnancies. J Perinat Med 48, 677-680. 10.1515/jpm-2020-0106.

Stover, M.W., and Davis, J.M. (2015). Opioids in pregnancy and neonatal abstinence syndrome. Semin Perinatol 39, 561-565. 10.1053/j.semperi.2015.08.013.

Toyama, K., Kiyosawa, N., Watanabe, K., and Ishizuka, H. (2017). Identification of Circulating miRNAs Differentially Regulated by Opioid Treatment. Int J Mol Sci 18. 10.3390/ijms18091991.

Tseng, A.M., Mahnke, A.H., Wells, A.B., Salem, N.A., Allan, A.M., Roberts, V.H., Newman, N., Walter, N.A., Kroenke, C.D., Grant, K.A., et al. (2019). Maternal circulating miRNAs that predict infant FASD outcomes influence placental maturation. Life Sci Alliance 2. 10.26508/lsa.201800252.

Vasan, V., Kitase, Y., Newville, J., Robinson, S., Gerner, G., Burton, V., and Jantzie, L. (2021). Neonatal opioid exposure: public health crisis and novel neuroinflammatory disease. Neural Regeneration Research 16, 430-432. 10.4103/1673-5374.293136.

Wachman, E.M., Hayes, M.J., Lester, B.M., Terrin, N., Brown, M.S., Nielsen, D.A., and Davis, J.M. (2014). Epigenetic variation in the mu-opioid receptor gene in infants with neonatal abstinence syndrome. J Pediatr 165, 472-478. 10.1016/j.jpeds.2014.05.040.

Wachman, E.M., Schiff, D.M., and Silverstein, M. (2018). Neonatal Abstinence Syndrome: Advances in Diagnosis and Treatment. JAMA 319, 1362-1374. 10.1001/jama.2018.2640.

Yang, F.Q., Zhang, J.Q., Jin, J.J., Yang, C.Y., Zhang, W.J., Zhang, H.M., Zheng, J.H., and Weng, Z.M. (2018). HOXA11-AS promotes the growth and invasion of renal cancer by sponging miR-146b-5p to upregulate MMP16 expression. J Cell Physiol 233, 9611-9619. 10.1002/jcp.26864.

Zelson, C., Rubio, E., and Wasserman, E. (1971). Neonatal narcotic addiction: 10 year observation. Pediatrics 48, 178-189.

The invention claimed is:

1. A method of identifying and treating neonatal opioid withdrawal syndrome (NOWS) in a neonatal patient with said syndrome comprising:

(i) obtaining a blood sample from the neonatal patient, identifying and quantifying miRNA biomarkers hsa-miR-128-3p (SEQ ID NO:3), hsa-miR-421 (SEQ ID NO:18) and hsa-miR-30c-5p (SEQ ID NO:14) in the plasma and/or cellular fraction of the sample, comparing the concentrations of said biomarkers in the sample with a standard for each biomarker, wherein an up-regulated concentration of hsa-miR-128-3p (SEQ ID NO:3) and hsa-miR-421 (SEQ ID NO:18) and a down-regulated concentration of hsa-miR-30c-5p (SEQ ID NO:14) compared with a standard evidences opioid withdrawal syndrome in said neonatal patient, (ii) identifying the neonatal patient as having opioid withdrawal syndrome, and (iii) treating the neonatal patient identified as having opioid withdrawal syndrome with pharmacological opioid withdrawal syndrome therapy comprising administering to said patient an effective amount of at least one opiate selected from the group consisting of morphine, methadone, buprenorphine and tincture of opium, alone or in combination with at least one additional agent selected from the group consisting of a barbiturate, clonidine, a selective opium reuptake inhibitor (SSRI) and a benzodiazepine, wherein the biomarker standard is the concentration of the same biomarker in a blood sample obtained from a neonate or population of neonates without NOWS.

2. The method according to claim 1 wherein said miRNAs are measured in the plasma fraction of the neonate blood sample.

3. The method according to 1 wherein said opioid withdrawal syndrome therapy comprises administering to said neonate an effective amount of at least one opiate in combination with at least one additional agent selected from the group consisting of a barbiturate, clonidine, a selective serotonin reuptake inhibitor (SSRI) and a benzodiazepine.

4. The method according to claim 3 wherein said opioid withdrawal syndrome therapy comprises administering morphine, methadone, buprenorphine and/or tincture of opium alone to said patient.

5. The method according to claim 3 wherein said opioid withdrawal syndrome therapy comprises administering morphine, methadone, buprenorphine and/or tincture of opium in combination with a barbiturate and/or clonidine.

6. The method according to claim 4 wherein said opioid withdrawal syndrome therapy comprises administering methadone or buprenorphine to said patient.

7. The method according to claim 5 wherein said barbiturate is phenobarbital.

8. The method according to claim 6 wherein said opioid withdrawal syndrome therapy comprises administering morphine, methadone, buprenorphine and/or tincture of opium in combination with phenobarbital.

9. The method according to claim 5 wherein said opioid withdrawal syndrome therapy comprises administering morphine, methadone, buprenorphine and/or tincture of opium in combination with clonidine.

10. The method according to claim 5 wherein said opioid withdrawal syndrome therapy comprises administering morphine, methadone, buprenorphine and/or tincture of opium in combination with phenobarbital and clonidine.

11. The method according to claim 5 wherein said opioid withdrawal syndrome therapy comprises administering methadone and/or buprenorphine in combination with phenobarbital and/or clonidine to said patient.

12. The method according to claim 11 wherein said opioid withdrawal syndrome therapy comprises administering methadone or buprenorphine in combination with phenobarbital.

13. The method according to claim 11 wherein said opioid withdrawal syndrome therapy comprises administering methadone or buprenorphine in combination with clonidine.

14. The method according to claim 5 wherein said opioid withdrawal syndrome therapy comprises administering an SSRI and/or a benzodiazepine to said patient.

15. The method according to claim 3 wherein said opioid withdrawal syndrome therapy comprises administering morphine and/or methadone in combination with a SSRI and/or a benzodiazepine.

16. The method according to claim 1 wherein said neonate or population of neonates without NOWS is a neonate or population of neonates successfully treated for NOWS.

* * * * *